(12) United States Patent
Illig et al.

(10) Patent No.: US 7,705,042 B2
(45) Date of Patent: Apr. 27, 2010

(54) CLASS OF ARYLAMIDE COMPOUNDS USEFUL AS INHIBITORS OF C-FMS KINASE

(75) Inventors: Carl R. Illig, Phoenixville, PA (US); Shelley K. Ballentine, Lansdale, PA (US); Jinsheng Chen, Exton, PA (US); Sanath Meegalla, Boothwyn, PA (US); Jonathan Rudolph, Doylestown, PA (US); Mark J. Wall, Harleysville, PA (US); Kenneth J. Wilson, West Grove, PA (US); Renee DesJarlais, Saint Davids, PA (US); Carl L. Manthey, Downingtown, PA (US); Christopher M. Flores, Lansdale, PA (US); Christopher J. Molloy, Yardley, PA (US)

(73) Assignee: Janssen Pharmaceutica NV (BE)

( * ) Notice: Subject to any disclaimer, the term of this patent is extended or adjusted under 35 U.S.C. 154(b) by 1037 days.

(21) Appl. No.: 11/255,043

(22) Filed: Oct. 20, 2005

(65) Prior Publication Data
US 2006/0100201 A1    May 11, 2006

Related U.S. Application Data

(60) Provisional application No. 60/621,192, filed on Oct. 22, 2004.

(51) Int. Cl.
*A61K 31/34* (2006.01)

(52) U.S. Cl. .................... 514/461; 544/56; 544/60; 544/106; 544/359; 546/207; 546/268.1; 548/341.5; 548/564; 549/505

(58) Field of Classification Search .......... 514/461; 544/56, 60, 106, 359; 546/207, 268.1; 548/341.5, 548/564; 549/505
See application file for complete search history.

(56) References Cited

U.S. PATENT DOCUMENTS 5,700,823 A    12/1997    Hirth et al.
2003/0195230 A1    10/2003    Chen et al.

FOREIGN PATENT DOCUMENTS

WO    WO 2004/096795 A2    11/2004
WO    WO 2005/073193    *    8/2005
WO    WO 2006/047479    *    5/2006

OTHER PUBLICATIONS

Jordan, V. C. Nature Reviews: Drug Discovery, 2, 2003, p. 205.*
Vippagunta, et al. Advanced Drug Delivery Reviews, 48, 2001, p. 18.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Dumas, Jacques 'Protein Kinase Inhibitors: Emerging Pharmacophores 1997-2000' Exp. Opin. Ther. Patents (2001), 11(3), pp. 405-429.
International Search Report re: PCT/US2005/038341 dated Mar. 2, 2006.

* cited by examiner

*Primary Examiner*—James O Wilson
*Assistant Examiner*—Douglas M Willis

(57) ABSTRACT

The invention relates to arylamide and hetereoarylamide compounds of Formula I:

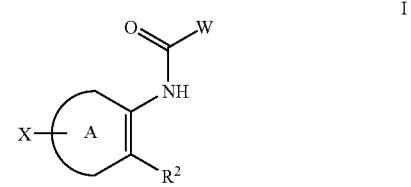

wherein A, X, $R^2$ and W are set forth in the specification, as well as tautomers and pharmaceutically acceptable salts thereof, that inhibit protein tyrosine kinases, especially c-fms kinase. Methods of treating autoimmune diseases; and diseases with an inflammatory component; treating metastasis from ovarian cancer, uterine cancer, breast cancer, colon cancer, stomach cancer, hairy cell leukemia and non-small lung carcinoma; and treating pain, including skeletal pain caused by tumor metastasis or osteoarthritis, or visceral, inflammatory, and neurogenic pain; as well as osteoporosis, Paget's disease, and other diseases in which bone resorption mediates morbidity including arthritis, prosthesis failure, osteolytic sarcoma, myeloma, and tumor metastasis to bone with the compounds of Formula I, are also provided.

11 Claims, No Drawings

CLASS OF ARYLAMIDE COMPOUNDS USEFUL AS INHIBITORS OF C-FMS KINASE

This application claims priority to provisional application, which is U.S. Ser. No. 60/621,192, filed Oct. 22, 2004. The complete disclosures of the aforementioned related U.S. patent applications are hereby incorporated herein by reference for all purposes.

CROSS-REFERENCE TO RELATED APPLICATIONS

Not applicable.

BACKGROUND OP THE INVENTION

1. Field of the Invention

The invention relates to novel compounds that function as protein tyrosine kinase inhibitors. More particularly, the invention relates to novel arylamide and hetereoarylamide compounds that function as inhibitors of c-fms kinase.

2. Description of Related Art

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Receptor tyrosine kinases of the epidermal growth factor ("EGF") family, which includes HER-1, HER-2/neu and HER-3 receptors, contain an extracellular binding domain, a transmembrane domain and an intracellular cytoplasmic catalytic domain. Receptor binding leads to the initiation of multiple intracellular tyrosine kinase dependent phosphorylation processes, which ultimately results in oncogene transcription. Breast, colorectal and prostate cancers have been linked to this family of receptors.

Insulin receptor ("IR") and insulin-like growth factor I receptor ("IGF-1R") are structurally and functionally related but exert distinct biological effects. IGF-1R over-expression has been associated with breast cancer.

Platelet derived growth factor ("PDGF") receptors mediate cellular responses that include proliferation, migration and survival and include PDGFR, the stem cell factor receptor (c-kit) and c-fms. These receptors have been linked to diseases such as atherosclerosis, fibrosis and proliferative vitreoretinopathy. These are type III Receptor tyrosine kinase family may or may not be PDGF.

Fibroblast growth factor ("FGR") receptors consist of four receptors which are responsible for the production of blood vessels, for limb outgrowth, and for the growth and differentiation of numerous cell types.

Vascular endothelial growth factor ("VEGF"), a potent mitogen of endothelial cells, is produced in elevated amounts by many tumors, including ovarian carcinomas. The known receptors for VEGF are designated as VEGFR-1 (Flt-1), VEGFR-2 (KDR), VEGFR-3 (Flt-4). A related group of receptors, tie-1 and tie-2 kinases, have been identified in vascular, endothelium and hematopoietic cells. VEGF receptors have been linked to vasculogenesis and angiogenesis.

Intracellular protein tyrosine kinases are also known as non-receptor protein tyrosine kinases. Over 24 such kinases have been identified and have been classified into 11 subfamilies. The serine/threonine protein kinases, like the cellular protein tyrosine kinases, are predominantly intracellular.

Diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity. Thus, a need exists for selective and potent small-molecule protein tyrosine kinase inhibitors. U.S. Pat. Nos. 6,383,790; 6,346,625; 6,235,746; 6,100,254 and PCT International Applications WO 01/47897, WO 00/27820 and WO 02/068406 are indicative of recent attempts to synthesize such inhibitors.

SUMMARY OF THE INVENTION

The invention addresses the current need for selective and potent protein tyrosine kinase inhibitors by providing potent inhibitors of c-fms kinase. The invention is directed to the novel compounds of Formula I:

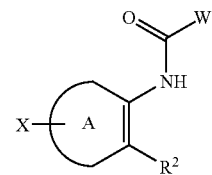

or a solvate, hydrate, tautomer or pharmaceutically acceptable salt thereof, wherein:

A is
  phenyl, pyridinyl, pyrazinyl, pyrimidinyl, or pyridazinyl, which may be substituted with one of chloro, fluoro, methyl, —$N_3$, —$NH_2$, —NH(alkyl), —N(alkyl)$_2$, —S(alkyl), —O(alkyl), alkylOC(O)alkyl, or 4-aminophenyl;

W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —CN, —$NO_2$, —OMe, C(=NH)NOH, or —$CF_3$ substitution, connected to any other carbon;

$R^2$ is piperidinyl, pyrrolyl or pyrrolidinyl, any of which may be independently substituted with one or two of each of the following: chloro, fluoro, oxo, and $C_{(1-3)}$alkyl, with the proviso that $R^2$ is connected to the ring A through the nitrogen atom;

X is

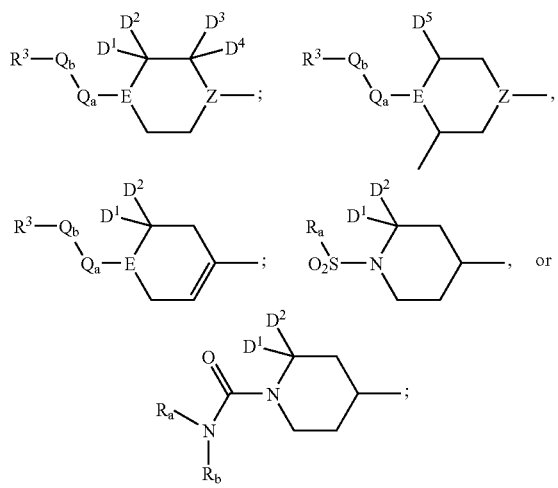

Z is
  CH or N;
D¹ and D² are
  hydrogens or taken together form a double bond to an oxygen;
D³ and D⁴ are
  hydrogens or taken together form a double bond to an oxygen;
D⁵ is
  hydrogen or —$CH_3$, wherein said —$CH_3$ may be relatively oriented syn or anti;
$R_a$ and $R_b$ are independently
  hydrogen, cycloalkyl, haloalkyl, aryl, aralkyl, heteroaryl, or heteroaralkyl;
E is
  N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
  absent, —$CH_2$—, —$CH_2CH_2$—, or C(O);
$Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
$R^3$ is
  hydrogen, phenyl, hydroxyalkylamino (including 2-hydroxy ethylamino), (hydroxyalkyl)₂amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
$R^4$ is
  hydrogen, —OH, alkoxy, carboxy, carboxamido, or carbamoyl.

The compounds of Formula I are especially potent inhibitors of the c-fms protein tyrosine kinase.

The invention also relates to methods of inhibiting protein tyrosine kinase activity in a mammal by administration of a therapeutically effective amount of at least one compound of Formula I.

DETAILED DESCRIPTION OF THE INVENTION

The invention is directed to the novel compounds of Formula I:

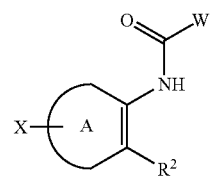

or a solvate, hydrate, tautomer or pharmaceutically acceptable salt thereof, wherein:
A is
  phenyl, pyridinyl, pyrazinyl, pyrimidinyl, or pyridazinyl, which may be substituted with one of chloro, fluoro, methyl, —$N_3$, —$NH_2$, —NH(alkyl), —N(alkyl)₂, —S(alkyl), —O(alkyl), alkylOC(O)alkyl, or 4-aminophenyl;
W is
  pyrrolyl (including 1H-pyrrol-2-yl), imidazolyl, (including 1H-imidazol-2-yl), isoxazolyl, oxazolyl, 1,2,4 triazolyl, or furanyl (including furan-2-yl), any of which may be connected through any carbon atom, wherein the pyrrolyl, imidazolyl, isoxazolyl, oxazolyl, 1,2,4 triazolyl, or furanyl may contain one —CN, —$NO_2$, —OMe, C(=NH)NOH, or —$CF_3$ substitution, connected to any other carbon;
$R^2$ is piperidinyl, pyrrolyl or pyrrolidinyl, any of which may be independently substituted with one or two of each of the following: chloro, fluoro, oxo, and $C_{(1-3)}$alkyl, with the proviso that $R^2$ is connected to the ring A through the nitrogen atom;
X is

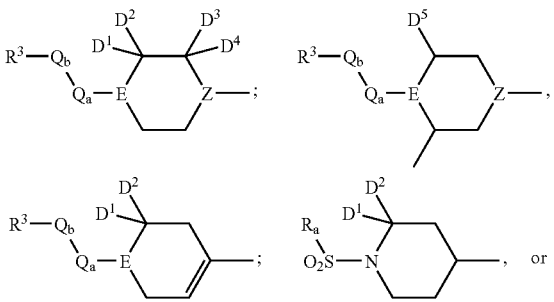

-continued

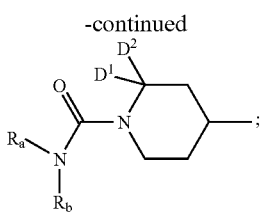

Z is
  CH or N;
$D^1$ and $D^2$ are
  hydrogens or taken together form a double bond to an oxygen;
$D^3$ and $D^4$ are
  hydrogens or taken together form a double bond to an oxygen;
$D^5$ is
  hydrogen or —$CH_3$, wherein said —$CH_3$ may be relatively oriented syn or anti;
$R_a$ and $R_b$ are independently
  hydrogen, cycloalkyl, haloalkyl, aryl, aralkyl, heteroaryl, or heteroaralkyl;
E is
  N, S, O, SO or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N;
$Q_a$ is
  absent, —$CH_2$—, —$CH_2CH_2$—, or C(O);
$Q_b$ is
  absent, —NH—, —$CH_2$—, —$CH_2CH_2$—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if $R^3$ is an amino group or cyclic amino radical wherein the point of attachment to $Q_b$ is N;
$R^3$ is
  hydrogen, phenyl, hydroxyalkylamino (including 2-hydroxy ethylamino), (hydroxyalkyl)$_2$amino, hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —$CONH_2$, —CN, —$SO_2$-alkyl-$R^4$ (including —$SO_2CH_3$), —$NH_2$, or a 5 or six membered ring which contains at least one heteroatom N and may optionally contain an additional heteromoiety selected from S, $SO_2$, N, and O, and the 5 or 6 membered ring may be saturated, partially unsaturated or aromatic (including piperidinyl, morpholinyl, imidazolyl, and pyridyl) wherein aromatic nitrogen in the 5 or 6 membered ring may be present as N-oxide (including pyridyl N-oxide), and the 5 or 6 membered ring may be optionally substituted with methyl, halogen, alkylamino, or alkoxy (including 1 methyl imidazolyl); $R^3$ may also be absent, with the proviso that $R^3$ is not absent when E is nitrogen;
$R^4$ is
  hydrogen, —OH, alkoxy, carboxy, carboxamido, or carbamoyl.

Preferred compounds of Formula I are those wherein:
A is
  phenyl which may be substituted with one of chloro, fluoro, methyl, or 4-aminophenyl;
X is
  attached to the phenyl A ring para to the nitrogen substituent, as depicted in formula II;

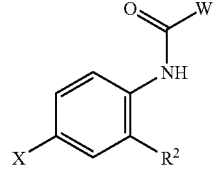

II $D^3$ and $D^4$ are hydrogen.
E is N or $SO_2$;
$R^3$ is
  hydrogen, piperidinyl, alkylamino, hydroxyalkylamino, (hydroxyalkyl)$_2$amino, alkylamino, imidazolyl, 1-methyl imidazolylimidazolyl, pyridyl, pyridyl N-oxide, hydroxyalkyl, —COOH, —$CONH_2$, —CN, —$SO_2CH_3$, —$NH_2$, morpholine; $R^3$ may also be absent; with the proviso that $R^3$ is not absent when E is nitrogen.
Preferred compounds of Formula I are those wherein
W is substituted with one —CN.
Other preferred compounds of Formula I are those wherein:
A is
  pyridyl, which may be substituted with one of chloro, fluoro, methyl, —$N_3$, —$NH_2$, —NH(alkyl), —N(alkyl)$_2$, —S(alkyl), —O(alkyl), or 4-aminophenyl;
W is
  imidazolyl, (including 1H-imidazol-2-yl), which may contain one —CN; and
$R^2$ is
  cycloalkyl.
More preferred compounds of Formula I are those wherein:
A is
  phenyl which may be substituted with 4-aminophenyl;
W is
  furan-2-yl, 1H-pyrrol-2-yl, or 1H-imidazol-2-yl, either of which may be substituted at the 4 or 5 carbons with —CN;
$R^2$ is
  piperidinyl which may be substituted with one of each of the following chloro, fluoro, and $C_{(1-3)}$alkyl.
Even more preferred compounds of Formula I are those wherein:
W is
  3H-2-imidazolyl-4-carbonitrile or 5-cyano-1H-pyrrol-2-yl;
$R^2$ is
  piperidinyl optionally substituted with fluoro or methyl;
E is N and
Z is CH.
Especially preferred compounds of Formula I are those wherein:
W is
  imidazolyl, (including 1H-imidazol-2-yl), 1,2,4 triazolyl, or furanyl (including furan-2-yl), any of which may be connected through any carbon atom, wherein the imidazolyl, 1,2,4 triazolyl, or furanyl may contain one —Cl or —CN, connected to any other carbon;

R² is
cycloalkyl (including $C_{(1-3)}$alkyl substituted cycloalkyl, further including $C_{(1-3)}$alkyl substituted cyclopentenyl, and $C_{(1-3)}$alkyl substituted cyclohexenyl, further including 4-methyl cyclohexenyl), $C_{(1-3)}$dialkyl substituted cycloalkyl (including 4,4-dimethyl cyclohexenyl), thiophenyl (including $C_{(1-3)}$alkyl substituted thiophenyl, further including 2-methyl thiophenyl and 3-methyl thiophenyl), $C_{(1-3)}$alkyl substituted phenyl (including methyl phenyl), dihydropyranyl, and 1,1-dioxo-tetrahydrothiopyranyl;

X is

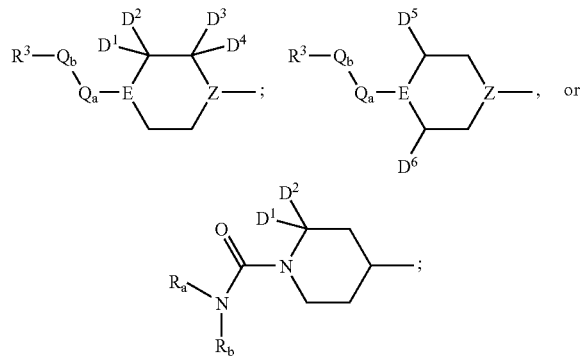

E is
N or $SO_2$, with the proviso that E may not be N if the following three conditions are simultaneously met: $Q_a$ is absent, $Q_b$ is absent, and $R^3$ is an amino group or cyclic amino radical wherein the point of attachment to E is N; and R³ is
hydrogen, phenyl, hydroxyalkylamino (including 2-hydroxy ethylamino), hydroxyalkyl(alkyl)amino (including 1-hydroxyeth-2-yl(methyl)amino), alkylamino (including methylamino), aminoalkyl (including 2-amino isopropyl), dihydroxyalkyl (including 1,3-dihydroxy isopropyl, 1,2-dihydroxy ethyl), alkoxy (including methoxy), dialkylamino (including dimethylamino), hydroxyalkyl (including 1-hydroxy eth-2-yl), —COOH, —CONH₂, —CN, —SO₂CH₃, —NH₂, or a 5 or six membered ring selected from the group consisting of: piperidinyl, morpholinyl, imidazolyl, and pyridyl, wherein the 5 or 6 membered ring may be optionally substituted with methyl, halogen, alkylamino, or alkoxy (including 1 methyl imidazolyl), R³ may also be absent, with the proviso that R³ is not absent when E is nitrogen.

Most preferred compounds of Formula I are those wherein:
W is
3H-2-imidazolyl-4-carbonitrile;
$Q_a$ is CO;
R³ is
hydrogen, piperidine, alkylamine, hydroxyalkylamine, (hydroxyalkyl)₂amine, alkylamine, dialkylamine, imidazole, 1-methyl imidadole, pyridine, pyridine N-oxide, hydroxyalkyl, —COOH, —CONH₂, —CN, —SO₂CH₃, —NH₂, morpholine.

The compounds of Formula I are especially potent inhibitors of the c-fms protein tyrosine kinase.

The invention also relates to methods of inhibiting protein tyrosine kinase activity in a mammal by administration of a therapeutically effective amount of at least one compound of Formula I.

Examples of compounds of Formula I are:
5-Cyano-furan-2-carboxylic acid (4-morpholin-4-yl-2-piperidin-1-yl-phenyl)-amide;
5-Cyano-furan-2-carboxylic acid [4-(4-methyl-piperazin-1-yl)-2-piperidin-1-yl-phenyl]-amide
5-Cyano-furan-2-carboxylic acid (2-piperidin-1-yl-4-thiomorpholin-4-yl-phenyl)-amide;
5-Cyano-furan-2-carboxylic acid [4-(1-oxo-1λ⁴-thiomorpholin-4-yl)-2-piperidin-1-yl-phenyl]-amide;
5-Cyano-furan-2-carboxylic acid [4-(1,1-dioxo-1λ⁶-thiomorpholin-4-yl)-2-piperidin-1-yl-phenyl]-amide;
5-Cyano-furan-2-carboxylic acid [5-chloro-4-(4-methyl-piperazin-1-yl)-2-piperidin-1-yl-phenyl]-amide;
5-Cyano-furan-2-carboxylic acid [5-(4-methyl-piperazin-1-yl)-2-piperidin-1-yl-phenyl]-amide;
5-Cyano-furan-2-carboxylic acid (5-morpholin-4-yl-2-piperidin-1-yl-phenyl)-amide;
5-Cyano-furan-2-carboxylic acid [2-(4-methyl-piperidin-1-yl)-4-morpholin-4-yl-phenyl]-amide;
5-Cyano-furan-2-carboxylic acid [4-(4-methyl-piperazin-1-yl)-2-(4-methyl-piperidin-1-yl)-phenyl]-amide;
4-[4-[(5-Cyano-furan-2-carbonyl)-amino]-3-(4-methyl-piperidin-1-yl)-phenyl]-piperazine-1-carboxylic acid benzyl ester;
4-[4-[(5-Cyano-furan-2-carbonyl)-amino]-3-(4-methyl-piperidin-1-yl)-phenyl]-piperazine-1-carboxylic acid tert-butyl ester;
5-Cyano-furan-2-carboxylic acid [2-(4-methyl-piperidin-1-yl)-4-piperazin-1-yl-phenyl]-amide tris(trifluoroacetic acid salt);
5-Cyano-furan-2-carboxylic acid [4-(4-acetyl-piperazin-1-yl)-2-(4-methyl-piperidin-1-yl)-phenyl]-amide;
5-Cyano-furan-2-carboxylic acid [4-(4-methanesulfonyl-piperazin-1-yl)-2-(4-methyl-piperidin-1-yl)-phenyl]-amide;
Carbonic acid tert-butyl ester 2-{4-[4-[(5-cyano-furan-2-carbonyl)-amino]-3-(4-methyl-piperidin-1-yl)-phenyl]-piperazin-1-yl}-ethyl ester;
5-Cyano-furan-2-carboxylic acid [4-[4-(2-hydroxy-ethyl)-piperazin-1-yl]-2-(4-methyl-piperidin-1-yl)-phenyl]-amide trifluoroacetic acid salt;
5-Cyano-furan-2-carboxylic acid [5-fluoro-4-(4-methyl-piperazin-1-yl)-2-(4-methyl-piperidin-1-yl)-phenyl]-amide;
5-Cyano-furan-2-carboxylic acid (4-azido-2-piperidin-1-yl-phenyl)-amide;
5-(N-Hydroxycarbamimidoyl)-furan-2-carboxylic acid (2,4-di-piperidin-1-yl-phenyl)-amide;
5-Cyano-furan-2-carboxylic acid [4-(4-methyl-pyrazol-1-yl)-2-piperidin-1-yl-phenyl]-amide;
4-Methyl-piperazine-1-carboxylic acid {4-[(5-cyano-furan-2-carbonyl)-amino]-3-piperidin-1-yl-phenyl}-methyl-amide;
5-Cyano-furan-2-carboxylic acid [4-(methanesulfonyl-methyl-amino)-2-piperidin-1-yl-phenyl]-amide
Acetic acid {4-[(5-cyano-furan-2-carbonyl)-amino]-3-piperidin-1-ylphenylcarbamoyl}-methyl ester;
5-Cyano-furan-2-carboxylic acid (4-methanesulfonylamino-2-piperidin-1-yl-phenyl)-amide;
5-Cyano-furan-2-carboxylic acid [4-methyl-6'-(4-methyl-piperidin-1-yl)-3,4,5,6-tetrahydro-2H-[1,2']-bipyrazinyl-5'-yl]-amide;
5-Cyano furan-2-carboxylic acid [4-(4-methyl-piperazin-1-yl)-2-piperidin-1-yl-phenyl]-amide hydrochloride;
4-[4-[(5-Cyano-furan-2-carbonyl)-amino]-3-(2,5-dimethyl-pyrrol-1-yl)-phenyl]-piperazine-1-carboxylic acid tert-butyl ester;

4-[4-(4-Methyl-piperazin-1-yl)-2-piperidin-1-yl-phenylcarbamoyl]-oxazole-2-carboxylic acid methyl ester;

5-Cyano-furan-2-carboxylic acid [2-(4-methyl-piperidin-1-yl)-4-(1,2,3,6-tetrahydro-pyridin-4-yl)-phenyl]-amide dihydrochloride;

5-Cyano-furan-2-carboxylic acid [2-(4-methyl-piperidin-1-yl)-4-piperidin-4-yl-phenyl]-amide bis(trifluoracetic acid salt);

4-Cyano-1H-pyrrole-2-carboxylic acid [2-(4-methyl-piperidin-1-yl)-4-piperidin-4-yl-phenyl]-amide bis(trifluoracetic acid salt);

5-Cyano-furan-2-carboxylic acid [4-(1-acetyl-piperidin-4-yl)-2-(4-methyl-piperidin-1-yl)-phenyl]-amide;

5-Cyano-1H-imidazole-2-carboxylic acid [4-(4-methyl-piperazin-1-yl)-2-piperidin-1-yl-phenyl]-amide trifluoroacetic acid salt;

3H-Imidazole-4-carboxylic acid [4-(4-methyl-piperazin-1-yl)-2-piperidin-1-yl-phenyl]-amide bis(trifluoroacetic acid salt);

1H-Imidazole-2-carboxylic acid [4-(4-methyl-piperazin-1-yl)-2-piperidin-1-yl-phenyl]-amide bis(trifluoroacetic acid salt);

3H-Imidazole-2,4-dicarboxylic acid 2-amide 4-{[4-(4-methyl-piperazin-1-yl)-2-piperidin-1-yl-phenyl]-amide}trifluoroacetic acid salt;

1H-Imidazole-2-carboxylic acid [3-chloro-4-(4-methyl-piperazin-1-yl)-2-piperidin-1-yl-phenyl]-amide bis(trifluoroacetic acid salt);

4-[4-[2-(4-Cyano-1H-pyrrol-2-yl)-2-oxo-ethyl]-3-(4-methyl-piperidin-1-yl)-phenyl]-piperidine-1-carboxylic acid (2-dimethylamino-ethyl)-amide;

4-Cyano-1H-pyrrole-2-carboxylic acid [4-[1-(imidazole-1-carbonyl)-piperidin-4-yl]-2-(4-methyl-piperidin-1-yl)-phenyl]-amide;

4-Cyano-1H-pyrrole-2-carboxylic acid {2-(4-methyl-piperidin-1-yl)-4-[1-(pyridine-3-carbonyl)-piperidin-4-yl]-phenyl}-amide;

4-Cyano-1H-pyrrole-2-carboxylic acid [4-[1-(2-dimethylamino-acetyl)-piperidin-4-yl]-2-(4-methyl-piperidin-1-yl)-phenyl]-amide;

4-Cyano-1H-pyrrole-2-carboxylic acid {2-(4-methyl-piperidin-1-yl)-4-[1-(2,2,2-trifluoroethyl)-piperidin-4-yl]-phenyl}-amide;

4-Cyano-1H-imidazole-2-carboxylic acid [4-(1,1-dioxo-hexahydro-1$\lambda^6$-thiopyran-4-yl)-2-(4-methyl-piperidin-1-yl)-phenyl]-amide;

4-[4-[(4-Cyano-1H-pyrrole-2-carbonyl)-amino]-3-(4-methyl-piperidin-1-yl)-phenyl]-piperidine-1-carboxylic acid (2-hydroxy-ethyl)-amide;

4-Cyano-1H-pyrrole-2-carboxylic acid {2-(4-methyl-piperidin-1-yl)-4-[1-(morpholin-4-carbonyl)-piperidin-4-yl]-phenyl}-amide;

4-[4-[(4-Cyano-1H-pyrrole-2-carbonyl)-amino]-3-(4-methyl-piperidin-1-yl)-phenyl]-piperidine-1-carboxylic acid 2-dimethylamino-ethyl ester;

4-Cyano-1H-pyrrole-2-carboxylic acid [4-[1-(2-methanesulfonyl-acetyl)-piperidin-4-yl]-2-(4-methyl-piperidin-1-yl)-phenyl]-amide;

4-Cyano-1H-pyrrole-2-carboxylic acid [4-(1,1-dioxo-hexahydro-1$\lambda^6$-thiopyran-4-yl)-2-(4-methyl-piperidin-1-yl)-phenyl]-amide;

4-Cyano-1H-pyrrole-2-carboxylic acid [4-(4-methyl-piperazin-1-yl)-2-piperidin-1-yl-phenyl]-amide;

4-Cyano-1H-pyrrole-2-carboxylic acid [4-(4-methyl-piperazin-1-yl)-2-(4-methyl-piperidin-1-yl)-phenyl]-amide;

5-Cyano-furan-2-carboxylic acid [4-methyl-6'-(4-methyl-piperazin-1-yl)-3,4,5,6-tetrahydro-2H-[1,2']bipyridinyl-3'-yl]-amide;

4-Cyano-1H-pyrrole-2-carboxylic acid [2-(4-methyl-piperidin-1-yl)-4-piperazin-1-yl-phenyl]-amide bis(trifluoroacetic acid salt);

4-Cyano-1H-pyrrole-2-carboxylic acid [4-(4-acetyl-piperazin-1-yl)-2-(4-methyl-piperidin-1-yl)-phenyl]-amide;

4-Cyano-1H-pyrrole-2-carboxylic acid [4-methyl-6'-(4-methyl-piperazin-1-yl)-3,4,5,6-tetrahydro-2H-[1,2']bipyridinyl-3'-yl]-amide;

5-Cyano-furan-2-carboxylic acid[2-(methyl-piperazin-1-yl)-4-(methyl-piperidin-5-yl]-amide trifluoroacetic acid salt;

5-Cyano-furan-2-carboxylic acid[4-methyl-5'-(4-methyl-piperazin-1-yl)-3,4,5,6-tetrahydro-2H-[1,3']bipyridinyl-2'-yl]-amide;

5-Cyano-furan-2-carboxylic acid[4-methyl-6'-(4-methyl-2-oxo-piperazin-1-yl)-3,4,5,6-tetrahydro-2H— [1,3']bipyridinyl-2'-yl]-amide;

5-Cyano-furan-2-carboxylic acid[4-methyl-6'-(4-methyl-3-oxo-piperazin-1-yl)-3,4,5,6-tetrahydro-2H-[1,2']bipyridinyl-3'-yl]-amide;

5-Cyano-furan-2-carboxylic acid[4,1''-dimethy-3,4,5,6,1'',2'',3'',4'',5'',6''-decahydro-2H-{1,2',6',4''}terpyridin-3'-yl)-amide;

5-Cyano-furan-2-carboxylic acid[4-[4-methyl-pierazin-1-yl)-2-morpholin-4-yl-phenyl]-amide;

5-Cyano-furan-2-carboxylic acid [4-methyl-6'-(tetrahydro-pyran-4-yl)-3,4,5,6-tetrahydro-2H-[1,2']bipyridinyl-3'-yl]-amide;

5-Cyano-1H-imidazole-2-carboxylic acid [4-methyl-6'-(tetrahydro-pyran-4-yl)-3,4,5,6-tetrahydro-2H-[1,2']bipyridinyl-3'-yl]-amide;

5-Cyano-furan-2-carboxylic acid {4-methyl-6'-[4-(2-morpholin-4-yl-2-oxo-ethyl)-piperazin-1-yl]-3,4,5,6-tetrahydro-2H-[1,2']bipyridinyl-3'-yl}-amide;

5-Cyano-furan-2-carboxylic acid {4-methyl-6'-[4-(2-morpholin-4-yl-acetyl)-piperazin-1-yl]-3,4,5,6-tetrahydro-2H-[1,2']bipyridinyl-3'-yl}-amide trifluoroacetic acid salt;

5-Cyano-furan-2-carboxylic acid [2-(4-fluoro-piperidin-1-yl)-4-(4-methyl-piperazin-1-yl)-phenyl]-amide trifluoroacetic acid salt; and 4-Cyano-1H-imidazole-2-carboxylic acid [2-(3-fluoro-piperidin-1-yl)-4-(4-methyl-piperazin-1-yl)-phenyl]-amine tris(trifluoroacetic acid salt).

The invention also relates to methods of inhibiting protein tyrosine kinase activity in a mammal by administration of a therapeutically effective amount of at least one compound of Formula I. A preferred tyrosine kinase is c-fms.

The invention is considered to include the enantiomeric, diastereomeric and tautomeric forms of all compounds of Formula I as well as their racemic mixtures. In addition, some of the compounds represented by Formula I may be prodrugs, i.e., derivatives of an acting drug that possess superior delivery capabilities and therapeutic value as compared to the acting drug. Prodrugs are transformed into active drugs by in vivo enzymatic or chemical processes.

I. Definitions

The term "alkyl" refers to both linear and branched chain radicals of up to 12 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "hydroxyalkyl" refers to both linear and branched chain radicals of up to 6 carbon atoms, in which one hydrogen atom has been replaced with an OH group.

The term "hydroxyalkylamine" refers to an hydroxyalkyl group in which one hydrogen atom from the carbon chain has been replaced with an amino group, wherein the nitrogen is the point of attachment to the rest of the molecule.

The term "cycloalkyl" refers to a saturated or partially unsaturated ring composed of from 3 to 8 carbon atoms. Up to four alkyl substituents may optionally be present on the ring. Examples include cyclopropyl, 1,1-dimethyl cyclobutyl, 1,2,3-trimethylcyclopentyl, cyclohexyl and cyclohexenyl.

The term "heterocyclyl" refers to a nonaromatic (i.e. saturated or partially unsaturated) ring composed of from 3 to 7 carbon atoms and at least one heteroatom selected from N, O or S. Alkyl substituents may optionally be present on the ring. Examples include tetrahydrofuryl, dihydropyranyl, piperidyl, 2,5-dimethypiperidyl, morpholinyl, piperazinyl, thiomorpholinyl, pyrrolidinyl, pyrrolinyl, pyrazolidinyl, pyrazolinyl, imidazolidinyl and imidazolinyl.

The term "dihydrosulfonopyranyl" refers to the following radical:

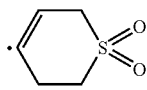

The term "heterocyclylalkyl" refers to a $C_{1-6}$ alkyl group containing a heterocyclyl substituent. Examples include dihydropyranylethyl and 2-morpholinylpropyl.

The term "hydroxyalkyl" refers to at least one hydroxyl group bonded to any carbon atom along an alkyl chain.

The term "aminoalkyl" refers to at least one primary or secondary amino group bonded to any carbon atom along an alkyl chain, wherein an alkyl group is the point of attachment to the rest of the molecule.

The term "alkylamino" refers to an amino with one or two alkyl substituents, wherein the amino group is the point of attachment to the rest of the molecule.

The term "alkoxyalkyl" refers to at least one alkoxy group bonded to any carbon atom along an alkyl chain.

The term "polyalkoxyalkyl" refers to long-chain alkoxy compounds and includes polyethylene glycols of discreet or monodispersed sizes.

The term "thioalkyl" refers to at least one sulfur group bonded to any carbon atom along an alkyl chain. The sulfur group may be at any oxidation state and includes sulfoxides, sulfones and sulfates.

The term "carboxyalkyl" refers to at least one carboxylate group bonded to any carbon atom along an alkyl chain. The term "carboxylate group" includes carboxylic acids and alkyl, cycloalkyl, aryl or aralkyl carboxylate esters.

The term "heteroaromatic" or "heteroaryl" refers to 5- to 7-membered mono- or 8- to 10-membered bicyclic aromatic ring systems, any ring of which may consist of from one to four heteroatoms selected from N, O or S where the nitrogen and sulfur atoms can exist in any allowed oxidation state. Examples include benzimidazolyl, benzothiazolyl, benzothienyl, benzoxazolyl, furyl, imidazolyl, isothiazolyl, isoxazolyl, oxazolyl, pyrazinyl, pyrazolyl, pyridyl, pyrimidinyl, pyrrolyl, quinolinyl, thiazolyl and thienyl.

The term "heteroaralkyl" refers to a $C_{1-6}$ alkyl group having a heteroaryl substituent. Examples include furylethyl and 2-quinolinylpropyl.

The term "heteroatom" refers to a nitrogen atom, an oxygen atom or a sulfur atom wherein the nitrogen and sulfur atoms can exist in any allowed oxidation states.

The term "alkoxy" refers to straight or branched chain radicals of up to 12 carbon atoms, unless otherwise indicated, bonded to an oxygen atom. Examples include methoxy, ethoxy, propoxy, isopropoxy and butoxy.

The term "aryl" refers to monocyclic or bicyclic aromatic ring systems containing from 6 to 12 carbons in the ring. Alkyl substituents may optionally be present on the ring. Examples include benzene, biphenyl and napththalene.

The term "aralkyl" refers to a $C_{1-6}$ alkyl group containing an aryl substituent. Examples include benzyl, phenylethyl or 2-naphthylmethyl.

The term "heteroaralkyl" refers to a $C_{1-6}$ alkyl group containing a heteroaryl substituent. Examples include furylmethyl and pyridylpropyl.

The term "aryloxy" refers to an oxygen atom bound to an aryl substituent. Examples include phenoxy and benzyloxy.

The term "arylalkoxy" refers to an alkoxy group bound to an aryl substituent. Examples include phenylmethyl ether.

The term "acyl" refers to the group $-C(O)R_a$, where $R_a$ is alkyl, aryl, aralkyl, heteroaryl and heteroaralkyl. An "acylating agent" adds the $-C(O)R_a$ group to a molecule.

The term "sulfonyl" refers to the group $-S(O)_2R_a$, where $R_a$ is hydrogen, alkyl, cycloalkyl, haloalkyl, aryl, aralkyl, heteroaryl and heteroaralkyl. A "sulfonylating agent" adds the $-S(O)_2R_a$ group to a molecule.

II. Therapeutic Uses

The compounds of Formula I represent novel potent inhibitors of protein tyrosine kinases, such as c-fms, and may be useful in the prevention and treatment of disorders resulting from actions of these kinases.

The invention also provides methods of inhibiting, a protein tyrosine kinase comprising contacting the protein tyrosine kinase with an effective inhibitory amount of at least one of the compounds of Formula I. A preferred tyrosine kinase is c-fms. The compounds of the present invention are also inhibitors of FLT3 tyrosine kinase activity. In one embodiment of inhibiting a protein tyrosine kinase, at least one of the compounds of Formula I is combined with a known tyrosine kinase inhibitor.

In various embodiments of the invention, the protein tyrosine kinases inhibited by the compounds of Formula I are located in cells, in a mammal or in vitro. In the case of mammals, which includes humans, a therapeutically effective amount of a pharmaceutically acceptable form of at least one of the compounds of Formula I is administered.

The invention further provides methods of treating cancer in mammals, including humans, by administration of a therapeutically effective amount of a pharmaceutically acceptable composition of least one compound of Formula I. Exemplary cancers include, but are not limited to, acute myeloid leukemia, acute lymphocytic leukemia, ovarian cancer, uterine cancer, breast cancer, colon cancer, stomach cancer, hairy cell leukemia and non-small lung carcinoma. The invention also provides methods of treating certain precancerous lesions including myelofibrosis. In one embodiment of the invention, an effective amount of at least one compound of Formula I is administered in combination with an effective amount of a chemotherapeutic agent.

The invention further provides methods of treating and of preventing metastasis arising from cancers that include, but are not limited to, ovarian cancer, uterine cancer, breast cancer, colon cancer, stomach cancer, hairy cell leukemia and non-small lung carcinoma.

The invention further provides methods for the treatment osteoporosis, Paget's disease, and other diseases in which bone resorption mediates morbidity including arthritis, prosthesis failure, osteolytic sarcoma, myeloma, and tumor metastasis to bone as occurs frequently in cancers including, but not limited to, breast cancer, prostate cancer, and colon cancer.

The invention also provides methods of treating pain, in particular skeletal pain caused by tumor metastasis or osteoarthritis, as well as visceral, inflammatory, and neurogenic pain.

The invention also provides methods of treating cardiovascular and inflammatory diseases in mammals, including humans, by administration of a therapeutically effective amount of a pharmaceutically acceptable form of at least one of the compounds of Formula I. Examples of diseases that may be effectively treated include atherosclerosis, cardiac hypertrophy, glomerulonephritis, rheumatoid arthritis, psoriasis, diabetes, tumor related angiogenesis, restenosis, schizophrenia and Alzheimer's dementia. These may be effectively treated with compounds of this invention. Other diseases that may be effectively treated include, but are not limited to atherosclerosis and cardiac hypertrophy. Autoimmune diseases such as systemic lupus erythematosus, rheumatoid arthritis, Sjogren's syndrome, multiple sclerosis, or uveitis, can also be treated with compounds of this invention.

When employed as protein tyrosine kinase inhibitors, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamine salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

III. Methods of Preparation

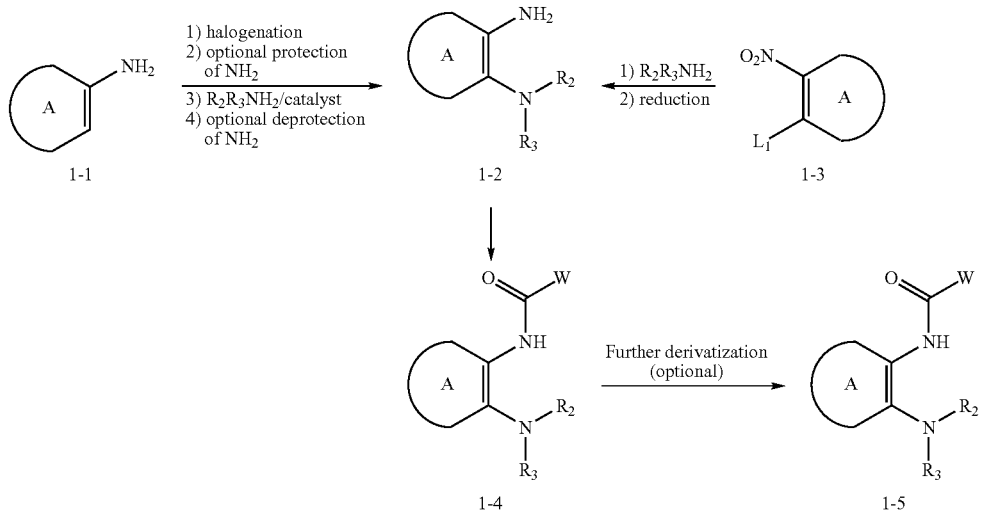

Scheme 1

Scheme 1 illustrates general methodology for the preparation of compounds of Formula I.

Compounds of Formula 1-2 can be obtained by nucleophilic aromatic substitution on compounds of Formula 1-3 (where $L_1$ is a leaving group such as a halogen, preferably fluoro or chloro) with amines $R_2R_3NH$ followed by reduction of the nitro group. Nucleophilic aromatic displacements can be performed in the presence of a suitable base such as excess $R_2R_3NH$, $NEt_3$ or $K_2CO_3$ in a suitable solvent such as DMF. Nitro reductions can be performed according to standard synthetic methodologies (for a review, see M. Hudlicky, Reductions in Organic Chemistry, Wiley, N.Y. (1984)) and include preferred methods such as palladium-catalyzed hydrogenolysis or treatment with iron (0) and $NH_4Cl$ (see, for example, S. Mitsumori, et al, J. Med. Chem., 46: 2436-45 (2003)).

Alternatively compounds of Formula 1-2 can be obtained by ortho-halogenation (preferably bromination) of amino compounds of Formula 1-1 followed by metal-catalyzed aminations with $R_2R_3NH$. (For reviews, see: S. L. Buchwald, et al, *Top. Curr. Chem.*, 219:131-209 (2001) and J. F. Hartwig in "*Organopalladium Chemistry for Organic Synthesis*," Wiley Interscience, NY (2002) and examples therein.) Catalysts suitable for aminations include metal complexes and salts of palladium and copper as described below and in the aforementioned references. The $NH_2$ group may be optionally protected prior to the coupling using a number of protecting groups such as tert-butoxycarbonyl (BOC) (see, for example, M. C. Harris, et al, *Org. Lett.*, 4:2885-8 (2002).) (For examples of amine protecting groups and their use, see Theodora W. Greene and Peter G. M. Wuts, John Wiley and Sons, Inc., NY (1991)). The preferred conditions for bromination are N-bromosuccinimide (NBS) in a suitable solvent such as N,N-dimethylformamide (DMF), dichloromethane (DCM) or acetonitrile. Metal-catalyzed aminations can be performed according to standard methodology, preferably in the presence of a palladium catalyst such as $Pd_2(dba)_3$ or $Pd(OAc)_2$, a ligand such as BINAP or preferably 2-diphenylphoshino-2'-(N,N-dimethylamino)biphenyl, a base such as $Cs_2CO_3$, and a suitable solvent such as toluene, dioxane or DME. The protecting group, if present, would then be removed at this point using suitable reagents, preferably trifluoroacetic acid in DCM if the protecting group was a BOC.

Compounds of Formula 1-4 can be prepared by reaction of compounds of Formula 1-2 with carboxylic acids WCOOH according to standard procedures for amide bond formation (for a review, see: M. Bodansky and A. Bodansky, The Practice of Peptide Synthesis, Springer-Verlag, NY (1984)) or by reaction with acid chlorides WCOCl or activated esters $WCO_2Rq$ (where Rq is a leaving group such as pentafluorophenyl or N-succinimide). The preferred reaction conditions for coupling with WCOOH are: when W is a furan, oxalyl chloride in DCM with DMF as a catalyst to form the acid chloride WCOCl and then coupling in the presence of a trialkylamine such as N,N-diisopropylethylamine (DIEA); when W is a pyrrole, 1-(3-dimethylaminopropyl)-3-carbodiimide hydrochloride (EDCl) and 1-hydroxybenzotriazole (HOBt); and when W is an imidazole, the preferred conditions are bromotri(pyrrolidino)phosphonium hexafluorophosphate (PyBroP) and DIEA in DCM.

It should be understood that the optional substitution present in Formula I may be present in the starting materials 1-1 or 1-3 and, in such cases, would be carried through the synthesis outlined in Scheme 1. Alternatively various substituents on compounds of Formula I may be introduced in a number of ways described below to provide the optional substitution listed for Formula I. For example, leaving groups present on compounds of Formula 1-1 or 1-3, can be substituted before or at any step during Scheme 1. When such leaving groups (preferably fluoro or chloro) are activated by the nitro group of Formula 1-3 for nucleophilic attack, they can undergo direct nucleophilic aromatic substitution by ammonia and azide anion or by amines, alcohols, thiols and other nucleophiles in the presence of a suitable base such as $K_2CO_3$, DIEA or $NEt_3$. When the leaving group is suitable for metal-catalyzed couplings (preferably bromo or trifluoromethanesulfonyloxy), a number of cross-coupling reactions (such as Suzuki or Stille reactions) may be performed to introduce aryl, heteroaryl, alkenyl or cycloalkenyl groups (for reviews, see N. Miyaura, A. Suzuki, *Chem. Rev.*, 95:2457 (1995), J. K. Stille, *Angew. Chem, Int. Ed. Engl.*, 25: 508024 (1986) and A. Suzuki in Metal-Catalyzed Coupling Reactions, F. Deiderich, P. Stang, Eds., Wiley-VCH, Weinheim (1988)). Metal-catalyzed cross-couplings (preferably Suzuki reactions using a boronic acid or boronic ester) can be performed according to standard methodology, preferably in the presence of a palladium catalyst such as $Pd(PPh_3)_4$, an aqueous base such as aq. $Na_2CO_3$, and a suitable solvent such as toluene, ethanol, DME, or DMF. Other metal-catalyzed coupling reactions that can be employed include aromatic and heteroaromatic amination and amidation (for reviews, see references for amination chemistry cited above for conversion of Formulas 1-1 to 1-2.)

When the products of a cross-coupling reaction contain an olefin, the olefin can be reduced, if desired, preferably by hydrogenation in the presence of a catalyst such as palladium on carbon in a suitable solvent such as methanol or THF, to give the corresponding saturated product.

In some cases, the initial substituents formed can be further derivatized as described below to provide the final substitution of Formula I.

An alternative method to direct substitution to introduce nitrogen-containing heterocyclic substituents onto ring A is to form the heterocycle from an aniline amino group on ring A. The aniline amino group may be originally present in the starting material in a protected or unprotected form or may result from the reduction of a nitro group which also can be either originally present in the starting material or attached by a nitration reaction. In addition, the amino group may be formed by reduction of an azide group which can be present in the starting material or may result from nucleophilic aromatic substitution of an activated halide by azide anion as mentioned above. The amino group may also result from nucleophilic aromatic substitution of an activated halide (in, for example a nitrohalo compound) by ammonia or by the anion of a protected ammonia equivalent, for example, t-butyl carbamate. If introduced in protected form, the amine can be deprotected according to standard literature methods. (For examples of amine protecting groups and deprotection methods see: Theodora W. Greene and Peter G. M. Wuts, John Wiley and Sons, Inc., NY (1991).) The ring-forming reaction involves treatment of the aniline amino group with a suitable optionally substituted di-electrophile, preferably a dihalide or dicarbonyl compound, which results in two substitutions on the amino group to form an optionally substituted heterocycle. In the case of dihalides, any of a number of suitable bases can be added as an acid scavenger such as potassium carbonate, sodium hydroxide, or, a trialkylamine such as triethylamine. Thus, treatment with a bis(2-haloethyl)amine such as bis(2-chloroethyl)amine or bis(2-bromoethyl)amine would afford a piperazine ring (see, for example, *J. Med. Chem.*, 29: 640-4 (1986) and *J. Med. Chem.*, 46: 2837 (2003)). Optional substitution on the amine nitrogen of the reagent would incorporate optional substitution on the terminal amine of the piperazine. For example, treatment with N,N-bis(2-chloroethyl)aniline would give an N-phenylpiperazino group. Treatment with a bis(2-haloethyl)ether or bis(2-haloethyl)thioether would afford a morpholine or thiomorpholine ring, respectively. Treatment with an optionally substituted dihaloalkane such as 1,5-dibromopentane or 1,4-dibromobutane would form a piperidine or pyrrolidine, respectively. For example, treatment with 1,5-dibromo-3,3-dimethylpentane would form the corresponding 3,3-dimethylpiperidino group (see, for example, *J. Org. Chem.*, 50: 2690-8 (1985) and *J. Org. Chem.*, 66: 8127-34 (2001)). Also, treatment with a dihalodialkylketone could provide a carbonyl containing nitrogen heterocycle. For example, bis(2-bromoethyl)ketone could afford the 4-piperidone ring, (see, *Helv. Chim. Acta*, 86: 799-811 (2003)). Treatment with a dicarbonyl compound can also provide nitrogen heterocycles.

For example, treatment with hexane-2,5-dione can provide a 2,5-dimethylpyrrole group (see, *Synthesis,* 86: 1599 (1998)).

Another alternative method to direct substitution to introduce heterocyclic substituents onto ring A is to form the heterocycle from an aldehyde (i.e. from a formyl group on ring A). The formyl group may be originally present in the starting material in a protected or unprotected form or may result from any of a number of formylation reactions known in the literature including a Vilsmeier-Haack reaction (for a review of formylation chemistry, see: G. A. Olah, et al, Chem Rev., 87: (1987)) or by para-formylation of nitroaromatics (see: A. Katritsky and L. Xie, *Tetrahedron Lett.,* 37:347-50 (1996)).

Finally it is understood that substituents on compounds of Formula 1-4 may be further derivatized to provide compounds of Formula 1-5. Protecting groups on compounds of Formula 1-4 can be removed according to standard synthetic methodologies (see Theodora W. Greene and Peter G. M. Wuts, John Wiley and Sons, Inc., NY (1991)) and can be then subjected to further derivatization. Examples of further derivatization of compounds of 1-4 to provide compounds of Formulae 1-5 include, but are not limited to: when compounds of Formula 1-4 contain a primary or secondary amine, the amine may be reacted with aldehydes or ketones in the presence of a reducing agent such as sodium triacetoxyborohydride (see Abdel-Magid reference above) to reductively alkylate the amine; with acid chlorides or carboxylic acids and an amide bond forming reagent as described above to form amides; with sulfonyl chlorides to form sulfonamides; with isocyanates or carbamyl chlorides to form ureas; with aryl or heteroaryl halides in the presence of a palladium catalyst as described above (see Buchwald and Hartwig references above) to attach aryl and heteroaryl groups to the amines. In addition, when compounds of Formulae 1-4 contain an aryl or heteroaryl halide (preferably bromide) or an aryl or heteroaryl trifluoromethanesulfonyloxy group, these compounds may be further subjected to metal-catalyzed reactions with boronic acids (for example, Suzuki or Stille couplings as described above) to attach aryl, heteroaryl, alkenyl or cycloalkenyl groups, or with amines, alcohols or thiols (Buchwald- or Hartwig-type couplings, see Buchwald and Hartwig references above) to attach various amino, alkoxy, aryloxy, alkylthio or arylthio groups. When compounds of Formula 1-4 contain a cyano group, this group may be hydrolyzed to amides or acids under acid or basic conditions. The resulting acids may the coupled to amines to form amides using the methology described above. Basic amines may be oxidized to N-oxides and conversely N-oxides may be reduced to basic amines. When compounds of Formula 1-4 contain a sulfide, either acyclic or cyclic, the sulfide can be further oxidized to the corresponding sulfoxides or sulfones. Sulfoxides can be obtained by oxidation using an appropriate oxidant such as one equivalent of MCPBA or by treatment with $NaIO_4$ (see, for example, J. Regan, et al, *J. Med. Chem.,* 46: 4676-86 (2003)) and sulfones can be obtained using two equivalents of MCPBA or by treatment with 4-methylmorpholine N-oxide and catalytic osmium tetroxide (see, for example, PCT application WO 01/47919).

Scheme 2a

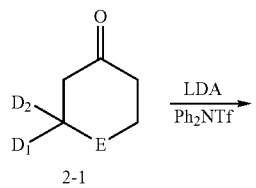

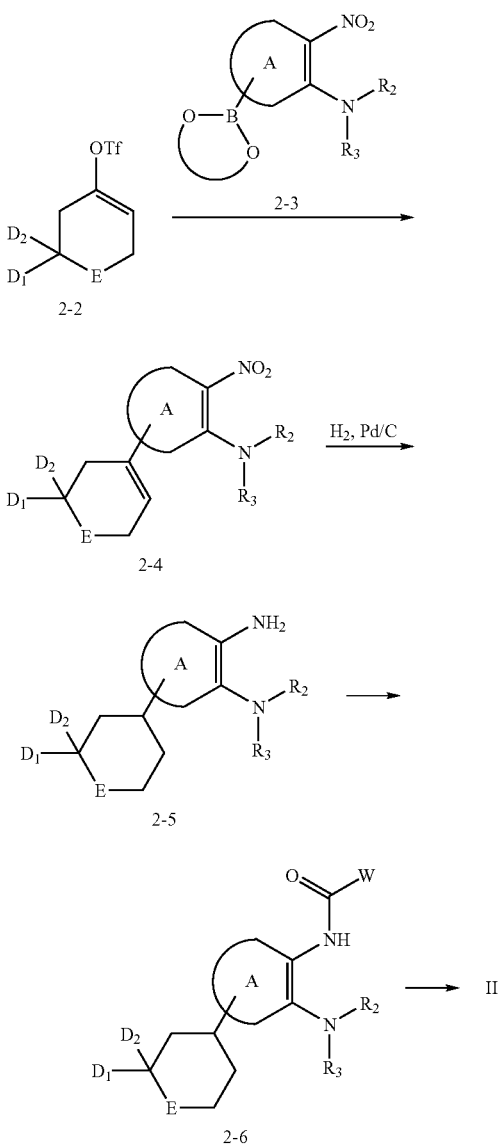

Scheme 2a illustrates a route to compounds when (Z=CH) where E represents —$NQR_3$—, —O-($D_1$=$D_2$=H), —S-($D_1$=$D_2$=H), —SO-($D_1$=$D_2$=H), or —$SO_2$-($D_1$=$D_2$=H). Ketones of formula 2-1 can be converted to a vinyl triflate of formula 2-2 by treatment with a non-nucleophilic base such as LDA and then trapping of the resulting enolate with a triflating reagent such as trifluoromethanesulfonic anhydride or preferably N-phenyltrifluoromethanesulfonimide. Suzuki coupling of boronic acids or boronate esters of formula 2-3 (prepared by palladium catalyzed borylation, see for example *J. Org. Chem.,* 60: 7508 (1995)), to vinyl triflates of formula 2-2 provide compounds of formula 2-4 (see, for example, *Synthesis,* 993 (1991)). Compounds of Formula 2-4 where E=—SO— or —$SO_2$— are obtained by oxidation of compounds of Formula 2-4 where E=—S— with a reagent such as MCPBA (one equivalent for E=—SO—, two equivalents for E=—$SO_2$—) or by other methods as described in Scheme 1.

Compounds of formula 2-5 are obtained by reduction of the olefin and nitro group with Pd/C. Following the methods described in Scheme 1, compounds of formula 2-5 are then converted by amide bond formation into compounds of formula 2-6, which also represent compounds of Formula I if no further substitution or modification is required.

Compounds of formula 2-6 may be further modified to provide additional compounds of Formula I. For example, in cases where E is —NQR$_3$—, Q=a direct bond, and R$_3$ represents a BOC protecting group (CO$_2$t-Bu), the BOC group may be removed according to standard methodology such as trifluoroacetic acid (TFA) in DCM (Greene and Wuts, ibid.) to provide a secondary amine that can then be further derivatized to provide compounds of Formula I. Further derivatization includes, but is not limited to: reactions with aldehydes or ketones in the presence of a reducing agent such as sodium triacetoxyborohydride to provide compounds of Formula I where E=—NCH$_2$R$_3$ (see Abdel-Magid *J. Org. Chem.* 61, pp. 3849-3862, (1996)); with acid chlorides or with carboxylic acids and an amide bond forming reagent (as described in Scheme 1) to provide compounds of Formula I where E=—NCOR$_3$; with sulfonyl chlorides (as described in Scheme 1) to provide compounds of Formula I where E=—NSO$_2$R$_a$; with isocyanates (as described in Scheme 1) to provide compounds of Formula I where E=—NCONR$_a$R$_b$; or subjected to metal-catalyzed substitution reactions as outlined in Scheme 1 to provide compounds of Formula I where E=—NR$_3$. (S. L. Buchwald, et al, ibid.; J. H. Hartwig, ibid.)

Scheme 2b

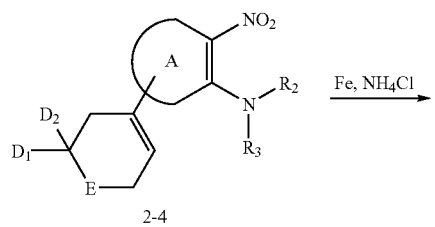

2-4

-continued

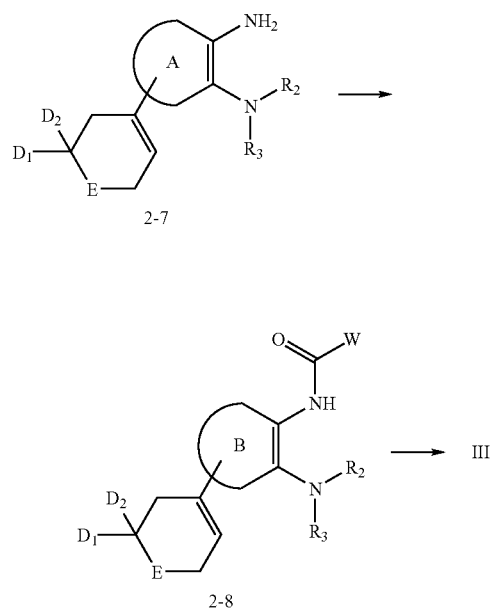

Scheme 2b illustrates a modification of Scheme 2a to synthesize compounds of Formula I. E represents —NQR$_3$—, —O-(D$_1$=D$_2$=H), —S-(D$_1$=D$_2$=H), —SO-(D$_1$=D$_2$=H), or —SO$_2$-(D$_1$=D$_2$=H). Compounds of formula 2-4 are prepared as shown in Scheme 2a. Compounds of formula 2-7 are obtained by NO$_2$ group reduction by a method that does not reduce olefins such as iron and ammonium chloride (as described in Scheme 1). Compounds of Formula I are then obtained as described in Scheme 1 and Scheme 2a.

Scheme 3

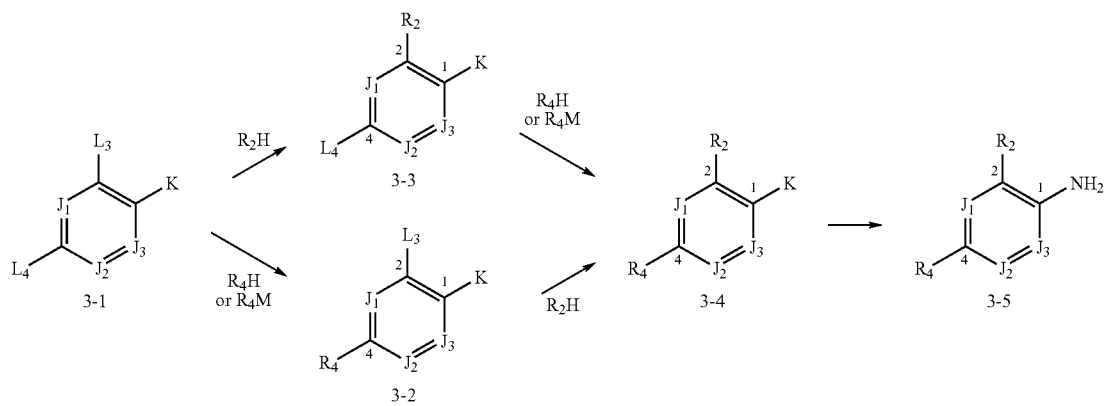

Scheme 3 illustrates the preparation of intermediates for the synthesis of compounds of Formula I, where ring A is a 6-membered heterocycle, $R_1$=H, and $R_4$ is the optional substitution on ring A or one of the heterocyclic substituents as defined above. At least one of the $J_1$, $J_2$ and $J_3$ in Formula 3-1 is N and the remainder are N or C—R (R is H, halogen, CN, C1-$C_6$ alkyl, $C_1$-$C_4$ alkoxy, $CF_3$, aralkyl, heteroarylkyl, aryl, aryloxy, COORa, CONRaRb, as defined supra). K=$NH_2$ or other functional groups such as $NO_2$, COOH or COOR which can eventually be converted to amino group by known literature methods such as reductions for $NO_2$ (as discussed for Scheme 1) or Curtius rearrangement for COOH (for a review, see *Organic Reactions*, 3: 337 (1947)). $L_3$ and $L_4$ are halogens. (K=COOH can also be formed from K=COOR by simple base- or acid-catalyzed hydrolysis.)

In general, the selectivity and order in introducing $R^2$ and $R^5$ can be achieved by the relative reactivity of the halogens $L^3$ and $L^4$ chosen in compound (3-1), the intrinsic selectivity of the heterocycle and/or the reaction conditions employed. An example of using the relative reactivity of the halogens $L^3$ and $L^4$ in selectively introducing $R^2$ and $R^5$ would include the situation where, in compounds of Formula 3-1 where $L^3$ is a fluoro group and $L^4$ is a bromo group, selective displacement of the fluoro group by a nucleophile can be achieved followed by substitution of the remaining bromo group by metal-catalyzed substitution chemistry (such as Suzuki or Stille cross-coupling reactions as further outlined below). Similarly in compounds of Formula 3-1 where one of $L^3$ and $L^4$ is an iodo group and the other is a bromo or chloro group, selective metal-catalyzed substitution chemistry (such as Suzuki or Stille cross-coupling reactions or Buchwald/Hartwig aminations as further discussed below) on the iodo group can be achieved followed by replacement of the remaining bromo or chloro group by another metal-catalyzed substitution reaction.

As illustrated in Scheme 3, leaving group $L_3$ in Formula 3-1 can be first substituted to obtain compounds of Formula 3-3 or leaving group $L_4$ can be first substituted to obtain compound of Formula 3-2. Compounds 3-2 or 3-3 can then be reacted to displace $L_3$ or $L_4$ to furnish the compound of Formula 3-4.

A direct nucleophilic displacement or metal-catalyzed amination of compound of Formula 3-1 with a secondary amine, ammonia or a protected amine such as tert-butyl carbamate (for review, see Modern Amination Methods: Ricci, A., Ed.; Wiley-VCH: Weinheim, 2000), can be used to introduce $R_2$ or $R_4$ in Formula 3-2 or 3-3 where $R_2$ or $R_4$ is a primary or secondary amine, amino group ($NH_2$), and amine equivalent or a protected amino group. Metal-catalyzed coupling of compound 3-1 with boronic acids or boronates esters (Suzuki reaction, M=boronic acid group or boronate ester group) or with organotin compounds (Stille reaction, M=$SnR_3$, where R=alkyl and the other substituents as defined above, as described in Scheme 1 can provide compounds of Formula 3-2 or 3-3.

Compound 3-2 also can be converted to compound 3-4 by a direct nucleophilic displacement or metal-catalyzed amination with a primary or secondary amine, ammonia or a protected amine such as tert-butyl carbamate as described above. $L_4$ in compound 3-3 also can be substituted with $R_4$ to obtain compound of Formula 3-4 by a direct nucleophilic substitution or metal catalyzed reaction with N nucleophile or by metal-catalyzed cross-coupling reaction as described above. When $R_2$ or $R_4$ in formula (3-2, 3-3 or 3-4) is a protected amine and K not an amino group, it can be deprotected to unmask the amino functionality. This amino functionality can then be further derivatized as described in Scheme 1. When the K group in Formula 3-4 is not an amino group (such as functionality described above), it can be converted to an amino group according to known literature methods (see, for example Comprehensive Organic Transformations: Larock, R. S.; Wiley and Sons Inc., USA, 1999) and the resulting amine 3-5 can be employed in amide bond formation reactions as described in Scheme (1) to obtain the compounds in Formula I. When K in Formula 3-4 is an amino group it can be directly used in amide coupling as described above.

Scheme 4a

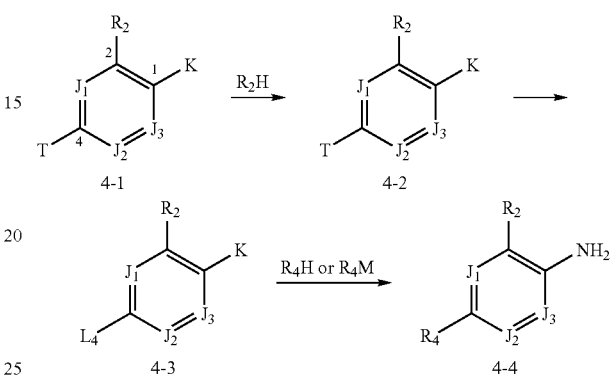

Scheme 4b

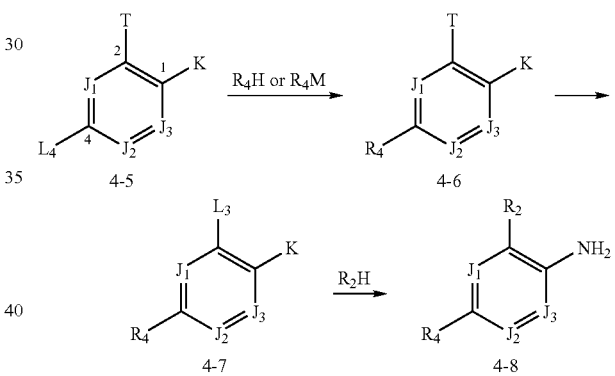

Scheme 4 illustrates the preparation of intermediates to be further modified according to Scheme 3 starting from a monohalo-substituted compound of Formula 4-1 and 4-5 by introducing the second leaving group after the replacement of the first one has been completed. These can also be used for the synthesis of compounds of Formula I where ring A is a 6-membered heterocycle and $R_4$ is the optional substitution on Ring A or one of the heterocyclic substituents. As in Scheme 3, at least one of $J_1$, $J_2$ and $J_3$ are N and the remainder are N or C—R (R=H, halogen, CN, $C_1$-$C_6$ alkyl, et al.). K=$NH_2$ or other functional groups such as $NO_2$, COOH or COOR which can eventually be converted to amino group by known literature methods such as reductions or Curtius rearrangement as described in Scheme 3. $L_3$ and $L_4$ are halogens. In these compounds, T is either H or a functional group such as OH that can be converted to leaving groups $L_3$ or $L_4$ such as halogen, triflate or mesylate by known literature methods (see, for example, Nicolai, E., et al., *J. Heterocyclic Chemistry*, 31, (73), (1994)). Displacement of $L_3$ in compound of Formula 4-1 or $L_4$ in Formula 4-5 by methods described in Scheme 3, can yield compounds of Formula 4-2 and 4-6. At this point, the substituent T of compound 4-2 or 4-6 can be converted to a halogen by standard methods to provide compounds of Formula 4-3 and 4-5. For example, when T=OH, the preferred reagents to effect this transformation are thionyl chloride, PCl$_5$, POCl$_3$ or PBr$_3$ (see, for examples, Kolder, den Hertog., *Recl. Trav. Chim.* Pays-Bas; 285, (1953), Iddon, B, et. Al., *J. Chem. Soc. Perkin Trans.* 1., 1370, (1980)). When T=H, it can be directly halogenated (preferably brominated) to provide compounds of formula 4-3 or 4-7 (see, for example, Canibano, V. et al., *Synthesis,* 14, 2175, (2001)). The preferred conditions for bromination are NBS in a suitable solvent such as DCM or acetonitrile.

The compounds of Formulae 4-3 or 4-7 can be converted to compounds of Formulae 4-4 or 4-8 by introduction of the remaining groups R$_2$ or R$_4$ respectively, as described above and then on to compounds of Formula I, by the methods described in Scheme 3 for conversion of compounds of Formulae 3-2 and 3-3 to compounds of Formula I.

This invention is illustrated by the following examples.

xample 1

5-Cyano-furan-2-carboxylic acid

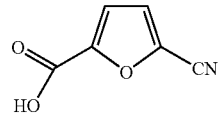

To 2.8 g of 2-formyl-5-furancarboxylic acid (20 mmol) and 2.7 g of hydroxylamine hydrochloride (40 mmol) under Ar was added and dry pyridine (50 mL). The mixture was heated to 85° C., acetic anhydride (40 mL) was added and the mixture was stirred for 3 h. After cooling to 60° C., water (250 mL) was added and the mixture was stirred at RT for 70 h. The mixture was acidified to pH 2 with concentrated hydrochloric acid and extracted with 3:1 dichloromethane-isopropanol (8×100 mL). The combined organic layers were washed with water (100 mL), brine (100 mL), dried over anh sodium sulfate and concentrated in vacuo to afford the title compound as a tan solid (1.26 g, 46%). $^1$H-NMR (CD$_3$OD; 400 MHz): δ 14.05 (br s, 1H), 7.74 (d, OH, J=3.8 Hz), 7.42 (d, 1H, J=3.8 Hz).

Example 2

4-Cyano-1H-pyrrole-2-carboxylic acid

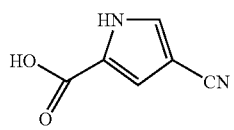

The title compound was prepared by the literature procedure (Loader and Anderson, *Canadian J. Chem.,* 59: 2673 (1981)).

Example 3

4-Cyano-1-(2-trimethylsilanyl-ethoxymethyl)-1H-imidazole-2-carboxylate potassium salt

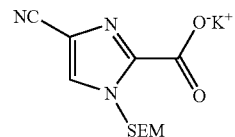

a) 1-(2-Trimethylsilanyl-ethoxymethyl)-1H-imidazole-4-carbonitrile

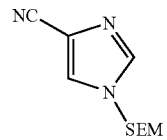

A flask charged with imidazole-4-carbonitrile (0.50 g, 5.2 mmol) (*Synthesis,* 677 (2003)) 2-(trimethylsilyl)ethoxymethyl chloride (SEMCl) (0.95 mL, 5.3 mmol), K$_2$CO$_3$ (1.40 g, 10.4 mmol), and acetone (5 mL) was stirred for 10 h at RT. The mixture was diluted with EtOAc (20 mL) and washed with water (20 mL) and brine (20 mL) and the organic layer dried over MgSO$_4$. The crude product was eluted from a 20-g SPE cartridge (silica) with 30% EtOAc/hexane to give 0.80 g (70%) of the title compound as a colorless oil. Mass spectrum (CI(CH$_4$), m/z) Calcd. for C$_{10}$H$_{17}$N$_3$OSi, 224.1 (M+H), found 224.1.

b) 2-Bromo-1-(2-trimethylsilanyl-ethoxymethyl)-1H-imidazole-4-carbonitrile

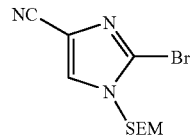

To a solution of 1-(2-trimethylsilanyl-ethoxymethyl)-1H-imidazole-4-carbonitrile (0.70 g, 3.1 mmol) (as prepared in the previous step) in CCl$_4$ (10 mL) was added NBS (0.61 g, 3.4 mmol) and AIBN (2 mg, catalytic), and the mixture heated at 60° C. for 4 h. The reaction was diluted with EtOAc (30 mL) and washed with NaHCO$_3$ (2×30 mL) and brine (30 mL) and the organic layer was dried over Na$_2$SO$_4$ and then concentrated. The title compound was eluted from a 20-g SPE cartridge (silica) with 30% EtOAc/hexane to give 0.73 g (77%) of a yellow solid. Mass spectrum (CI(CH$_4$), m/z) Calcd. for C$_{10}$H$_{16}$BrN$_3$OSi, 302.0/304.0 (M+H), found 302.1/304.1.

c) 4-Cyano-1-(2-trimethylsilanyl-ethoxymethyl)-1H-imidazole-2-carboxylic acid ethyl ester

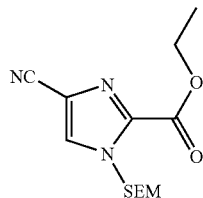

To a solution of 2-bromo-1-(2-trimethylsilanyl-ethoxymethyl)-1H-imidazole-4-carbonitrile (0.55 g, 1.8 mmol) (as prepared in the previous step) in THF (6 mL) at −40° C. was added drop wise a solution of 2M i-PrMgCl in THF (1 mL). The reaction was allowed to stir for 10 min at −40° C. and then cooled to −78° C., and ethyl cyanoformate (0.3 g, 3.0 mmol) was added. The reaction allowed to attain RT and stirred for 1 h. The reaction was quenched with satd aq NH$_4$Cl, diluted with EtOAc (20 mL) and washed with brine (2×20 mL), and the organic layer was dried over Na$_2$SO$_4$ and then concentrated. The title compound was eluted from a 20-g SPE cartridge (silica) with 30% EtOAc/hexane to give 0.40 g (74%) of a colorless oil. Mass spectrum (ESI, m/z): Calcd. for C$_{13}$H$_{21}$N$_3$O$_3$Si, 296.1 (M+H), found 296.1.

d) 4-Cyano-1-(2-trimethylsilanyl-ethoxymethyl)-1H-imidazole-2-carboxylate potassium salt To a solution of 4-cyano-1-(2-trimethylsilanyl-ethoxymethyl)-1H-imidazole-2-carboxylic acid ethyl ester (0.40 g, 1.3 mmol) (as prepared in the previous step) in ethanol (3 mL) was added a solution of 6M KOH (0.20 mL) and the reaction was stirred for 10 min and then concentrated to give 0.40 g (100%) of the title compound as a yellow solid. $^1$H-NMR (400 MHz, CD$_3$OD) δ 7.98 (s, 1H), 5.92 (s, 2H), 3.62 (m, 2H), 0.94 (m, 2H), 0.00 (s, 9H). Mass spectrum (ESI-neg, m/z) Calcd. for C$_{11}$H$_{17}$N$_3$O$_3$Si, 266.1 (M−H), found 266.0.

Example 4

5-Cyano-furan-2-carboxylic acid (4-morpholin-4-yl-2-piperidin-1-yl-phenyl)-amide

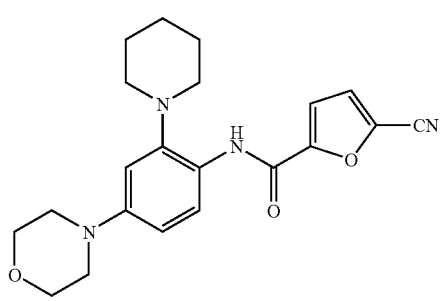

a) 1-(5-Chloro-2-nitro-phenyl)-piperidine

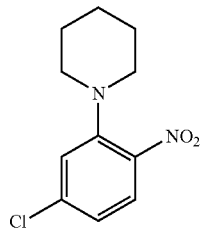

To a cooled (0° C.) solution of 1.75 g (10.0 mmol) of 4-chloro-2-fluoronitrobenzene in 15 mL of EtOH was added 2.97 mL (30.0 mmol) of piperidine dropwise over 5 min. The solution stirred at 0° C. for 10 min and then at 23° C. for 30 min. The mixture was poured into water (225 mL) and extracted with EtOAc (2×30 mL). The combined extracts were washed with saturated aq NaHCO$_3$ and brine (30 mL each) and then dried (Na$_2$SO$_4$) Concentration afforded 2.33 g (97%) of the title compound as an orange oil which crystallized on standing: Mass spectrum (ESI, m/z): Calcd. for C$_{11}$H$_{13}$ClN$_2$O$_2$, 241.1 (M+H), found 241.1.

b) 4-(4-Nitro-3-piperidin-1-yl-phenyl)-morpholine

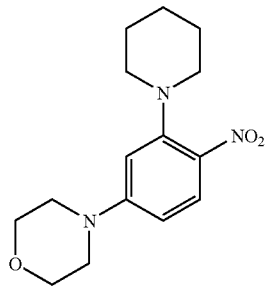

A mixture of 150 mg (0.623 mmol) 1-(5-chloro-2-nitro-phenyl)-piperidine (as prepared in the previous step) and 272 μL (3.12 mmol) of morpholine were heated with stirring under Ar at 125° C. for 84 h. After cooling to rt, the mixture was poured into water (40 mL) and extracted with EtOAc (2×20 mL). The combined extracts were washed with water (2×10 mL) and brine (10 mL) and then dried (Na$_2$SO$_4$) Concentration afforded 162 mg (89%) of the title compound as an orange resin: Mass spectrum (ESI, m/z): Calcd. for C$_{15}$H$_{21}$N$_3$O$_3$, 292.2 (M+H), found 292.1.

c) 5-Cyano-furan-2-carboxylic acid (4-morpholin-4-yl-2-piperidin-1-yl-phenyl)-amide

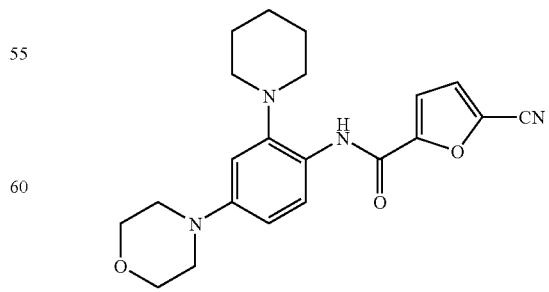

A mixture of 38.8 mg (0.131 mmol) 4-(4-nitro-3-piperidin-1-yl-phenyl)-morpholine (as prepared in the previous step)

and 38 mg of 10% palladium on carbon (Degussa type E101-NE/W, Aldrich, 50% by weight water) in 2 mL of THF was stirred vigorously under a balloon of hydrogen for 1 h. The mixture was filtered (Celite) washing with dichloromethane (2×1 mL) and the solution of the resulting aniline was placed under Ar and used immediately in the following reaction.

Simultaneously to the above reduction, 18.0 mg (0.131 mmol) of 5-cyanofuran-2-carboxylic acid (as prepared in Example 1) in 1.5 mL of anh dichloromethane under a CaSO$_4$ drying tube was treated with 22.9 µL (0.262 mmol) of oxalyl chloride followed by 10 µL of anh DMF. The solution was stirred for 1 h and quickly concentrated in vacuo at 25° C. or less. The resulting 5-cyanofuran-2-carbonyl chloride was placed under high vacuum for only 2-3 min and then immediately placed under Ar, cooled to 0° C. in an ice bath, and treated with the aniline solution produced above followed by 34.3 µL (0.197 mmol) of N,N-diisopropylethylamine (DIEA). After stirring 30 min at RT, the mixture was concentrated in vacuo and the resulting residue flash chromatographed on a 5-g silica SPE column with 20% EtOAc-hexane to afford 38.8 mg (78%) of the title compound as a yellow solid: $^1$H-NMR (CDCl$_3$; 400 MHz): δ 9.53 (br s, 1H), 8.33 (d, 1H, J=8.9 Hz), 7.26 (d, 1H, J=3.7 Hz, partially obscured by CHCl$_3$ peak), 7.22 (d, 1H, J=3.7 Hz), 6.78 (d, 1H, J=2.7 Hz), 6.71 (dd, 1H, J=8.9, 2.7 Hz), 3.87 (m, 4H), 3.14 (m, 4H), 2.85 (m, 4H), 1.81 (m, 4H), and 1.65 (br m, 2H). Mass spectrum (ESI, m/z): Calcd. for C$_{21}$H$_{24}$N$_4$O$_3$, 381.2 (M+H), found 381.2.

Example 5

5-Cyano-furan-2-carboxylic acid [4-(4-methyl-piperazin-1-yl)-2-piperidin-1-yl-phenyl]-amide

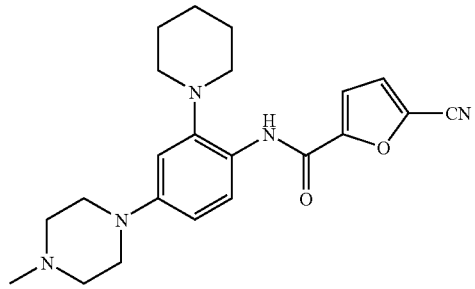

a) 1-Methyl-4-(4-nitro-3-piperidin-1-yl-phenyl)-piperazine

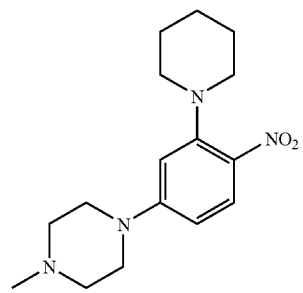

A mixture of 350 mg (1.45 mmol) of 1-(5-chloro-2-nitrophenyl)-piperidine (as prepared in Example 4, step (a)) and 482 µL (4.35 mmol) of 1-methylpiperazine was heated in a sealed vial at 138° C. for 30 h. The mixture was cooled and poured into 60 mL of water and extracted with EtOAc (2×20 mL). The combined extracts were washed with brine (30 mL), dried (Na$_2$SO$_4$) and concentrated in vacuo to afford 436 mg (99%) of the title compound as a yellow resin: Mass spectrum (ESI, m/z): Calcd. for C$_{16}$H$_{24}$N$_4$O$_2$, 305.2 (M+H), found 305.2.

b) 5-Cyano-furan-2-carboxylic acid [4-(4-methyl-piperazin-1-yl)-2-piperidin-1-yl-phenyl]-amide

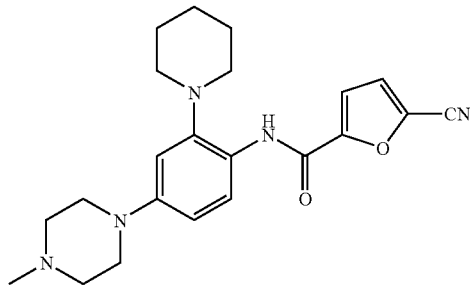

The procedure of Example 4, step (c) was followed using 304 mg (1.00 mmol) 1-methyl-4-(4-nitro-3-piperidin-1-yl-phenyl)-piperazine (as prepared in the previous step) and 304 mg of 10% palladium on carbon (50% by weight water) to prepare the intermediate aniline (4-(4-methyl-piperazin-1-yl)-2-piperidin-1-yl-phenylamine) along with 140 mg (1.02 mmol) of 5-cyanofuran-2-carboxylic acid (as prepared in Example 1), 178 µL (2.04 mmol) of oxalyl chloride, 10 µL of anh DMF, and 267 µL (1.53 mmol) of DIEA to perform the amide coupling. The resulting residue was chromatographed on a 20-g silica SPE column with 2-5% EtOH-dichloromethane to afford, after slow concentration from EtOAc-hexane (1:1), 232 mg (59%) of the title compound as a yellow solid: $^1$H-NMR (CDCl$_3$; 400 MHz): δ 9.53 (br s, 1H), 8.32 (d, 1H, J=8.9 Hz), 7.25 (d, 1H, J=3.7 Hz, partially obscured by CHCl$_3$ peak), 7.21 (d, 1H, J=3.7 Hz), 6.80 (d, 1H, J=2.7 Hz), 6.73 (dd, 1H, J=8.9, 2.7 Hz), 3.20 (m, 4H), 2.85 (m, 4H), 2.59 (m, 4H), 2.36 (s, 3H), 1.80 (m, 4H), and 1.65 (br m, 2H). Mass spectrum (ESI, m/z): Calcd. for C$_{22}$H$_{27}$N$_5$O$_2$, 394.2 (M+H), found 394.2.

Example 6

5-Cyano-furan-2-carboxylic acid (2-piperidin-1-yl-4-thiomorpholin-4-yl-phenyl)-amide

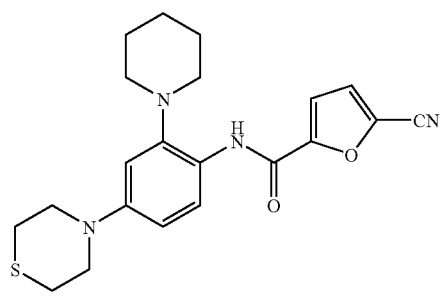

a) 4-(4-Nitro-3-piperidin-1-yl-phenyl)-morpholine

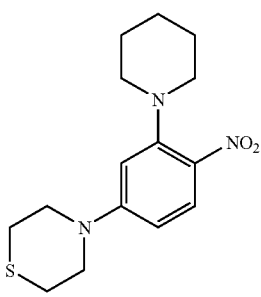

A mixture of 172 mg (0.715 mmol) 1-(5-chloro-2-nitrophenyl)-piperidine (as prepared in Example 4, step (a)) and 360 μL (3.58 mmol) of thiomorpholine were heated with stirring under Ar at 140° C. for 40 h. After cooling to RT, the mixture was poured into water (50 mL) and extracted with EtOAc (2×20 mL). The combined extracts were washed with water (3×50 mL) and brine (50 mL) and then dried (Na$_2$SO$_4$). Concentration and chromatography on a 10-g silica SPE column with 60% dichloromethane-hexane afforded 145 mg (66%) of the title compound as a yellow resin: Mass spectrum (ESI, m/z): Calcd. for C$_{15}$H$_{21}$N$_3$O$_2$S, 308.1 (M+H), found 308.1.

b) 5-Cyano-furan-2-carboxylic acid (2-piperidin-1-yl-4-thiomorpholin-4-yl-phenyl)-amide

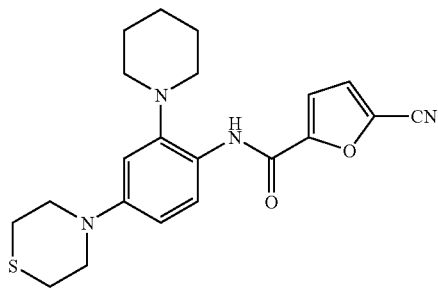

The title compound was prepared following the procedure of Example 4, step (c) using 86.4 mg (0.281 mmol) of 4-(4-nitro-3-piperidin-1-yl-phenyl)-morpholine (as prepared in the previous step), 86.4 mg of 10% palladium on carbon (50% by weight water), 38.5 mg (0.281 mmol) of 5-cyanofuran-2-carboxylic acid (as prepared in Example 1), 49.0 μL (0.562 mmol) of oxalyl chloride, and 73.5 μL (0.422 mmol) of DIEA. The resulting residue was chromatographed on a 10-g silica SPE column with 10% EtOAc-hexane to afford 75.3 mg (68%) of the title compound as a light yellow crystalline solid: $^1$H-NMR (CDCl$_3$; 400 MHz): δ 9.52 (br s, 1H), 8.31 (d, 1H, J=8.9 Hz), 7.26 (d, 1H, J=3.7 Hz, partially obscured by CHCl$_3$ peak), 7.22 (d, 1H, J=3.7 Hz), 6.76 (d, 1H, J=2.7 Hz), 6.70 (dd, 1H, J=8.9, 2.7 Hz), 3.49 (m, 4H), 2.84 (m, 4H), 2.77 (m, 4H), 1.81 (m, 4H), and 1.65 (br m, 2H). Mass spectrum (ESI, m/z): Calcd. for C$_{21}$H$_{24}$N$_4$O$_2$S, 397.2 (M+H), found 397.1.

Example 7

5-Cyano-furan-2-carboxylic acid [4-(1-oxo-1λ$^4$-thiomorpholin-4-yl)-2-piperidin-1-yl-phenyl]-amide

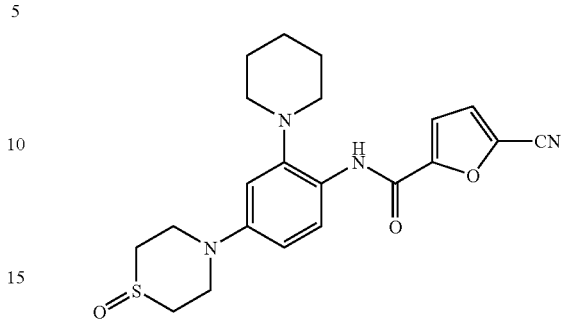

To a solution of 25.3 mg (0.0638 mmol) 5-cyano-furan-2-carboxylic acid (2-piperidin-1-yl-4-thiomorpholin-4-yl-phenyl)-amide (as prepared in Example 6, step (b)) in 2 mL of MeOH-MeCN (1:1) was added 15.0 mg (0.0702 mmol) of sodium periodate in 0.20 mL of water. After stirring for 1.5 h, an additional 4.1 mg (0.019 mmol) of sodium periodate was added. After stirring for 1.5 h, a final 9.5 mg (0.11 mmol) of sodium periodate was added and the mixture stirred for 24 h. The mixture was concentrated to near dryness, extracted with EtOAc (10 mL) and dried (Na$_2$SO$_4$). Concentration and chromatography on a 5-g silica SPE column with a gradient of 60-100% EtOAc-dichloromethane afforded 13.3 mg (51%) of the title compound as a light yellow solid: $^1$H-NMR (CDCl$_3$; 400 MHz): δ 9.51 (br s, 1H), 8.35 (d, 1H, J=8.9 Hz), ca. 7.2 (d, 1H, obscured by CHCl$_3$ peak), 7.23 (d, 1H, J=3.7 Hz), 6.81 (d, 1H, J=2.6 Hz), 6.77 (dd, 1H, J=8.9, 2.6 Hz), 3.94 (m, 2H), 3.51 (m, 2H), 2.91 (m, 4H), 2.85 (m, 4H), 1.81 (m, 4H), and 1.66 (br m, 2H). Mass spectrum (ESI, m/z): Calcd. for C$_{21}$H$_{24}$N$_4$O$_3$S, 413.2 (M+H), found 413.1.

Example 8

5-Cyano-furan-2-carboxylic acid [4-(1,1-dioxo-1λ$^6$-thiomorpholin-4-yl)-2-piperidin-1-yl-phenyl]-amide

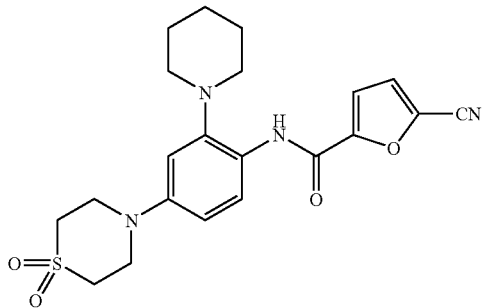

To a solution of 21.5 mg (0.0542 mmol) 5-cyano-furan-2-carboxylic acid (2-piperidin-1-yl-4-thiomorpholin-4-yl-phenyl)-amide (as prepared in Example 6, step (b)) in 0.6 mL of acetone-water (3:1) was added 22.0 mg (0.163 mmol) of 4-methyl-morpholine N-oxide followed by 25 μL (0.0039 mmol) of a solution of osmium tetroxide (4.0 wt % in water). After stirring for 18 h at RT, 3 mL of water was added and the mixture extracted with EtOAc (2×5 mL). The combined extracts were washed with brine (5 mL), dried (Na$_2$SO$_4$) and concentrated. Chromatography of the resulting residue on a 5-g silica SPE column with 5-6% EtOAc-dichloromethane afforded 19.1 mg (82%) of the title compound as a light yellow solid: ¹H-NMR (CDCl₃; 400 MHz): δ 9.48 (br s, 1H), 8.36 (d, 1H, J=8.9 Hz), ca. 7.28 (d, 1H, J=3.7 Hz), 7.23 (d, 1H, J=3.7 Hz), 6.77 (d, 1H, J=2.7 Hz), 6.73 (dd, 1H, J=8.9, 2.7 Hz), 3.80 (m, 4H), 3.14 (m, 4H), 2.84 (m, 4H), 1.82 (m, 4H), and 1.67 (br m, 2H). Mass spectrum (ESI, m/z): Calcd. for $C_{21}H_{24}N_4O_4S$, 429.2 (M+H), found 429.1.

Example 9

5-Cyano-furan-2-carboxylic acid [5-chloro-4-(4-methyl-piperazin-1-yl)-2-piperidin-1-yl-phenyl]-amide

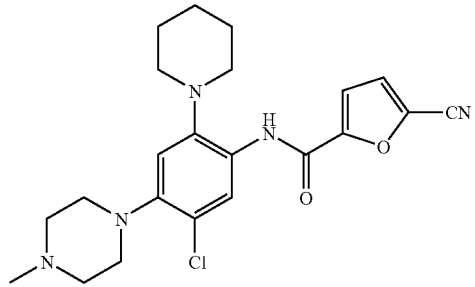

a) 1-(4,5-Dichloro-2-nitro-phenyl)-piperidine

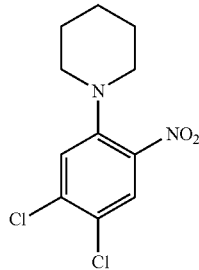

The procedure of Example 4, step (a) was followed using 2.10 g (10 mmol) of 1,2-dichloro-4-fluoronitrobenzene and 2.97 mL (30 mmol) of piperidine in 4 mL of EtOH except the reaction was stirred at RT for 4 h. Crystallization from hexane afforded 2.73 g (99%) of the title compound as a yellow-orange solid: Mass spectrum (ESI, ml/z): Calcd. for $C_{11}H_{12}Cl_2N_2O_2$, 275.0 (M+H), found 275.0.

b) 1-(2-Chloro-4-nitro-5-piperidin-1-yl-phenyl)-4-methyl-piperazine

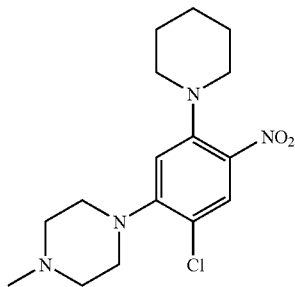

The procedure of Example 5, step (b) was followed using 968 mg (3.52 mmol) of 1-(4,5-dichloro-2-nitro-phenyl)-piperidine (as prepared in the previous step) and 1.95 mL (17.6 mmol) of 1-methylpiperazine. Crystallization from hexane afforded 997 mg (84%) of the title compound as a yellow-tan solid: Mass spectrum (ESI, m/z): Calcd. for $C_{16}H_{23}ClN_4O_2$, 339.2 (M+H), found 339.1.

c) 5-Cyano-furan-2-carboxylic acid [5-chloro-4-(4-methyl-piperazin-1-yl)-2-piperidin-1-yl-phenyl]-amide

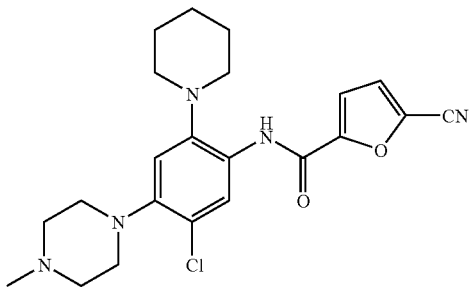

To 56.0 mg (0.165 mmol) of 1-(2-chloro-4-nitro-5-piperidin-1-yl-phenyl)-4-methyl-piperazine (as prepared in the previous step) in 3 mL of EtOH-water (2:1) was added 46.1 mg (0.825 mmol) of iron powder and 88.3 mg (1.65 mmol) of $NH_4Cl$ and the mixture refluxed under Ar for 15 h. The mixture was poured into EtOAc (6 mL), filtered (Celite) washing with EtOAc (2×2 mL), concentrated in vacuo and dissolved in anh THF (2 mL). The resulting aniline solution was placed under Ar and used immediately in the following reaction.

To 25.0 mg (0.182 mmol) of 5-cyanofuran-2-carboxylic acid (as prepared in Example 1) in 1.5 mL of anh dichloromethane under a $CaSO_4$ drying tube was added 23.8 μL (0.273 mmol) of oxalyl chloride followed by 5 μL of anh DMF. The solution was stirred for 25 min and then quickly concentrated in vacuo at 20-25° C. The residue was placed under high vacuum for only 2-3 min and then immediately placed under Ar, cooled to 0° C. in an ice bath, and treated with the aniline solution produced above followed by 60.4 μL (0.347 mmol) of DIEA. After stirring at RT for 30 min, the mixture was concentrated in vacuo and the resulting residue chromatographed on a 10-g silica SPE column with 1-3% EtOH-dichloromethane to afford 46.2 mg (65%) of the title compound as a light yellow solid: ¹H-NMR (CDCl₃; 400 MHz): δ 9.52 (br s, 1H), 8.49 (s, 1H), 7.23, 7.28 (AB q, 2H, J=3.7 Hz), 6.89 (s, 1H), 3.0-3.2 (br m, 4H), 2.82-2.84 (m, 4H), 2.6-2.7 (br m, 4H), 2.37 (s, 3H), 1.78-1.83 (m, 4H), and 1.6-1.7 (br m, 2H). Mass spectrum (ESI, m/z): Calcd. for $C_{22}H_{26}ClN_5O_2$, 428.2 (M+H), found 428.1.

Example 10

5-Cyano-furan-2-carboxylic acid [5-(4-methyl-piperazin-1-yl)-2-piperidin-1-yl-phenyl]-amide

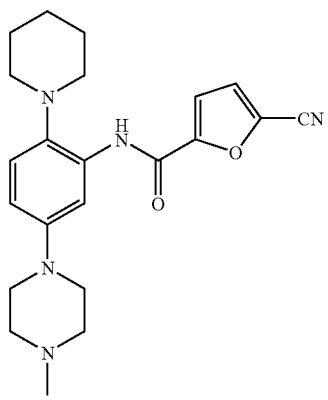

a) 3-Nitro-4-piperidin-1-yl-phenylamine

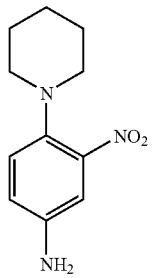

A solution of 1.00 g (6.41 mmol) of 4-fluoro-3-nitroaniline and 3.17 mL (32.1 mmol) of piperidine in 15 mL of acetonitrile under Ar was heated to reflux for 2 h. The mixture was cooled to RT, concentrated in vacuo, dissolved in EtOAc (60 mL) and washed with 1 M NaOH (2×50 mL), water (50 mL), brine (50 mL), and then dried ($Na_2SO_4$). Concentration afforded 1.40 g (99%) of the title compound as dark red crystals: $^1$H-NMR ($CDCl_3$; 400 MHz): δ 7.04 (d, 1H, J=8.6 Hz), 7.03 (d, 1H, J=2.8 Hz), 6.81 (dd, 1H, J=8.6, 2.8 Hz), 2.85-2.88 (m, 4H), 1.65-1.70 (m, 4H), and 1.51-1.55 (m, 2H).

b) 1-Methyl-4-(3-nitro-4-piperidin-1-yl-phenyl)-piperazine

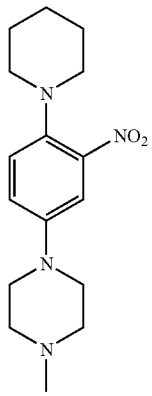

To a solution of 512 mg g (2.31 mmol) of 3-nitro-4-piperidin-1-yl-phenylamine (as prepared in the previous step) and 404 mg (2.10 mmol) of mechlorethamine hydrochloride in 15 mL of EtOH was added 1.45 g (10.5 mmol) of anh $K_2CO_3$ and the mixture heated to reflux under Ar for 48 h. The mixture was cooled to RT, concentrated in vacuo, extracted with EtOAc (3×20 mL) and the combined extracts filtered (Celite), and concentrated to a dark oil. Chromatography of the resulting residue on a 70-g silica SPE column with a gradient of 0-3% MeOH-dichloromethane afforded 456 mg (71%) of the title compound as a dark red solid: Mass spectrum (ESI, m/z): Calcd. for $C_{16}H_{24}N_4O_2$, 305.2 (M+H), found 305.1.

c) 5-Cyano-furan-2-carboxylic acid [5-(4-methyl-piperazin-1-yl)-2-piperidin-1-yl-phenyl]-amide

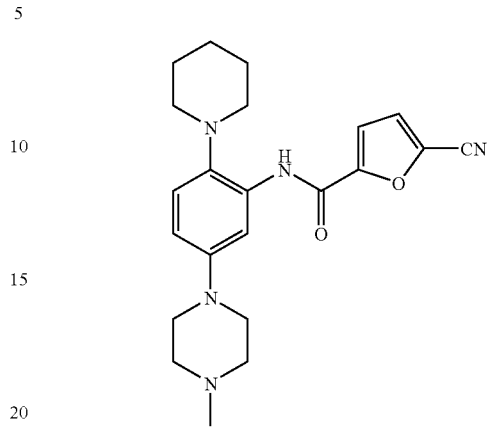

The title compound was prepared following the procedure of Example 4, step (c) using 28.1 mg (0.0923 mmol) of 1-methyl-4-(3-nitro-4-piperidin-1-yl-phenyl)-piperazine (as prepared in the previous step), 28 mg of 10% palladium on carbon (Degussa type E101-NE/W, 50% by weight water), 12.7 mg (0.0923 mmol) of 5-cyanofuran-2-carboxylic acid (as prepared in Example 1), 16.2 µL (0.185 mmol) of oxalyl chloride, and 24.1 µL (0.138 mmol) of DIEA. The resulting residue was chromatographed on a 10-g silica SPE column with 1-4% MeOH-dichloromethane to afford 25.8 mg (71%) of the title compound as a beige crystalline solid: $^1$H-NMR ($CDCl_3$; 400 MHz): δ 9.97 (br s, 1H), 8.18 (d, 1H, J=2.8 Hz), 7.23, 7.25 (AB q, 2H, J=3.7 Hz), 7.11 (d, 1H, J=8.7 Hz), 6.67 (dd, 1H, J=8.7, 2.8 Hz), 3.22-3.25 (m, 4H), 2.75-2.85 (m, 4H), 2.56-2.58 (m, 4H), 2.35 (s, 3H), 1.76-1.81 (m, 4H), and 1.5-1.7 (br m, 2H). Mass spectrum (ESI, m/z): Calcd. for $C_{22}H_{27}N_5O_2$, 394.2 (M+H), found 394.2.

Example 11

5-Cyano-furan-2-carboxylic acid (5-morpholin-4-yl-2-piperidin-1-yl-phenyl)-amide

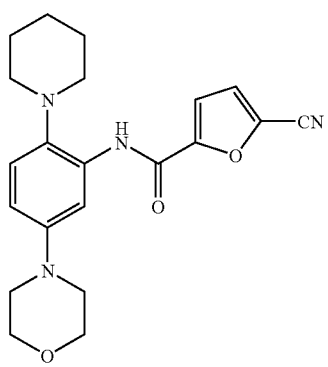

a) 4-(3-Nitro-4-piperidin-1-yl-phenyl)-morpholine

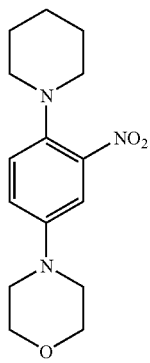

The title compound was prepared following the procedure of Example 10, step (b) using 152 mg (0.687 mmol) of 3-nitro-4-piperidin-1-yl-phenylamine (as prepared in Example 10, step (a)), 78.6 mg (0.625 mmol) of 2-bromoethyl ether and 433 mg (3.13 mmol) of anh $K_2CO_3$ except the mixture was heated to reflux in 2 mL of toluene for 20 h. Chromatography on a 10-g silica SPE column with 40% $Et_2O$-hexane afforded 128 mg (70%) of the title compound as a dark orange resin: Mass spectrum (ESI, m/z): Calcd. for $C_{15}H_{21}N_3O_2$, 292.2 (M+H), found 292.1.

b) 5-Cyano-furan-2-carboxylic acid (5-morpholin-4-yl-2-piperidin-1-yl-phenyl)-amide

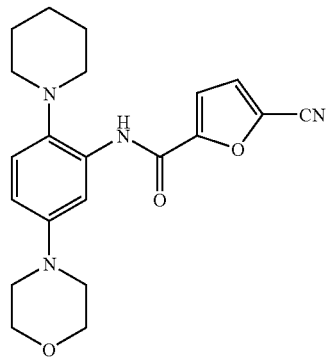

The title compound was prepared following the procedure of Example 5, step (b) using 76.7 mg (0.318 mmol) of 4-(3-nitro-4-piperidin-1-yl-phenyl)-morpholine (as prepared in the previous step), 50 mg of 10% palladium on carbon (50% by weight water), 43.6 mg (0.318 mmol) of 5-cyanofuran-2-carboxylic acid (as prepared in Example 1), 55.5 µL (0.636 mmol) of oxalyl chloride, and 83.1 µL (0.477 mmol) of DIEA. The resulting residue was chromatographed on a 10-g silica SPE column with 15-25% EtOAc-hexane to afford 54.9 mg (45%) of the title compound as a light yellow solid: $^1$H-NMR (CDCl$_3$; 400 MHz): δ 9.97 (br s, 1H), 8.17 (d, 1H, J=2.8 Hz), 7.23, 7.26 (AB q, 2H, J=3.7 Hz), 7.13 (d, 1H, J=8.7 Hz), 6.66 (dd, 1H, J=8.7, 2.8 Hz), 3.84-3.87 (m, 4H), 23.17-3.19 (m, 4H), 2.75-2.85 (m, 4H), 1.77-1.82 (m, 4H), and 1.5-1.7 (br m, 2H). Mass spectrum (ESI, m/z): Calcd. for $C_{21}H_{24}N_4O_3$, 381.2 (M+H), found 381.2.

Example 12

5-Cyano-furan-2-carboxylic acid [2-(4-methyl-piperidin-1-yl)-4-morpholin-4-yl-phenyl]-amide

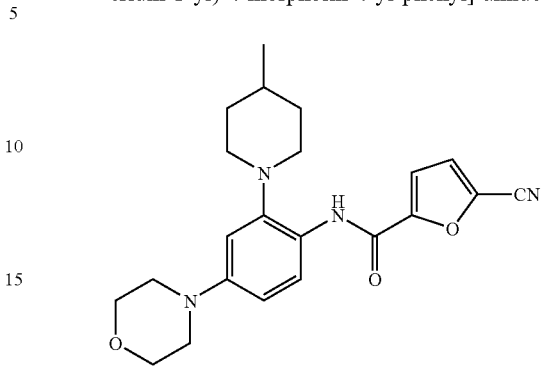

a) 1-(5-Chloro-2-nitro-phenyl)-4-methyl-piperidine

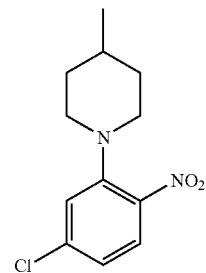

The procedure of Example 4, step (a) was followed using 0.950 g (5.43 mmol) of 4-chloro-2-fluoronitrobenzene and 1.93 mL (16.3 mmol) of 4-methylpiperidine in 10 mL of EtOH to afford 1.37 g (99%) of the title compound as an orange oil which crystallized on standing: Mass spectrum (ESI, m/z): Calcd. for $C_{12}H_{15}ClN_2O_2$, 255.1 (M+H), found 255.0.

b) 4-[3-(4-Methyl-piperidin-1-yl)-4-nitro-phenyl]-morpholine

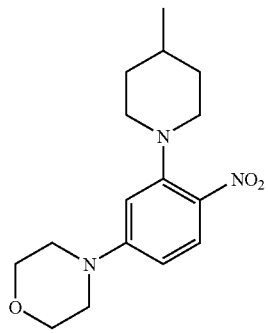

The procedure of Example 4, step (b) was followed using 304 mg (1.19 mmol) of 1-(5-chloro-2-nitro-phenyl)-4-methyl-piperidine (as prepared in the previous step) and 519 µL (5.95 mmol) of morpholine to afford 363 mg (106%) of the title compound as a yellow resin: Mass spectrum (ESI, m/z): Calcd. for $C_{16}H_{23}N_3O_3$, 306.2 (M+H), found 306.1.

c) 5-Cyano-furan-2-carboxylic acid [2-(4-methyl-piperidin-1-yl)-4-morpholin-4-yl-phenyl]-amide

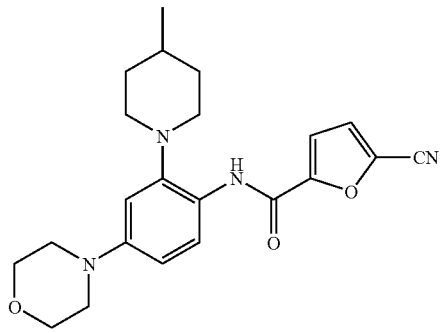

The procedure of Example 4, step (c) was followed using 101 mg (0.331 mmol) of 4-[3-(4-methyl-piperidin-1-yl)-4-nitro-phenyl]-morpholine (as prepared in the previous step) and 40 mg of 10% palladium on carbon (50% by weight water) in 5 mL THF to prepare the corresponding aniline. However, 5-cyanofuran-2-carboxylic acid N-hydroxysuccinimide ester was used to acylate the aniline instead of 5-cyanofuran-2-carbonyl chloride. (5-cyanofuran-2-carboxylic acid N-hydroxysuccinimide ester was previously prepared from 5-cyanofuran-2-carboxylic acid (as prepared in Example 1), oxalyl chloride, N-hydroxysuccinimide and DIEA following the procedure of Example 4, step (c).) The aniline prepared above in 3.0 mL of anh dichloromethane was treated with 77.5 mg (0.331 mmol) of 5-cyanofuran-2-carboxylic acid N-hydroxysuccinimide ester. After stirring for 1 h, an additional 77.5 mg (0.331 mmol) of 5-cyanofuran-2-carboxylic acid N-hydroxysuccinimide ester was added. After 3 h, a final 77.5 mg (0.331 mmol) of 5-cyanofuran-2-carboxylic acid N-hydroxysuccinimide ester was added and the mixture stirred 18 h. Concentration in vacuo and chromatography on a 10-g silica SPE column with 2-4% EtOAc-dichloromethane afforded 85.1 mg (65%) of the title compound as a light yellow solid: $^1$H-NMR (CDCl$_3$; 400 MHz): δ 9.60 (br s, 1H), 8.32 (d, 1H, J=8.9 Hz), 7.22, 7.26 (AB q, 2H, J=3.7 Hz), 6.78 (d, 1H, J=2.7 Hz), 6.71 (dd, 1H, J=8.9, 2.7 Hz), 3.86-3.88 (m, 4H), 3.13-3.15 (m, 4H), 2.98-3.01 (m, 2H), 2.70-2.15 (m, 2H), 1.83-1.86 (m, 2H), 1.5-1.7 (br m, 1H) and 1.43-1.53 (m, 2H). Mass spectrum (ESI, m/z): Calcd. for C$_{22}$H$_{26}$N$_4$O$_3$, 395.2 (M+H), found 395.2.

Example 13

5-Cyano-furan-2-carboxylic acid [4-(4-methyl-piperazin-1-yl)-2-(4-methyl-piperidin-1-yl)-phenyl]-amide

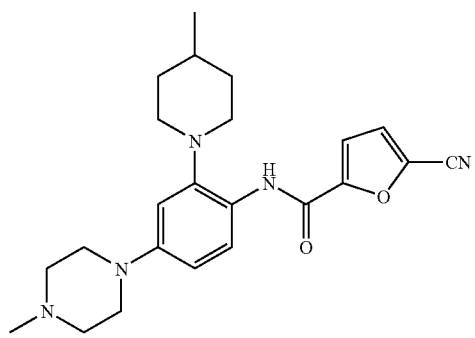

a) 1-Methyl-4-[3-(4-methyl-piperidin-1-yl)-4-nitro-phenyl]-piperazine

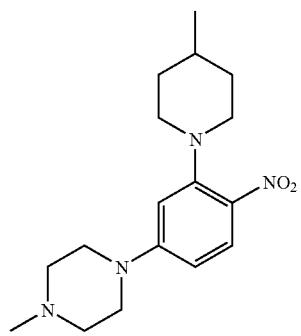

The procedure of Example 4, step (b) was followed using 150 mg (0.589 mmol) of 1-(5-chloro-2-nitro-phenyl)-4-methyl-piperidine (as prepared in the Example 12, step (a)) and 327 µL (2.95 mmol) of 1-methylpiperazine at 142° C. for 21 h to afford 189 mg (100%) of the title compound as a yellow semisolid: Mass spectrum (ESI, m/z): Calcd. for C$_{16}$H$_{24}$N$_4$O$_2$, 319.2 (M+H), found 319.1.

b) 5-Cyano-furan-2-carboxylic acid [4-(4-methyl-piperazin-1-yl)-2-(4-methyl-piperidin-1-yl)-phenyl]-amide

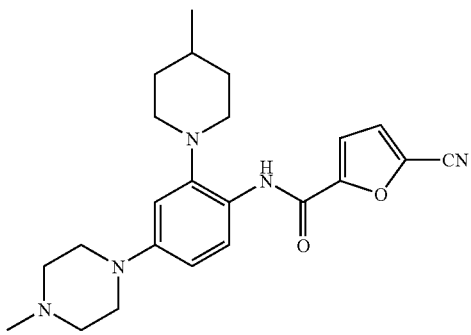

The procedure of Example 4, step (c) was followed using 50.2 mg (0.158 mmol) of 1-methyl-4-[3-(4-methyl-piperidin-1-yl)-4-nitro-phenyl]-piperazine (as prepared in the previous step), 20 mg of 10% palladium on carbon (50% by weight water), 22.8 mg (0.166 mmol) of 5-cyanofuran-2-carboxylic acid (as prepared in Example 1), 29.0 µL (0.332 mmol) of oxalyl chloride, and 57.8 µL (0.332 mmol) of DIEA. Chromatography on a 5-g silica SPE column with 0.5-3% MeOH-dichloromethane afforded 34.8 mg (54%) of the title compound as a light yellow solid: $^1$H-NMR (CDCl$_3$; 400 MHz): o 9.59 (br s, 1H), 8.33 (d, 1H, J=8.9 Hz), 7.21, 7.25 (AB q, 2H, J=3.7 Hz, partially obscured by CHCl$_3$ peak), 6.78 (d, 1H, J=2.7 Hz), 6.74 (dd, 1H, J=8.9, 2.7 Hz), 3.35-3.55 (m, 4H), 2.95-3.05 (m, 4H), 2.72-2.75 (m, 4H), 2.67 (br s, 3H), 1.83-1.87 (m, 2H), 1.45-1.65 (br m, 1H), 1.43-1.53 (m, 2H) and 1.07 (d, 3H, J=6.2 Hz), Mass spectrum (ESI, m/z): Calcd. for C$_{23}$H$_{29}$N$_5$O$_2$, 408.2 (M+H), found 408.3.

Example 14

4-[4-[(5-Cyano-furan-2-carbonyl)-amino]-3-(4-methyl-piperidin-1-yl)-phenyl]-piperazine-1-carboxylic acid benzyl ester

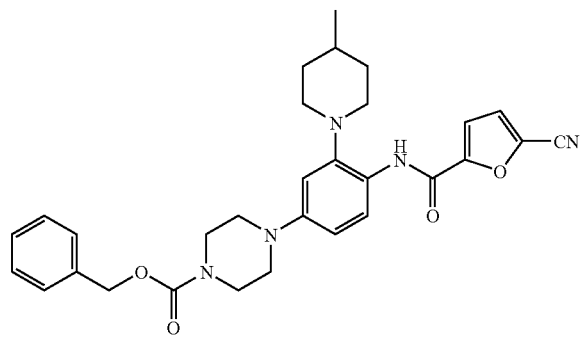

a) 4-[3-(4-Methyl-piperidin-1-yl)-4-nitro-phenyl]-piperazine-1-carboxylic acid benzyl ester

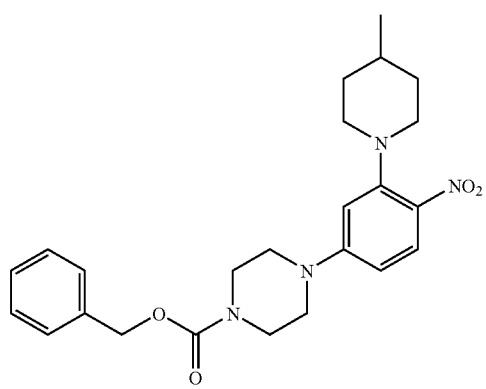

The procedure of Example 4, step (b) was followed using 400 mg (1.57 mmol) of 1-(5-chloro-2-nitro-phenyl)-4-methyl-piperidine (as prepared in the Example 12, step (a)) and 910 mg (4.71 mmol) of benzyl 1-piperazinecarboxylate (except that 549 µL (4.71 mmol) of 2,6-lutidine was also added) to afford, after chromatography on a 70-g silica SPE column with 40% EtOAc-hexane, 178 mg (45%) of unreacted 1-(5-chloro-2-nitro-phenyl)-4-methyl-piperidine and 245 mg (64% based on recovered starting material) of the title compound as a yellow resin: Mass spectrum (ESI, m/z): Calcd. for $C_{24}H_{30}N_4O_4$, 439.2 (M+H), found 439.2.

b) 4-[4-[(5-Cyano-furan-2-carbonyl)-amino]-3-(4-methyl-piperidin-1-yl)-phenyl]-piperazine-1-carboxylic acid benzyl ester

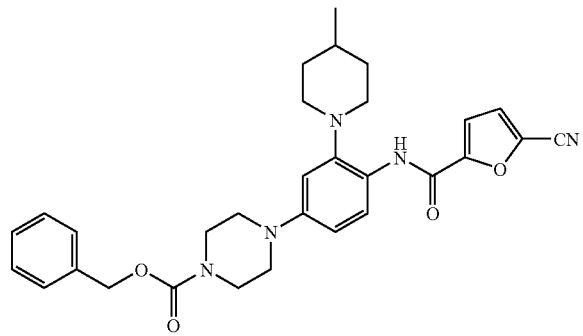

A procedure similar to Example 9, step (c) was followed using 153 mg (0.349 mmol) of 4-[3-(4-methyl-piperidin-1-yl)-4-nitro-phenyl]-piperazine-1-carboxylic acid benzyl ester (as prepared in the previous step), 97.7 mg (1.75 mmol) of iron powder, 187 mg (3.49 mmol) of ammonium chloride in 10 mL of EtOH-water (2:1) to afford 104 mg (73%) of the corresponding aniline after chromatography on silica with 4-12% EtOAc-dichloromethane. The aniline (100 mg) together with 33.6 mg (0.245 mmol) of 5-cyanofuran-2-carboxylic acid (as prepared in Example 1), 42.7 µL (0.490 mmol) of oxalyl chloride, and 64.1 µL (0.368 mmol) of DIEA afforded, after chromatography on a 20-g silica SPE column with 2% EtOAc-dichloromethane, 118 mg (91%) of the title compound as a light yellow solid: $^1$H-NMR (CDCl$_3$; 400 MHz): δ 9.59 (br s, H), 8.31 (d, 1H, J=8.9 Hz), 7.33-7.38 (m, 5H), 7.21, 7.24 (AB q, 2H, J=3.7 Hz), 6.79 (d, 1H, J=2.6 Hz), 6.72 (dd, 1H, J=8.9, 2.6 Hz), 5.17 (s, 2H), 3.66-3.69 (m, 4H), 3.12 (br s, 4H), 2.97-3.00 (m, 2H), 2.69-2.75 (m, 2H), 1.83-1.86 (m, 2H), 1.50-1.65 (m, 1H), 1.46-1.52 (m, 2H) and 1.07 (d, 3H, J=6.2 Hz). Mass spectrum (ESI, m/z): Calcd. for $C_{30}H_{33}N_5O_4$, 528.3 (M+H), found 528.1.

Example 15

4-[4-[(5-Cyano-furan-2-carbonyl)-amino]-3-(4-methyl-piperidin-1-yl)-phenyl]-piperazine-1-carboxylic acid tert-butyl ester

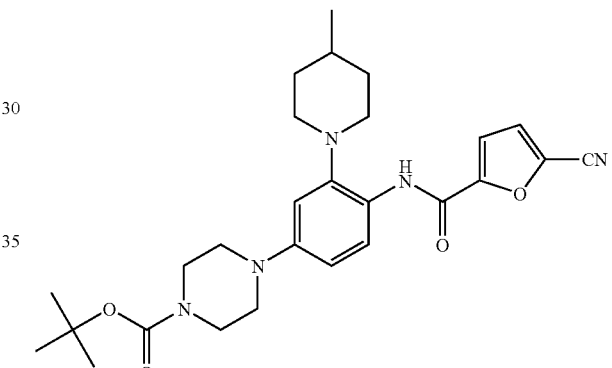

a) 1-[3-(4-Methyl-piperidin-1-yl)-4-nitro-phenyl]-piperazine

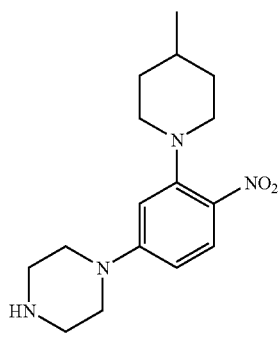

The procedure of Example 4, step (b) was followed using 460 mg (1.81 mmol) of 1-(5-chloro-2-nitro-phenyl)-4-methyl-piperidine (as prepared in the Example 12, step (a)) and 3.12 g (36.2 mmol) of piperazine for 24 h to afford, after chromatography on a 20-g silica SPE column with 0-10% MeOH-dichloromethane, 518 mg (94%) of the title compound as an orange resin: Mass spectrum (ESI, m/z): Calcd. for $C_{16}H_{24}N_4O_2$, 305.2 (M+H), found 305.1.

b) 4-[3-(4-Methyl-piperidin-1-yl)-4-nitro-phenyl]-piperazine-1-carboxylic acid tert-butyl ester

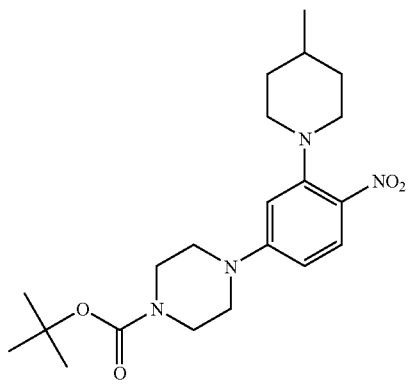

A solution of 235 mg (0.772 mmol) of 1-[3-(4-methyl-piperidin-1-yl)-4-nitro-phenyl]-piperazine (as prepared in the previous step) and 253 mg (1.16 mmol) of di-t-butyl dicarbonate in 8 mL of THF-dichloromethane (1:1) was stirred at RT for 26 h and then concentrated in vacuo. Chromatography of the resulting oil on a 10-g silica SPE column with 50% dichloromethane-hexane followed by 2-5% EtOAc-dichloromethane afforded 300 mg (96%) of the title compound as a crystalline yellow solid: Mass spectrum (ESI, m/z): Calcd. for $C_{21}H_{32}N_4O_4$, 405.2 (M+H), found 405.1.

c) 4-[4-[(5-Cyano-furan-2-carbonyl)-amino]-3-(4-methyl-piperidin-1-yl)-phenyl]-piperazine-1-carboxylic acid tert-butyl ester

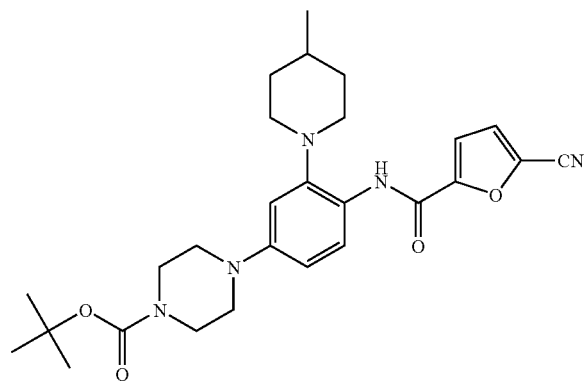

The procedure of Example 4, step (c) was followed using 145 mg (0.358 mmol) of 4-[3-(4-methyl-piperidin-1-yl)-4-nitro-phenyl]-piperazine-1-carboxylic acid tert-butyl ester (as prepared in the previous step), 70 mg of 10% palladium on carbon (50% by weight water), 49.1 mg (358 mmol) of 5-cyanofuran-2-carboxylic acid (as prepared in Example 1), 62.4 µL (0.716 mmol) of oxalyl chloride, and 93.6 µL (0.537 mmol) of DIEA. Chromatography on a 20-g silica SPE column with 20-40% EtOAc-dichloromethane followed by recrystallization from EtOAc-hexane afforded 156 mg (88%) of the title compound as a light yellow solid: $^1$H-NMR (CDCl$_3$; 400 MHz): δ 9.60 (br s, 1H), 8.32 (d, 1H, J=8.9 Hz), 7.22, 7.24 (AB q, 2H, J=3.7 Hz), 6.79 (d, 1H, J=2.6 Hz), 6.72 (dd, 1H, J=8.9, 2.6 Hz), 3.58-3.60 (m, 4H), 3.10 (br s, 4H), 2.97-3.00 (m, 2H), 2.70-2.75 (m, 2H), 1.82-1.85 (m, 2H), 1.55-1.65 (m, 1H), 1.49 (s, 9H), 1.45-1.55 (m, 2H, partially obscured by t-Bu peak) and 1.07 (d, 3H, J=6.2 Hz). Mass spectrum (ESI, m/z): Calcd. for $C_{28}H_{37}N_5O_4$, 494.3 (M+H), found 494.1.

Example 16

5-Cyano-furan-2-carboxylic acid [2-(4-methyl-piperidin-1-yl)-4-piperazin-1-yl-phenyl]-amide tris(trifluoroacetic acid salt)

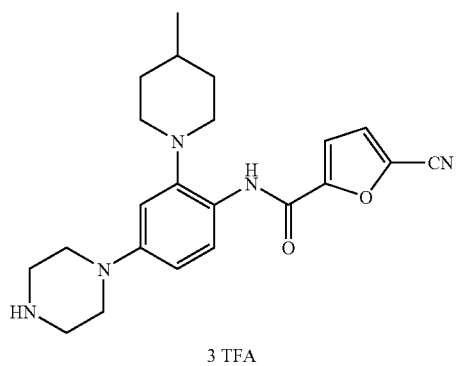

3 TFA

To 34.2 mg (0.0693 mmol) of 4-[4-[(5-cyano-furan-2-carbonyl)-amino]-3-(4-methyl-piperidin-1-yl)-phenyl]-piperazine-1-carboxylic acid tert-butyl ester (as prepared in Example 15, step (c)) was added 4 mL of trifluoroacetic acid-dichloromethane-water (10:30:1) and the solution stirred for 30 min at RT followed by immediate concentration in vacuo at 20° C. The resulting glass was crystallized from CHCl$_3$ at −78° C. followed by concentration from EtOAc-dichloromethane (1:1, 2×2 mL) to afforded 41.7 mg (82%) of the title compound as a cream-colored solid. The ratio of protons in the $^1$H-NMR relative and the ratio of fluorines in the $^{19}$F-NMR of the product relative to the protons and fluorines in an external $^1$H/$^{19}$F standard indicated the presence of three TFA molecules per product molecule: Mass spectrum (ESI, m/z): Calcd. for $C_{22}H_{27}N_5O_2$, 394.2 (M+H), found 394.2.

Example 17

5-Cyano-furan-2-carboxylic acid [4-(4-acetyl-piperazin-1-yl)-2-(4-methyl-piperidin-1-yl)-phenyl]-amide

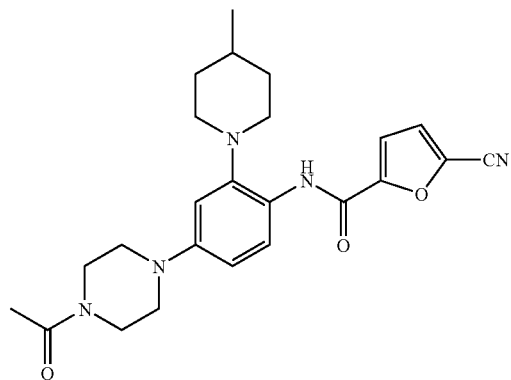

To 40.0 mg (0.0546 mmol) of 5-cyano-furan-2-carboxylic acid [2-(4-methyl-piperidin-1-yl)-4-piperazin-1-yl-phenyl]-amide tris(trifluoroacetic acid salt) (as prepared in Example 16) suspended in 2 mL of anh THF was added 6.2 μL (0.0655 mmol) of acetic anhydride followed by 47.6 μL (0.716 mmol) of DIEA. After stirring for 20 min at RT, the mixture was poured into satd aq NaHCO₃ (20 mL) and extracted with EtOAc (20 mL). The extract was dried (Na₂SO₄) and concentrated in vacuo and the resulting solid was chromatographed on a 2-g silica SPE column with 25-40% EtOAc-dichloromethane to afford 22.0 mg (92%) of the title compound as a crystalline yellow solid: ¹H-NMR (CDCl₃; 400 MHz): δ 9.59 (br s, 1H), 8.32 (d, 1H, J=8.9 Hz), 7.22, 7.25 (AB q, 2H, J=3.7 Hz, partially obscured by CHCl₃ peak), 6.79 (d, 1H, J=2.6 Hz), 6.72 (dd, 1H, J=8.9, 2.6 Hz), 3.77-3.80 (m, 2H), 3.62-3.64 (m, 2H), 3.11-3.17 (m, 4H), 2.98-3.01 (m, 2H), 2.73-2.76 (m, 2H), 2.15 (s, 3H), 1.83-1.86 (m, 2H), 1.52-1.62 (m, 1H), 1.46-1.56 (m, 2H) and 1.07 (d, 3H, J=6.2 Hz). Mass spectrum (ESI, m/z): Calcd. for $C_{24}H_{29}N_5O_3$, 436.2 (M+H), found 436.2.

Example 18

5-Cyano-furan-2-carboxylic acid [4-(4-methanesulfonyl-piperazin-1-yl)-2-(4-methyl-piperidin-1-yl)-phenyl]-amide

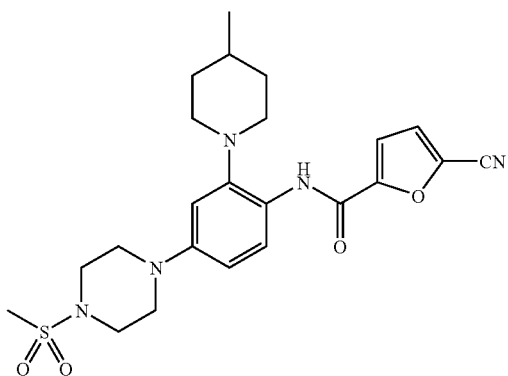

The procedure of Example 17 was followed using 40.0 mg (0.0546 mmol) of 5-cyano-furan-2-carboxylic acid [2-(4-methyl-piperidin-1-yl)-4-piperazin-1-yl-phenyl]-amide tris(trifluoroacetic acid salt) (as prepared in Example 16), 7.6 μL (0.0655 mmol) of is methanesulfonyl chloride and 47.6 μL (0.716 mmol) of DIEA. Chromatography on a 2-g silica SPE column with 5-10% EtOAc-dichloromethane followed by concentration from EtOAc-hexane (1:1, 2 mL) afforded 23.3 mg (91%) of the title compound as a crystalline yellow solid: ¹H-NMR (CDCl₃; 400 MHz): δ 9.59 (br s, 1H), 8.33 (d, 1H, J=8.8 Hz), 7.22, 7.25 (AB q, 2H, J=3.7 Hz, partially obscured by CHCl₃ peak), 6.79 (d, 1H, J=2.7 Hz), 6.73 (dd, 1H, J=8.8, 2.7 Hz), 3.39-3.41 (m, 4H), 3.25-3.27 (m, 4H), 2.98-3.01 (m, 2H), 2.84 (s, 3H), 2.70-2.76 (m, 2H), 1.83-1.87 (m, 2H), 1.50-1.65 (m, 1H), 1.42-1.58 (m, 2H) and 1.08 (d, 3H, J=6.2 Hz). Mass spectrum (ESI, m/z): Calcd. for $C_{23}H_{29}N_5O_4S$, 472.2 (M+H), found 472.2.

Example 19

Carbonic acid tert-butyl ester 2-{4-[4-[(5-cyano-furan-2-carbonyl)-amino]-3-(4-methyl-piperidin-1-yl)-phenyl]-piperazin-1-yl}-ethyl ester

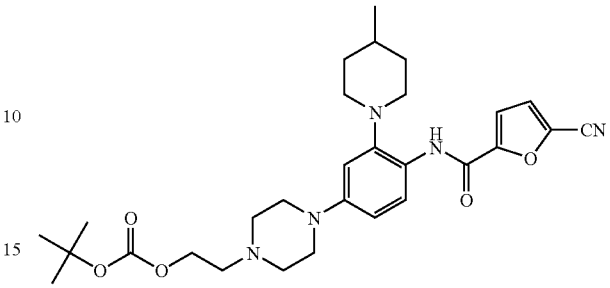

a) 2-{4-[3-(4-Methyl-piperidin-1-yl)-4-nitro-phenyl]-piperazin-1-yl}-ethanol

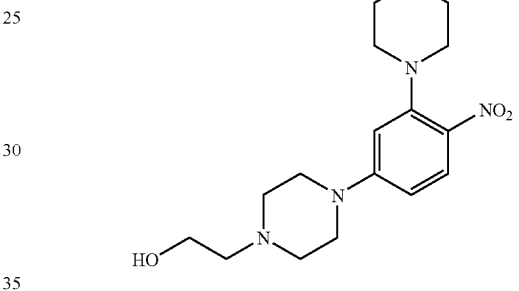

The procedure of Example 4, step (b) was followed using 810 mg (3.18 mmol) of 1-(5-chloro-2-nitro-phenyl)-4-methyl-piperidine (as prepared in the Example 12, step (a)) and 1.95 mL (15.9 mmol) of 1-(2-hydroxyethyl)piperazine for 14 h to afford 1.11 g (100%) of the title compound as a yellow solid: Mass spectrum (ESI, m/z): Calcd. for $C_{18}H_{28}N_4O_3$, 349.2 (M+H), found 349.2.

b) Carbonic acid tert-butyl ester 2-{4-[3-(4-methyl-piperidin-1-yl)-4-nitro-phenyl]-piperazin-1-yl}-ethyl ester

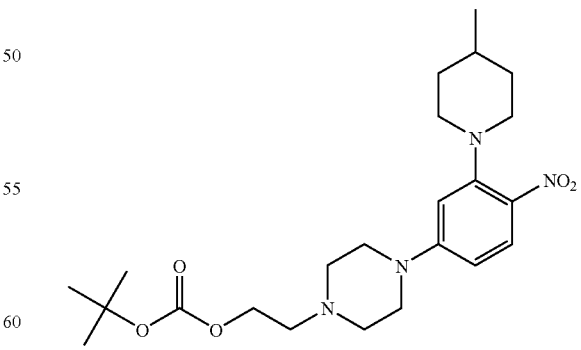

A solution of 320 mg (0.919 mmol) of 2-{4-[3-(4-methyl-piperidin-1-yl)-4-nitro-phenyl]-piperazin-1-yl}-ethanol (as prepared in the previous step), 240 mg (1.10 mmol) of di-t-butyl dicarbonate and 9.0 mg (0.074 mmol) of 4-(dimethylamino)pyridine in 8 mL of THF was stirred at 50° C. for 0.5 h and then concentrated in vacuo. Chromatography of the resulting oil on a 20-g silica SPE column with 0-10% EtOAc-dichloromethane afforded 342 mg (83%) of the title compound as a yellow resin: Mass spectrum (ESI, m/z): Calcd. for $C_{23}H_{36}N_4O_5$, 449.3 (M+H), found 449.1.

c) Carbonic acid tert-butyl ester 2-{4-[4-[(5-cyano-furan-2-carbonyl)-amino]-3-(4-methyl-piperidin-1-yl)-phenyl]-piperazin-1-yl}-ethyl ester

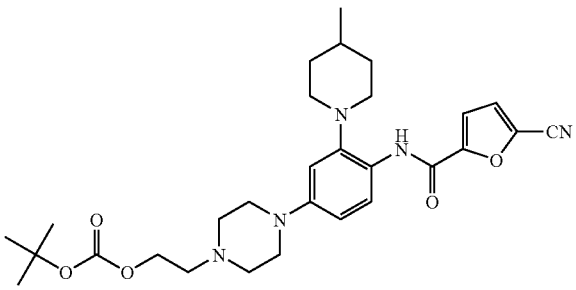

The procedure of Example 4, step (c) was followed using 156 mg (0.348 mmol) of carbonic acid tert-butyl ester 2-{4-[3-(4-methyl-piperidin-1-yl)-4-nitro-phenyl]-piperazin-1-yl}-ethyl ester (as prepared in the previous step), 78 mg of 10% palladium on carbon (50% by weight water), 52.5 mg (383 mmol) of 5-cyanofuran-2-carboxylic acid (as prepared in Example 1), 50.1 µL (0.575 mmol) of oxalyl chloride, and 121 µL (0.696 mmol) of DIEA. Chromatography on a 10-g silica SPE column with 5-20% EtOAc-dichloromethane afforded 176 mg (94%) of the title compound as a light yellow solid: $^1$H-NMR (CDCl$_3$; 400 MHz): δ 9.60 (br s, 1H), 8.29 (d, 1H, J=8.9 Hz), 7.21, 7.24 (AB q, 2H, J=3.7 Hz), 6.79 (d, 1H, J=2.6 Hz), 6.71 (dd, 1H, J=8.9, 2.6 Hz), 4.23 (t, 2H, J=5.8 Hz), 3.16-3.19 (m, 4H), 2.97-3.00 (m, 2H), 2.67-2.75 (m, 8H), 1.82-1.84 (m, 4H), 1.50-1.65 (m, 1H), 1.46-1.58 (m, 2H, partially obscured by t-Bu peak), 1.49 (s, 9H), and 1.07 (d, 3H, J=6.2 Hz). Mass spectrum (ESI, m/z): Calcd. for $C_{29}H_{39}N_5O_5$, 538.3 (M+H) and 438.2 (M-BOC+2H), found 538.2, 438.2.

Example 20

5-Cyano-furan-2-carboxylic acid [4-[4-(2-hydroxy-ethyl)-piperazin-1-yl]-2-(4-methyl-piperidin-1-yl)-phenyl]-amide trifluoroacetic acid salt

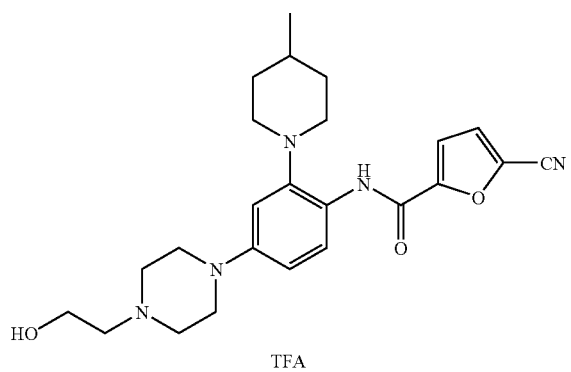

To 92.2 mg (0.172 mmol) of carbonic acid tert-butyl ester 2-{4-[4-[(5-cyano-furan-2-carbonyl)-amino]-3-(4-methyl-piperidin-1-yl)-phenyl]-piperazin-1-yl}-ethyl ester (as prepared in Example 19, step (c)) was added 2 mL of trifluoroacetic acid-dichloromethane-water (20:5:1) and the solution stirred for 2 h at RT followed by concentration in vacuo. The resulting resin was crystallized from hot CHCl$_3$ to afford 154 mg pale yellow crystals. This material in 8 mL of EtOAc was treated with 3 g K$_2$CO$_3$ and water (2 mL) and stirred for 30 min. Anh Na$_2$SO$_4$ was added, the mixture filtered and the filtrate dried over anh K$_2$CO$_3$ and concentrated in vacuo to afford the title compound as a yellow solid. The ratio of protons in the $^1$H-NMR relative and the ratio of fluorines in the $^{19}$F-NMR of the product relative to the protons and fluorines in an external $^1$H/$^{19}$F standard indicated the presence of 1.4 TFA molecules per product molecule: $^1$H-NMR (DMSO-d$_6$; 400 MHz): δ 9.58 (br s, 1H), 8.91 (d, 1H, J=8.9 Hz), 7.79 (d, 1H, J=3.8 Hz), 7.44 (d, 1H, J=3.8 Hz), 6.80 (d, 1H, J=2.6 Hz), 6.69 (dd, 1H, J=8.9, 2.6 Hz), 4.47 (t, 1H, J=5.3 Hz), 3.51-3.55 (m, 2H), 3.09-3.12 (m, 4H), 2.92-2.95 (m, 2H), 2.68-2.74 (m, 2H), 2.53-2.55 (m, 4H), 2.43 (t, 2H, J=6.2 Hz), 1.75-1.77 (m, 2H), 1.48-1.54 (m, 1H), 1.31-1.41 (m, 2H), and 0.99 (d, 3H, J=6.4 Hz). Mass spectrum (ESI, m/z): Calcd. for $C_{24}H_{31}N_5O_3$, 438.2 (M+H), found 438.2.

Example 21

5-Cyano-furan-2-carboxylic acid [5-fluoro-4-(4-methyl-piperazin-1-yl)-2-(4-methyl-piperidin-1-yl)-phenyl]-amide

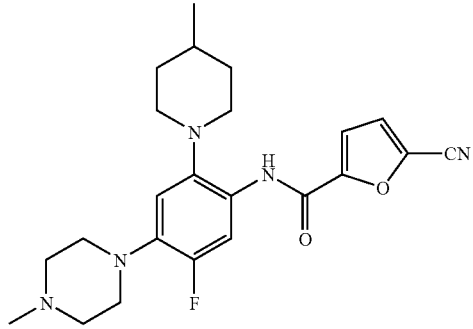

a) 1-(5-Chloro-4-fluoro-2-nitro-phenyl)-4-methyl-piperidine and 1-(5-chloro-2-fluoro-4-nitro-phenyl)-4-methyl-piperidine

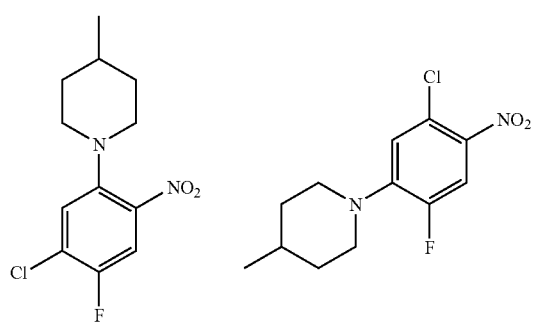

The procedure of Example 4, step (a) was followed using 575 mg (2.74 mmol) of 2,4-dichloro-5-fluoronitrobenzene (Oakwood) and 280 µL (2.39 mmol) of 1-methylpiperidine in 4 µL of EtOH except the reaction was stirred at 78° C. for 16 h to give 670 mg of a ca. 1:1:1 mixture by $^1$H-NMR of 2,4-dichloro-5-fluoronitrobenzene and the two title compounds. Chromatography on a silica gel with 20-40% dichloromethane-hexane afforded pure analytical samples of each product which were characterized by 2-dimensional $^{13}$C—$^1$H correlation NMR spectra to assign carbons and then by fluorine-carbon couplings to determine the higher $R_f$ product to be 1-(5-chloro-4-fluoro-2-nitro-phenyl)-4-methyl-piperidine: Mass spectrum (ESI, m/z): Calcd. for $C_{12}H_{14}ClFN_2O_2$, 273.1 (M+H), found 273.0, and the lower $R_f$ product to be 1-(5-chloro-2-fluoro-4-nitro-phenyl)-4-methyl-piperidine: Mass spectrum (ESI, m/z): Calcd. for $C_{11}H_{12}Cl_2N_2O_2$, 275.0 (M+H), found 273.1. Fractions containing the higher $R_f$ product (60% purity by $^1$H-NMR) were carried on to the following reaction without further purification.

b) 1-[2-Fluoro-5-(4-methyl-piperidin-1-yl)-4-nitro-phenyl]-4-methyl-piperazine

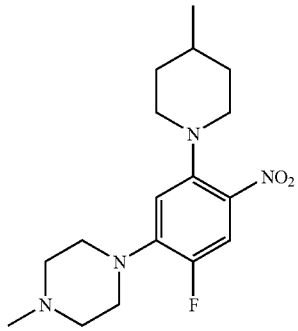

The procedure of Example 4, step (b) was followed using 88 mg (0.19 mmol based on 60% purity by $^1$H-NMR) of 1-(5-chloro-4-fluoro-2-nitro-phenyl)-4-methyl-piperidine (as prepared in the previous step) and 105 μL (0.950 mmol) of 1-methylpiperazine at 150° C. for 16 h. Chromatography on a 10-g silica SPE column with 24% MeOH-dichloromethane afforded 60 mg (94%) of the title compound as a crystalline orange solid: Mass spectrum (ESI, m/z): Calcd. for $C_{17}H_{25}FN_4O_2$, 337.2 (M+H), found 337.2.

c) 5-Cyano-furan-2-carboxylic acid [5-fluoro-4-(4-methyl-piperazin-1-yl)-2-(4-methyl-piperidin-1-yl)-phenyl]-amide

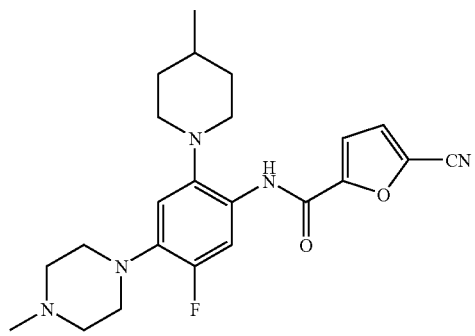

The procedure of Example 4, step (c) was followed using 58.5 mg (0.174 mmol) of 1-[2-fluoro-5-(4-methyl-piperidin-1-yl)-4-nitro-phenyl]-4-methyl-piperazine (as prepared in the previous step), 29 mg of 10% palladium on carbon (50% by weight water), 28.6 mg (0.209 mmol) of 5-cyanofuran-2-carboxylic acid (as prepared in Example 1), 27.3 μL (0.314 mmol) of oxalyl chloride, and 72.8 μL (0.418 mmol) of DIEA except the isolated impure product was dissolved in 10 mL of EtOAc, washed with 1M $K_2CO_3$ (2×5 mL), dried ($Na_2SO_4$) and then concentrated in vacuo. Chromatography on a 5-g silica SPE column with 1-3% MeOH-dichloromethane afforded 60.8 mg (82%) of the title compound as a crystalline yellow solid: $^1$H-NMR (CDCl$_3$; 400 MHz): δ 9.76 (br s, 1H), 8.19 (d, 1H, J=14.1 Hz), 7.22, 7.26 (AB q, 2H, J=3.7 Hz), 6.80 (d, 1H, J=8.5 Hz), 3.11-3.19 (m, 4H), 2.92-2.95 (m, 2H), 2.69-2.76 (m, 2H), 2.55-2.65 (br m, 4H), 2.37 (s, 3H), 1.82-1.86 (m, 2H), 1.5-1.7 (br m, 1H) and 1.42-1.53 (m, 2H). Mass spectrum (ESI, m/z): Calcd. for $C_{23}H_{28}FN_5O_2$, 426.2 (M+H), found 426.3.

Example 22

5-Cyano-furan-2-carboxylic acid (4-azido-2-piperidin-1-yl-phenyl)-amide

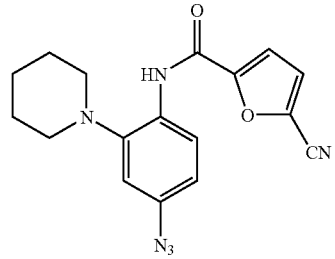

a) 1-(5-Fluoro-2-nitro-phenyl)-piperidine

To a solution of 2,4-difluoronitrobenzene (2.09 g, 13.1 mmol) in EtOH (10 mL) at ambient temperature was added piperidine (3.35 g, 39.4 mmol) dropwise. The reaction was allowed to stir overnight and concentrated in vacuo. The residue was dissolved in EtOAc (100 mL), washed with water (2×100 mL), dried ($Na_2SO_4$) and concentrated in vacuo. Purification by silica gel column chromatography afforded 1.10 (37%) of the title compound as an oil. Mass spectrum (ESI, m/z): Calcd. for $C_{11}H_{13}FN_2O_2$, 225.1 (M+H), found 225.1.

b) 1-(5-Azido-2-nitro-phenyl)-piperidine

To a solution of 1-(fluoro-2-nitro-phenyl)-piperidine (389 mg, 1.73 mmol, as prepared in the previous step) in 5, mL of DMF was added sodium azide (169 mg, 2.60 mmol) and the resultant mixture heated to 50° C. for 14 h, and then 80° C. for 6 h. The reaction was diluted with EtOAc (100 mL), washed with water (2×50 mL), dried ($Na_2SO_4$) and concentrated in vacuo. Purification by preparative TLC (50% EtOAc-hexane) afforded 316 mg (74%) of the title compound as a tan solid. Mass spectrum (ESI, m/z): Calcd. for $C_{11}H_{13}N_5O_2$, 248.1 (M+H), found 247.9.

c) 5-Cyano-furan-2-carboxylic acid (4-azido-2-piperidin-1-yl-phenyl)-amide

To a solution of sodium hydrosulfite (936 mg, 5.30 mmol) in 8 mL of water was added 1-(5-azido-2-nitro-phenyl)-piperidine (133 mg, 0.530 mmol, as prepared in the previous step) in 4 mL of THF dropwise. After 25 min the reaction was poured into 50 mL of brine, extracted with EtOAc (3×30 mL), dried ($Na_2SO_4$), and concentrated in vacuo. The crude product was then allowed to react in a manner similar to Example 4, step (c), with 5-cyano-furan-2-carbonyl chloride (31 mg, 0.20 mmol) in the presence of DIEA (203 μL, 1.16 mmol) to afford 8 mg (12%) of the title compound as an amber solid.

¹H-NMR (CDCl₃; 400 MHz): δ 9.58 (s, 1H), 8.44 (d, 1H, J=7.8 Hz), 7.22-7.30 (m, 2H), 6.81-6.89 (m, 2H), 2.81-2.86 (m, 4H), 1.79-1.82 (m, 4H), 1.62-1.65 (m, 2H); Mass spectrum (ESI, m/z): Calcd. for $C_{17}H_{16}N_6O_2$, 337.1 (M+H), found 337.0.

Example 23

5-(N-Hydroxycarbamimidoyl)-furan-2-carboxylic acid (2,4-di-piperidin-1-yl-phenyl)-amide

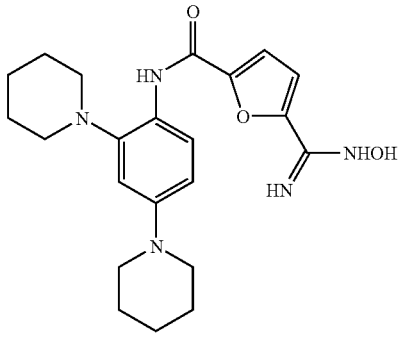

a) 5-Cyano-furan-2-carboxylic acid (2,4-di-piperidin-1-yl-phenyl)-amide

To a solution of 2,4-difluoronitrobenzene (2.09 g, 13.1 mmol) in EtOH (10 mL) at ambient temperature was added piperidine (3.35 g, 39.4 mmol) dropwise. The reaction was allowed to stir overnight and concentrated in vacuo. The residue was dissolved in EtOAc (100 mL), washed with water (2×100 mL), dried (Na₂SO₄) and concentrated in vacuo. Purification by silica gel column chromatography (10% EtOAc-hexane) afforded 610 mg (16%) of 2,4-dipiperidinylnitrobenzene as an oil. 2,4-dipiperidinylnitrobenzene (273 mg, 0.94 mmol) was then stirred in the presence of 168 mg of 5% Pd—C in 10 mL of MeOH under H₂ for 2 h. The reaction was filtered through Celite and concentrated in vacuo to afford 230 mg of 2,4-dipiperidinylaminobenzene (94%) as an oil. Using a procedure similar to Example 4, step (c), 2,4-dipiperidinylaminobenzene (100 mg, 0.38 mmol) was allowed to react with 5-cyano-furan-2-carbonyl chloride (73 mg, 0.46 mmol) in the presence of DIEA (145 μL, 0.83 mmol) to afford 90 mg 62%) of the title compound as a yellow solid. Mass spectrum (ESI, m/z): Calcd. for $C_{22}H_{26}N_4O_2$, 379.2 (M+H), found 379.2.

b) 5-(N-Hydroxycarbamimidoyl)-furan-2-carboxylic acid (2,4-di-piperidin-1-yl-phenyl)-amide To a solution of 5-cyano-furan-2-carboxylic acid (2,4-dipiperidin-1-yl-phenyl)-amide (48 mg, 0.12 mmol, as prepared in the previous step) in 1 mL of EtOH at room temperature was added NH₂OH (26 mg, 0.4 mmol, 50% wt/H₂O) via syringe. The reaction was heated to reflux for 10 min, and then cooled to 0° C. The bright yellow precipitate was filtered, washed with cold 50% EtOH—H₂O (2 mL) and dried to afford 11 mg (23%) of the title compound as a bright yellow solid. ¹H-NMR (DMSO-d₆; 400 MHz): δ 9.83 (s, 1H), 9.37 (s, 1H), 7.84 (d, 1H, J=9.0 Hz), 7.21 (d, 1H, J=3.5 Hz), 6.89 (d, 1H, J=3.6 Hz), 6.74 (s, 1H), 6.66 (d, 1H, J=8.8 Hz), 5.96 (br s, 2H), 3.08-3.10 (m, 4H), 2.78-2.77 (m, 4H), 1.71-1.52 (m, 12H); Mass spectrum (ESI, m/z): Calcd. for $C_{22}H_{29}N_5O_3$ 412.2 (M+H), found 412.2;

Example 24

5-Cyano-furan-2-carboxylic acid [4-(4-methyl-pyrazol-1-yl)-2-piperidin-1-yl-phenyl]-amide

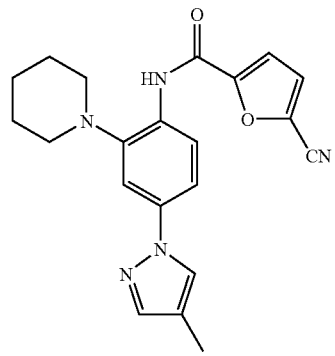

a) 1-[5-(4-Methyl-pyrazol-1-yl)-2-nitro-phenyl]-piperidine

A solution of 1-(5-fluoro-2-nitro-phenyl)-piperidine (98 mg, 0.43 mmol, as prepared in Example 22, step (a), 3-methylpyrazole (49.2 mg, 0.6 mmol), and NaOH (22.4 mg, 0.56 mmol) were heated in 3 mL of DMSO at 90° C. overnight. The reaction was diluted with EtOAc (50 mL), washed with water (2×50 mL), dried (Na₂SO₄) and concentrated in vacuo to afford 117 mg (95%) the title compound as a yellow solid. Mass spectrum (ESI, m/z): Calcd. for $C_{15}H_{18}N_4O_2$ 287.1 (M+H), found 287.1.

b) 5-Cyano-furan-2-carboxylic acid [4-(4-methyl-pyrazol-1-yl)-2-piperidin-1-yl-phenyl]-amide 1-[5-(4-Methyl-pyrazol-1-yl)-2-nitro-phenyl]-piperidine (110 mg, 0.38 mmol, as prepared in the previous step) was allowed to react with TiCl₃ (2.3 mL, 3.8 mmol) in 3 mL of THF. The reaction was quenched with satd aq NaHCO₃ (15 mL) and poured into 25 mL of EtOAc. The organic layer was separated, washed with water (2×25 mL), dried (Na₂SO₄), and concentrated in vacuo to afford 94 mg (95%) of 4-(4-methyl-pyrazol-1-yl)-2-piperidin-1-yl-phenylamine, which was allowed to react in a similar manner to Example 4, step (c), with 5-cyano-furan-2-carbonyl chloride (84 mg, 0.54 mmol) in the presence of DIEA (137 μL, 0.79 mmol) to afford 52.7 mg (47%) of the title compound as a light yellow solid. ¹H-NMR (CDCl₃; 400 MHz): δ 9.65 (s, 1H), 8.50 (d, 1H, J=8.8 Hz), 7.92 (s, 1H), 7.71 (s, 1H), 7.37 (dd, 1H, J=2.5, 8.8 Hz), 7.29 (d, 1H, J=3.8 Hz), 7.23 (d, 1H, J=3.7 Hz), 6.46-6.45 (m, 1H), 2.94-2.89 (m, 4H), 2.14 (s, 3H), 1.85-1.80 (m, 4H), 1.66 (br s, 2H); Mass spectrum (ESI, m/z): Calcd. for $C_{21}H_{21}N_5O_2$, 376.1 (M+H), found 376.1.

Example 25

4-Methyl-piperazine-1-carboxylic acid {4-[(5-cyano-furan-2-carbonyl)-amino]-3-piperidin-1-yl-phenyl}-methyl-amide

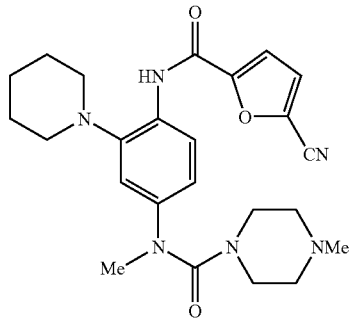

a) Methyl-(4-nitro-3-piperidin-1-yl-phenyl)-amine

A solution of 1-(5-fluoro-2-nitro-phenyl)-piperidine (200 mg, 0.890 mmol) in 4 mL of 2M methylamine in MeOH was heated in a sealed tube for 12 h at 80° C. Removal of the solvent under vacuum afforded methyl-(4-nitro-3-piperidin-1-yl-phenyl)-amine (209 mg, 100%). Mass spectrum (ESI, m/z): Calcd. for $C_{12}H_{17}N_3O_2$, 236.1 (M+H), found 236.1.

b) 4-Methyl-piperazine-1-carboxylic acid methyl-(4-nitro-3-piperidin-1-yl-phenyl)-amide To a solution of triphosgene (40.6 mg, 0.13 mmol) in 2 mL of CH2Cl2 was added methyl-(4-nitro-3-piperidin-1-yl-phenyl)-amine (88 mg, 0.37 mmol) and DIEA (38 μL, 0.22 mmol) in 2 mL of $CH_2Cl_2$ over a 15 min. period. A solution of N-methylpiperazine (1.2 eq, 41 μL) and DIEA (38 μL, 0.22 mmol) in 1.5 mL of $CH_2Cl_2$ were then added via cannula and stirring was continued for 10 min. The reaction was diluted with $CHCl_3$ (50 mL) and washed with satd aq $NaHCO_3$ (50 mL). The organic layer was dried ($Na_2SO_4$) and concentrated in vacuo to give 115 mg (86%) of the title compound a yellow oil. Mass spectrum (ESI, m/z): Calcd. for $C_{18}H_{27}N_5O_3$, 362.2 (M+H), found 362.2.

c) 4-Methyl-piperazine-1-carboxylic acid {4-[(5-cyano-furan-2-carbonyl)-amino]-3-piperidin-1-yl-phenyl}-methyl-amide Using a procedure similar to Example 23, step (a), 4-methyl-piperazine-1-carboxylic acid methyl-(4-nitro-3-piperidin-1-yl-phenyl)-amide (110 mg, 0.3 mmol, as prepared in the previous step) was stirred in MeOH in the presence of 5% Pd—C (65 mg) to afford crude 4-methyl-piperazine-1-carboxylic acid (4-amino-3-piperidin-1-yl-phenyl)-methyl-amide as an oil, which in a manner similar to Example 4, step (c) was coupled to 5-cyano-furan-2-carbonyl chloride (64.6 μL, 412 mmol) in the presence of DIEA (115 μL, 0.6 mmol) using a procedure similar to Example 2 to afford 54.4 mg (40%) of the title compound as a bright yellow solid. $^1$H-NMR (CDCl$_3$, 400 MHz): δ 9.62 (s, 1H), 8.41 (d, 1H, J=8.5 Hz), 7.29 (d, 1H, J=3.8 Hz), 7.24 (d, 1H, J=3.8 Hz), 6.95-6.92 (m, 2H), 3.24-3.26 (M, 4H), 3.22 (s, 3H), 2.84-2.82 (m, 4H), 2.21-2.26 (m, 7H), 1.84-1.79 (m, 4H), 1.66 (m, 2H); Mass spectrum (ESI, m/z): Calcd. for $C_{24}H_{30}N_6O_3$, 451.2 (M+H), found 451.1.

Example 26

5-Cyano-furan-2-carboxylic acid [4-(methanesulfonyl-methyl-amino)-2-piperidin-1-yl-phenyl]-amide

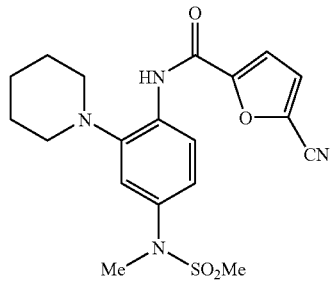

a) N-Methyl-(4-nitro-3-piperidin-1-yl-phenyl)-amine

A solution of 1-(5-fluoro-2-nitro-phenyl)-piperidine (200 mg, 0.89 mmol) in 4 mL of 2M methylamine in MeOH was heated in a sealed tube for 12 h at 80° C. Removal of the solvent under vacuum afforded methyl-(4-nitro-3-piperidin-1-yl-phenyl)-amine (209 mg, 100%). Mass spectrum (ESI, m/z): Calcd for $C_{12}H_{17}N_3O_2$, 236.1 (M+H), found 236.1.

b) N-Methyl-N-(4-nitro-3-piperidin-1-yl-phenyl)-methanesulfonamide

To a solution of N-methyl-(4-nitro-3-piperidin-1-yl-phenyl)-amine (128 mg, 0.54 mmol, as prepared in the previous step) and triethylamine (301 μL, 2.16 mmol) in 4 mL of $CH_2Cl_2$ was added mesyl chloride (125 μL, 1.62 mmol) via microsyringe and the reaction was allowed to stir overnight. At this time it was diluted with $CHCl_3$ (50 mL), washed with satd aq $NaHCO_3$ (2×50 mL), and dried ($Na_2SO_4$). Concentration of the solvent in vacuo and purification of the crude material using preparative TLC (4% MeOH—$CHCl_3$) afforded 154 mg (91%) of the title compound as an oil. Mass spectrum (ESI, m/z): Calcd. for $C_{13}H_{19}N_3O_4S$, 314.1 (M+H), found 314.1.

c) 5-Cyano-furan-2-carboxylic acid [4-(methanesulfonyl-methyl-amino)-2-piperidin-1-yl-phenyl]-amide Using a procedure similar to Example 23, step (a), N-methyl-N-(4-nitro-3-piperidin-1-yl-phenyl)-methanesulfonamide (89 mg, 0.28 mmol) was stirred with 5% Pd—C (55 mg) under $H_2$ to afford 72 mg (91%) of N-(4-Amino-3-piperidin-1-yl-phenyl)-N-methyl-methanesulfonamide as an oil. Using a procedure similar to Example 4, step (c), N-(4-amino-3-piperidin-1-yl-phenyl)-N-methyl-methanesulfonamide was coupled to 5-cyano-furan-2-carbonyl chloride (77 mg, 0.49 mmol) in the presence of DIEA (107 μL, 0.55 mmol) to afford 26.2 mg (23%) of the title compound as a yellow powder. $^1$H-NMR (DMSO-d$_6$, 400 MHz): δ 9.66 (s, 1H), 8.10 (d, 1H, J=8.7 Hz), 7.81 (d, 1H, J=3.8 Hz), 7.52 (d, 1H, J=3.7 Hz),), 7.26 (d, 1H, J=2.8 Hz), 7.21-7.19 (m, 1H), 3.23 (s, 3H), 2.95

(s, 3H), 2.84-2.82 (m, 4H), 1.72 (br s, 4H), 1.57 (br s, 2H); Mass spectrum (ESI, m/z): Calcd. for $C_{19}H_{22}N_4O_4S$, 403.1 (M+H), found 403.1.

Example 27

Acetic acid {4-[(5-cyano-furan-2-carbonyl)-amino]-3-piperidin-1-yl-phenylcarbamoyl}-methyl ester

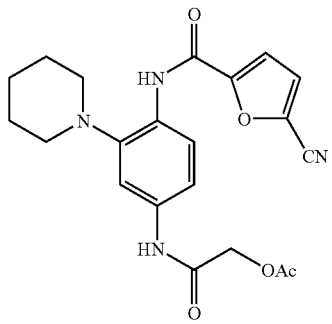

a) 4-Nitro-3-piperidin-1-yl-phenylamine

A solution of 1-(5-fluoro-2-nitro-phenyl)-piperidine (514 mg, 2.29 mmol) in 10 mL of saturated $NH_3$-MeOH were heated in a sealed tube at 110° C. for 48 h. The result was concentrated in vacuo and purified by preparative thin layer chromatography to afford 240 mg (47%) of the title compound. Mass spectrum (ESI, m/z): Calcd. for $C_{11}H_{15}N_3O_2$, 222.1 (M+H), found 222.2.

b) Acetic acid (4-amino-3-piperidin-1-yl-phenylcarbamoyl)-methyl ester

To a solution of 4-nitro-3-piperidin-1-yl-phenylamine (78 mg, 0.35 mmol) and DIEA (152 mL, 0.8 mmol) in 4 mL of $CH_2Cl_2$ was added acetoxyacetychloride (57 mL, 0.50 mmol) via microsyringe. After 1 h, the reaction was diluted with $CH_2Cl_2$ (50 mL), washed with satd aq $NaHCO_3$ (50 mL) and dried. The solvent was filtered through $SiO_2$ and concentrated in vacuo to afford 106 mg (99%) of the title compound as an oil. Using a procedure similar to Example 1, the crude product was stirred with 5% Pd—C (50 mg) under $H_2$ to afford 80 mg (78%) of the title compound as an oil. Mass spectrum (ESI, m/z): Calcd. for $C_{15}H_{21}N_3O_3$, 292.1 (M+H), found 292.1.

c) Acetic acid {4-[(5-cyano-furan-2-carbonyl)-amino]-3-piperidin-1-yl-phenylcarbamoyl}-methyl ester Using a procedure similar to Example 4, step (c), acetic acid (4-amino-3-piperidin-1-yl-phenylcarbamoyl)-methyl ester (80 mg, 0.27 mmol) was allowed to react with 5-cyano-furan-2-carbonyl chloride (42 mg, 0.27 mmol) in the presence of DIEA (0.10 mL, 0.59 mmol) to afford 22 mg (20%) of the title compound as a yellow solid. $^1$H-NMR ($CDCl_3$; 400 MHz): δ 9.66 (s, 1H), 8.40 (d, 1H, J=9.0 Hz), 7.73-7.76 (m, 2H), 7.27-7.28 (m, 1H), 7.22 (d, 1H, J=2.7 Hz), 7.08 (dd, 1H, J=2.3, 8.7 Hz), 4.68 (s, 2H), 2.84-2.86 (m, 4H), 2.24 (s, 3H), 1.82-1.84 (m, 4H), 1.68 (br s, 2H); Mass spectrum (ESI, m/z): Calcd. for $C_{21}H_{22}N_4O_5$, 411.1 (M+H), found 411.1.

Example 28

5-Cyano-furan-2-carboxylic acid (4-methanesulfonylamino-2-piperidin-1-yl-phenyl)-amide

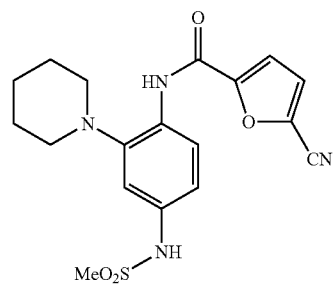

a) N-(4-Nitro-3-piperidin-1-yl-phenyl)-bis-methanesulfonamide

To a solution of 4-nitro-3-piperidin-1-yl-phenylamine (75 mg, 0.54 mmol, as prepared in Example 27, step (a)) and N-methylmorpholine (0.67 mmol, 74 μL) in 4 mL of $CH_2Cl_2$ was added mesyl chloride (33 μL, 0.42 mmol) via microsyringe and the reaction was allowed to stir overnight. At this time it was diluted with $CHCl_3$ (50 μL), washed with satd aq $NaHCO_3$ (2×50 mL), and dried ($Na_2SO_4$). Concentration of the solvent in vacuo and purification of the crude material using preparative TLC (4% MeOH—$CHCl_3$) afforded 21 mg (21%) of the mono sulfonamide and 40 mg (32%) of the title compound as a yellow oil. Mass spectrum (ESI, m/z): Calcd. for $C_{13}H_{19}N_3O_6S_2$, 378.0 (M+H), found 300.0 [M—$SO_2Me$]+2H.

b) 5-Cyano-furan-2-carboxylic acid-(4-methanesulfonylamino-2-piperidin-1-yl-phenyl)-amide Using a procedure similar to Example 23, step (a), N-(4-nitro-3-piperidin-1-yl-phenyl)-bis-methanesulfonamide (40 mg, 0.1 mmol, as prepared in the previous step) was stirred with 20 mg 5% Pd—C in 5 mL MeOH under $H_2$ to afford 35 mg (100%) of the title compound as an oil, which was used immediately without further purification. Using a procedure similar to Example 4, step (c), N-(4-amino-3-piperidin-1-yl-phenyl)-bis-methanesulfonamide (35 mg, 0.10 mmol)) was allowed to react with 5-cyano-furan-2-carbonyl chloride (17 mg, 0.11 mmol) in the presence of DIEA (38 μL, 0.22 mmol) to afford 9.7 mg (25%) of the title compound as a yellow solid. $^1$H-NMR ($CDCl_3$; 400 MHz): δ 9.59 (s, 1H), 8.43 (d, 1H, J=8.7 Hz), 7.31 (d, 1H, J=3.7 Hz), 7.25 (dd, 1H, J=0.7, 3.7 Hz),), 7.18 (d, 1H, J=2.2 Hz), 6.94-6.98 (m, 1H), 6.47 (s, 1H), 3.02 (s, 3H), 2.86-2.88 (m, 4H), 1.82-1.85 (m, 4H), 1.61 (br s, 2H); Mass spectrum (ESI, m/z): Calcd. for $C_{18}H_{20}N_4O_4S$, 389.1 (M+H), found 389.1.

Example 29

5-Cyano-furan-2-carboxylic acid [4-methyl-6'-(4-methyl-piperidin-1-yl)-3,4,5,6-tetrahydro-2H-[1,2']-bipyrazinyl-5'-yl]-amide

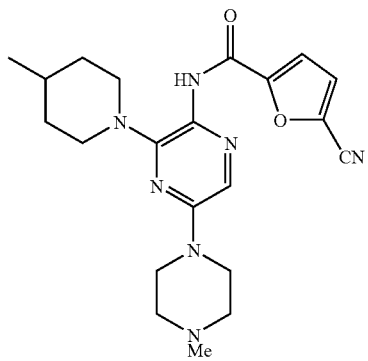

a) 6'-Chloro-4-methyl-3,4,5,6-tetrahydro-2H-[1,2']bipyrazinyl

To a solution of 2,6-dichloropyrazine (400 mg, 2.68 mmol) in 6 mL of $CH_2Cl_2$ was added 4-methylpiperidine (1.2 eq, 3.2 mmol) and allowed to stir overnight. The reaction was diluted with $CH_2Cl_2$ (50 mL) washed with $H_2O$ (2×50 mL) and dried ($K_2CO_3$) to give 450 mg (80%) of the title compound as a white solid. Mass spectrum (ESI, m/z): Calcd. for $C_{11}H_{15}ClN_2$, 211.0 (M+H), found 211.1.

b) 6'-Chloro-4-methyl-5'-nitro-3,4,5,6-tetrahydro-2H-[1,2']bipyrazinyl

To a solution of 6'-chloro-4-methyl-3,4,5,6-tetrahydro-2H-[1,2']bipyridinyl (450 mg (2.12 mmol, as prepared in the previous step) in 7 mL of $CH_3CN$ was added $NO_2BF_4$ (198 mg, 1.48 mmol) in three portions. After 10 min, the reaction was cooled to the freezing point of −50° C. and another 98 mg (0.73 mmol) of $NO_2BF_4$ was added in one portion. The reaction was stirred for 20 min, warmed to 0° C., and placed in a freezer overnight. At this time the reaction was quenched with satd aq $NaHCO_3$ (50 mL), extracted with EtOAc (2×20 mL), and dried ($K_2CO_3$). The EtOAc was removed in vacuo and the crude material was purified by preparative thin layer chromatography (20% EtOAc-hexane) to afford 42 mg (8%) of the title compound as a yellow solid. $^1$H-NMR (CDCl$_3$; 400 MHz): δ 7.65 (s, 1H), 3.91-3.86 (m, 2H), 3.11-3.04 (m, 2H), 1.66-1.80 (m, 3H), 1.34-1.24 (m, 2H), 1.01 (d, 3H, J=6.4 Hz);

c) 4-Methyl-6'-(4-methyl-piperidin-1-yl)-5'-nitro-3,4,5,6-tetrahydro-2H-[1,2']bipyrazinyl To 6'-chloro-4-methyl-5'-nitro-3,4,5,6-tetrahydro-2H-[1,2']bipyrazinyl (32 mg, 0.12 mmol) was added N-methylpiperazine (370 mg, 3.7 mmol) and the resultant solution was stirred for 15 min. The reaction was diluted with EtOAc (50 mL), washed with $H_2O$ (2×20 mL), dried ($K_2CO_3$) and concentrated in vacuo to afford 37 mg (96%) of the title compound. Mass spectrum (ESI, m/z): Calcd. for $C_{15}H_{24}N_6O_2$, 321.2 (M+H), found 321.1.

d) 5-Cyano-furan-2-carboxylic acid [4-methyl-6'-(4-methyl-piperidin-1-yl)-3,4,5,6-tetrahydro-2H-[1,2']-bipyrazinyl-5'-yl]-amide Using a procedure similar to Example 23, step (a) 4-methyl-6'-(4-methyl-piperidin-1-yl)-5'-nitro-3,4,5,6-tetrahydro-2H-[1,2']bipyrazinyl (37 mg, 0.11 mmol) was stirred with 20 mg 5% Pd—C in 5 mL MeOH under $H_2$ to afford 32 mg (100%) of the title compound as an oil, which was used immediately without further purification. Using a procedure similar to Example 4, step (c), 4-methyl-6'-(4-methyl-piperidin-1-yl)-3,4,5,6-tetrahydro-2H-[1,2']bipyrazinyl-5'-ylamine (32 mg, 0.10 mmol)) was allowed to react with 5-cyano-furan-2-carbonyl chloride (44.6 mg, 0.28 mmol) in the presence of DIEA (107 μL, 0.610 mmol) to afford 10 mg (25%) of the title compound as a dark semi-solid. $^1$H-NMR (CDCl$_3$; 400 MHz): δ 8.29 (s, 1H), 7.57 (s, 1H), 7.32 (d, 1H, J=3.6 Hz), 7.24-7.23 (d, 1H, J=3.6 Hz), 3.60-3.57 (m, 6H), 2.87-2.81 (m, 2H), 2.57-2.54 (m, 4H), 2.39 (s, 3H), 1.77-1.73 (m, 2H), 1.66-1.55 (m, 1H), 1.40-1.32 (m, 2H), 1.02 (d, 3H, J=6.5 Hz); Mass spectrum (ESI, m/z): Calcd. for $C_{21}H_{27}N_7O_2$, 410.2 (M+H), found 410.2.

Example 30

5-Cyano-furan-2-carboxylic acid [4-(4-methyl-piperazin-1-yl)-2-piperidin-1-yl-phenyl]-amide hydrochloride

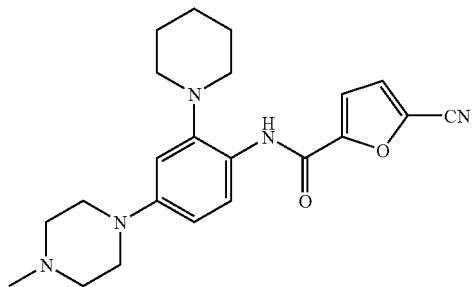

a) 4-(4-Methyl-piperazin-1-yl)-2-piperidin-1-yl-phenylamine 1-(5-Fluoro-2-nitro-phenyl)-piperidine (100 mg, 0.44 mmol) was treated with N-methylpiperizine (3 mL) and heated to 80° C. overnight. The reaction was diluted with EtOAc (10 mL), washed with water (2×10 mL), dried ($Na_2SO_4$) and concentrated in vacuo to afford 118 mg (88%) of 1-methyl-4-(4-nitro-3-piperidin-1-yl-phenyl)-piperazine as an oil. The 1-methyl-4-(4-nitro-3-piperidin-1-yl-phenyl)-piperazine (22 mg, 0.07 mmol) was stirred with 13 mg 5% Pd—C in 1 mL of MeOH under $H_2$ for 2 h. The mixture was filtered through $SiO_2$, eluting with 10% MeOH—CHCl$_3$, and the solvent was concentrated in vacuo to give 17 mg (86%) of the title compound as a white solid. Mass spectrum (ESI, m/z): Calcd. for $C_{16}H_{26}N_4$, 275.22 (M+H), found 275.2.

b) 5-Cyano-furan-2-carboxylic acid [4-(4-methyl-piperazin-1-yl)-2-piperidin-1-yl-phenyl]-amide hydrochloride Using a procedure similar to Example 4, step (c), 4-(4-methyl-piperazin-1-yl)-2-piperidin-1-yl-phenylamine (2.84 g, 9.80 mmol) was allowed to react with 5-cyano-furan-2-carbonyl chloride (2.42 g, 15.6 mmol) in the presence of DIEA (4.26 mL, 24.0 mmol) to afford 2.02 g of free base as a yellow solid. The free base was sonicated in 20 mL of ether for 5 min, and then cooled to 0° C. At this time 12.8 mL of a 0.4 M HCL-ether solution was slowly added via syringe, stirring was continued for 10 min and the mixture was warmed to room temperature. Another 20 mL of ether was added, the mixture was stirred vigorously, and the solvent removed by a syringe. The resultant powder was dried under vacuum to afford 2.20 g (100%) of the title compound as a yellow powder. $^1$H-NMR (DMSO-$d_6$; 400 MHz): δ 9.51 (s, 1H), 7.90 (d, 1H, J=8.8 Hz), 7.78 (d, 1H, J=3.8 Hz), 7.45 (d, H, J=3.8 Hz), 6.80 (d, 1H, J=2.3 Hz), 6.72 (dd, 1H, J=2.6, 8.8 Hz), 3.35 (m, 4H, obscured by solvent), 2.93 (br s, 4H), 2.81-2.78 (m, 4H), 2.48 (s, 3H), 1.68 bs, 4H), 1.55-1.54 (m, 2H); Mass spectrum (ESI, m/z): Calcd. for $C_{22}H_{27}N_5O_2$, 394.2 (M+1), found 394.1.

Example 31

4-[4-[(5-Cyano-furan-2-carbonyl)-amino]-3-(2,5-dimethyl-pyrrol-1-yl)-phenyl]-piperazine-1-carboxylic acid tert-butyl ester

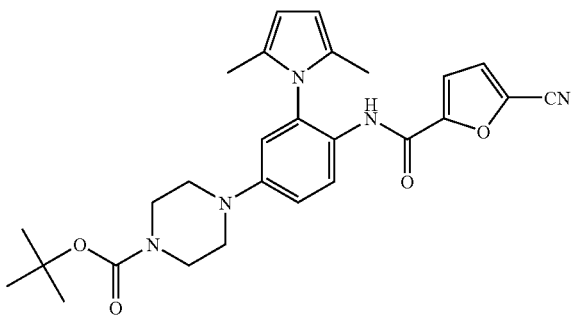

a) 1-(5-Chloro-2-nitro-phenyl)-2,5-dimethyl-1H-pyrrole

To a solution of 5-chloro-2-nitrophenylamine (200 mg, 1.15 mmol) and hexane-2,5-dione (326 μL, 2.78 mmol) in THF (3 mL) was added 1 drop of conc $H_2SO_4$. Toluene (3 mL) was then added and the reaction was allowed to stir at 120° C. overnight. At this time the reaction was diluted with $CH_2Cl_2$ (50 mL), washed with $H_2O$ (2×25 mL), dried ($Na_2SO_4$) and concentrated in vacuo. Purification by preparative thin layer chromatography (50% EtOAc-hexane) afforded 73 mg (25%) of the title compound as a tan solid. $^1$H-NMR (CDCl$_3$; 400 MHz): δ 7.96 (d, 1H, J=8.7 Hz), 7.59-7.54 (m, 1H), 7.39 (d, 1H, J=2.0 Hz), 5.92 (s, 2H), 1.97 (s, 6H);

b) 4-[3-(2,5-Dimethyl-pyrrol-1-yl)-4-nitro-phenyl]-piperazine-1-carboxylic acid tert-butyl ester To a stirred solution of 1-(5-chloro-2-nitro-phenyl)-2,5-dimethyl-1H-pyrrole (73 mg, 0.29 mmol, as prepared in the previous step) in DMF (2 mL) was added piperazine-1-carboxylic acid tert-butyl ester (542 mg, 2.9 mmol) and the result was heated to 90° C. for 18 h. The reaction a diluted with EtOAc (50 mL), washed with $H_2O$ (2×25 mL), dried ($Na_2SO_4$) and concentrated in vacuo. The residue was chromtographed on a SPE column (5 g, SiO$_2$) to afford 35 mg (30%) of the title compound as a brown solid. $^1$H-NMR (CDCl$_3$; 400 MHz): δ 8.13 (d, 1H, J=9.3 Hz), 6.91-6.88 (m, 1H), 6.66 (s, 1H), 5.93 (s, 2H), 3.63-3.60 (m, 4H), 3.42-3.40 (m, 4H), 1.97 (s, 6H), 1.48 (s, 9H).

c) 4-[4-Amino-3-(2,5-dimethyl-pyrrol-1-yl)-phenyl]-piperazine-1-carboxylic acid tert-butyl ester Using a procedure similar to Example 23, step (a), 4-[3-(2,5-dimethyl-pyrrol-1-yl)-4-nitro-phenyl]-piperazine-1-carboxylic acid tert-butyl ester (35 mg, 0.08 mmol) was stirred in MeOH in the presence of 5% Pd—C (20 mg) to afford 30 mg (100%) of the title compound as an oil. Mass spectrum (ESI, m/z): Calcd. for $C_{21}H_{30}N_4O_2$, 371.2 (M+H), found 371.1.

d) 4-[4-[(5-Cyano-furan-2-carbonyl)-amino]-3-(2,5-dimethyl-pyrrol-1-yl)-phenyl]-piperazine-1-carboxylic acid tert-butyl ester Using a procedure similar to Example 4, step (c), 4-[4-amino-3-(2,5-dimethyl-pyrrol-1-yl)-phenyl]-piperazine-1-carboxylic acid tert-butyl ester (30 mg, 0.8 mmol) was allowed to react with 5-cyano-furan-2-carbonyl chloride (25 mg, 0.16 mmol) in the presence of DIEA (276 mg, 1.7 mmol) to afford 14.9 mg (38%) of the title compound as a yellow solid. 1H-NMR (CDCl$_3$, 400 MHz): □8.43 (d, 1H, J=9.3 Hz), 7.25 (s, 1H), 7.10-7.13 (m, 2H), 7.03-7.06 (m, 1H), 6.89 (s, 1H), 6.06 (s, 2H), 3.62-3.61 (m, 4H), 3.18-3.17 (m, 4H), 1.96 (s, 6H), 1.48 (s, 9H); Mass spectrum (ESI, m/z): Calcd. for $C_{27}H_{31}N_5O_4$, 390.1 (M-BOC+2H), found 390.1.

Example 32

4-[4-(4-Methyl-piperazin-1-yl)-2-piperidin-1-yl-phenylcarbamoyl]-oxazole-2-carboxylic acid methyl ester

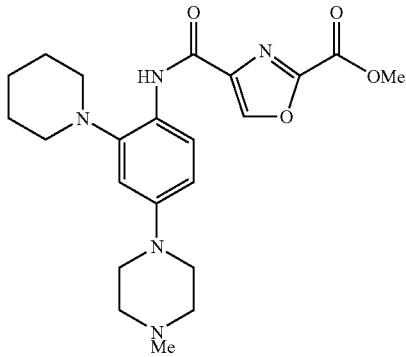

a) 2-Cyano-oxazole-4-carboxylic acid ethyl ester

To a solution of 2-formyl-oxazole-4-carboxylic acid ethyl ester (Panek et al. *J. Org. Chem.*, 6496, (1996)) (171 mg, 1.11 mmol) in MeOH (3 mL) was added NH$_2$OH (50% wt. H$_2$O, 161 μL, 2.4 mmol). The reaction was allowed to stir for 2 h, and then concentrated in vacuo. The crude oxime was treated with acetic anhydride (4 mL) and heated with stirring at 150° C. for 24 h. The acetic anhydride was removed under vacuo, and the crude material was purified by preparative thin layer chromatography (60% ether-hexanes) to afford 56 mg (31%) of the title compound as an off-white solid. $^1$H-NMR (CDCl$_3$; 400 MHz): δ 8.40 (s, 1H), 4.46 (q, 2H, J=7.1 Hz), 1.43 (t, 3H, J=7.1 Hz).

b) 4-[4-(4-Methyl-piperazin-1-yl)-2-piperidin-1-yl-phenylcarbamoyl]-oxazole-2-carboxylic acid methyl ester To a stirred solution of 2-cyano-oxazole-4-carboxylic acid ethyl ester (60 mg, 0.36 mmol, as prepared in the previous step) in 3 mL of THF-MeOH (1/1, v/v) was added 6N NaOH (365 μL, 2.19 mmol). The reaction was then acidified to pH=4 with 6N HCl, and extracted with EtOAc (2×20 mL). The organic extracts were dried (Na$_2$SO$_4$) and concentrated in vacuo to afford 46 mg of 2-oxazole-2,4-dicarboxylic acid 2-methyl ester. The acid in CH$_2$Cl$_2$ (3 mL) was treated with oxalyl chloride (34 mL, 0.39 mmol) and allowed to stir for 30 min. At this time the solvent was removed in vacuo, and the crude acid chloride was dissolved in CH$_2$Cl$_2$ (3 mL) and added via cannula to a stirring solution of 4-(4-methyl-piperazin-1-yl)-2-piperidin-1-yl-phenylamine (73 mg, 0.26 mmol) in CH$_2$Cl$_2$ (3 mL). At this time DIEA (122 μL, 0.700 mmol) was added and the reaction was allowed to stir overnight. Using a workup procedure similar to Example 2 afforded 56 mg (40%) of the title compound as a yellow solid. $^1$H-NMR (CDCl$_3$; 400 MHz): □9.92 (s, 1H), 8.39 (s, 1H), 8.32 (d, 1H, J=8.9 Hz), 6.77 (d, 1H, J=2.6 Hz), 6.71 (dd, 1H, J=2.6, 8.8 Hz), 4.12 (s, 3H), 3.21-3.18 (m, 4H), 2.87-2.84 (m, 4H), 2.61-2.58 (m, 4H), 2.36 (s, 3H), 1.88-1.83 (m, 4H), 1.63 (br s, 2H); Mass spectrum (ESI, m/z): Calcd. for C$_{21}$H$_{26}$N$_6$O$_2$, 428.2 (M+H), found 428.2

Example 33

5-Cyano-furan-2-carboxylic acid [2-(4-methyl-piperidin-1-yl)-4-(1,2,3,6-tetrahydro-pyridin-4-yl)-phenyl]-amide dihydrochloride

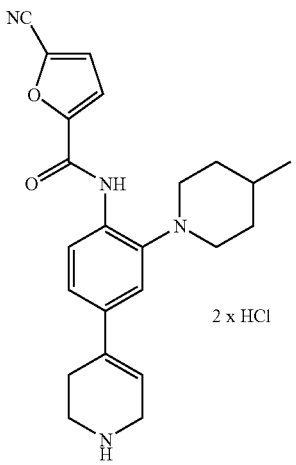

a) 1-(5-Bromo-2-nitro-phenyl)-4-methyl-piperidine

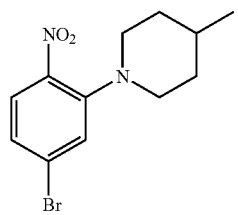

A solution of 4-bromo-2-fluoro-phenylamine (3.00 g, 15.8 mmol) in 15 mL of DCM is added dropwise to a suspension of 3-chloroperoxybenzoic acid (19 g, 57-86%) in 200 mL of DCM at −10° C. and the mixture is allowed to attain RT and stirred for 10 h. The reaction is then washed with saturated aqueous NaHCO$_3$ (2×150 mL) and brine (100 mL), and the organic layer dried over Na$_2$SO$_4$ and evaporated. MeOH (10 mL) was then added to the crude residue to precipitate a white solid that was removed by filtration and the filtrate was concentrated to give 4-bromo-2-fluoro-1-nitro-benzene. This product was dissolved in 100 mL of DCM, cooled to 0° C., and 4-methylpiperidine (5.00 g, 50.8 mmol) was added and the solution was stirred for 10 h at RT. The reaction was diluted with 100 mL of DCM, washed with brine (3×100 mL), and the organic layer dried over Na$_2$SO$_4$ and concentrated. The crude oil was purified by elution from a 20-g solid phase extraction (SPE) cartridge (silica) with 50% DCM/hexanes to give 3.4 g (72%) of the title compound as a yellow oil: Mass spectrum (ESI, m/z): Calcd. for C$_{12}$H$_{15}$BrN$_2$O$_2$, 299.0 (M+H), found 299.1.

b) 1-[5-(5,5-Dimethyl-[1,3,2]dioxaborinan-2-yl)-2-nitro-phenyl]-4-methyl-piperidine

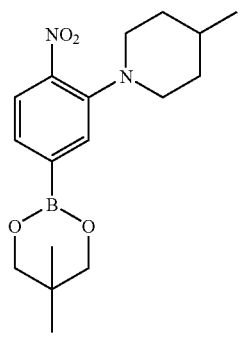

To a solution of 1-(5-bromo-2-nitro-phenyl)-4-methyl-piperidine (0.60 g, 2.0 mmol) (as prepared in the previous step) in 5 mL of methanol was added bis(neopentylglycolato)diboron (0.68 g, 3.0 mmol), potassium acetate (0.40 g, 4.0 mmol), and Pd(dppf)Cl$_2$ (0.07 g, 5 mol %) and the reaction heated for 5 h at 60° C. The solution was concentrated and the product eluted from a 20-g SPE cartridge (silica) with 100% DCM to give 0.46 g (70%) of the title compound as a red oil. $^1$H-NMR (400 MHz, CDCl$_3$): δ 7.71 (d, 1H), 7.59 (d, 1H), 7.40 (dd, 1H), 3.80 (s, 4H), 3.26 (m, 2H), 2.82 (m, 2H), 1.74 (m, 2H), 1.48 (m, 3H), 1.40 (s, 6H), 1.0 (d, 3H).

c) 4-[3-(4-Methyl-piperidin-1-yl)-4-nitro-phenyl]-3,6-dihydro-2H-pyridine-1-carboxylic acid tert-butyl ester

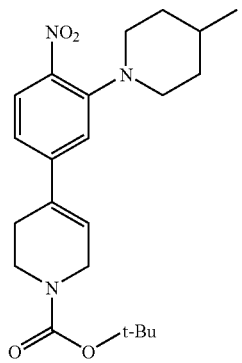

A flask is charged with 1-[5-(5,5-dimethyl-[1,3,2]dioxaborinan-2-yl)-2-nitro-phenyl]-4-methyl-piperidine (0.090 g, 0.27 mmol) (as prepared in the previous step), 4-trifluoromethanesulfonyloxy-3,6-dihydro-2H-pyridine-1-carboxylic acid tert-butyl ester (0.090 g, 0.27 mmol) (Synthesis, 993, (1991)), LiCl (0.022 g, 0.54 mmol), Pd(PPh$_3$)$_4$ (0.015 g, 5 mol %), 2 M Na$_2$CO$_3$ (0.34 mL), DME (0.80 mL) and heated at 80° C. for 30 min. The reaction was diluted with EtOAc (10 mL) and washed with saturated aqueous NaHCO$_3$ (2×10 mL) and brine (10 mL), and the organic layer dried over Na$_2$SO$_4$ and evaporated. The crude product was eluted from a 10-g SPE cartridge (silica) with 10% EtOAc/hexane to give 0.080 g (74%) of the title compound as a light yellow oil. Mass spectrum (ESI, m/z): Calcd. for C$_{22}$H$_{31}$N$_3$O$_4$, 402.2 (M+H), found 402.1.

d) 4-[4-Amino-3-(4-methyl-piperidin-1-yl)-phenyl]-3,6-dihydro-2H-pyridine-1-carboxylic acid tert-butyl ester

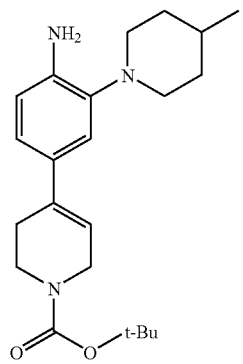

A flask charged with 4-[3-(4-methyl-piperidin-1-yl)-4-nitro-phenyl]-3,6-dihydro-2H-pyridine-1-carboxylic acid tert-butyl ester (0.080 g, 0.20 mmol) (as prepared in the previous step), ammonium chloride (0.10 g, 2.0 mmol), iron powder (0.055 g, 10 mmol), EtOH (1 mL) and water (0.5 mL) was heated at 80° C. for 30 min. The reaction was filtered though Celite, concentrated and eluted from a 10-g SPE cartridge (silica) with 20% EtOAc/hexane to give 0.040 g (50%) of the title compound as a yellow oil. $^1$H-NMR (400 MHz, CDCl$_3$): δ 7.08 (d, 1H), 6.97 (dd, 1H), 6.72 (d, 1H), 5.89 (m, 1H), 4.75 (br s, 2H), 4.08 (m, 2H), 3.63 (m, 2H), 3.12 (m, 2H), 2.62 (m, 2H), 2.50 (m, 2H), 1.78 (m, 2H), 1.52 (s, 9H), 1.38 (m, 3H), 1.00 (d, 3H).

e) 5-Cyano-furan-2-carboxylic acid [2-(4-methyl-piperidin-1-yl)-4-(1,2,3,6-tetrahydro-pyridin-4-yl)-phenyl]-amide dihydrochloride A flask was charged with 5-cyano-furan-2-carboxylic acid (0.015 g, 0.10 mmol) (as prepared in Example 1), DCM (1 mL), DMF (5 μL), and oxalyl chloride (10 μL, 0.11 mmol) and stirred at 25° C. for 1 h and then concentrated. The resulting 5-cyano-furan-2-carbonyl chloride was dissolved in DCM (1 mL) and added to a solution of 4-[4-amino-3-(4-methyl-piperidin-1-yl)-phenyl]-3,6-dihydro-2H-pyridine-1-carboxylic acid tert-butyl ester (0.040 g, 0.10 mmol) (as prepared in the previous step) and NEt$_3$ (25 μL, 0.15 mmol) in DCM (1 mL) at 0° C. The solution was allowed to attain RT and stirred for 10 h. The intermediate BOC protected compound was eluted from a 5-g SPE cartridge (silica) with 20% EtOAc/hexane, and then dissolved in DCM (1 mL) and TFA (0.30 mL) and stirred at 25° C. for 30 min. The reaction was concentrated and purified by RP-HPLC (C18), eluting with a linear gradient of 40% CH$_3$CN to 70% CH$_3$CN in 0.1% TFA/H$_2$O over 10 min to give the title compound as a di-TFA salt. This product was then eluted from a 10-g column of BioRad AG-2X8 resin (chloride ion form) with methanol to give 0.017 g (37%) of the title compound. $^1$H-NMR (400 MHz, DMSO-d$_6$): δ 9.81 (s, 1H), 9.40 (br s, 2H), 8.18 (d, 1H), 7.82 (d, 1H), 7.50 (d, 1H), 7.36 (s, 1H), 7.28 (d, 1H), 6.22 (m, 1H), 3.76 (m, 2H), 3.46 (3, 3H), 2.98 (m, 2H), 2.74 (m, 6H), 1.82 (m, 2H), 1.50 (m, 3H), 1.00 (d, 3H), Mass spectrum (ESI, m/z): Calcd. for C$_{23}$H$_{26}$N$_4$O$_2$, 391.2 (M+H), found 391.2.

Example 34

5-Cyano-furan-2-carboxylic acid [2-(4-methyl-piperidin-1-yl)-4-piperidin-4-yl-phenyl]-amide bis(trifluoracetic acid salt)

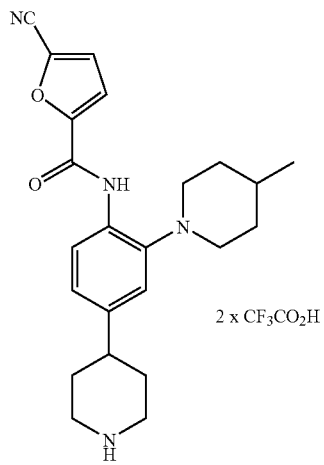

a) 4-[4-Amino-3-(4-methyl-piperidin-1-yl)-phenyl]-piperidine-1-carboxylic acid tert-butyl ester

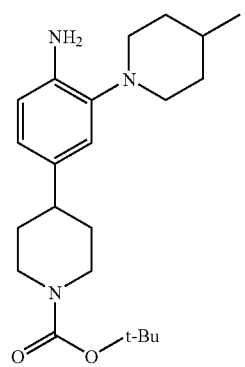

A solution of 4-[3-(4-methyl-piperidin-1-yl)-4-nitro-phenyl]-3,6-dihydro-2H-pyridine-1-carboxylic acid tert-butyl ester (0.090 g, 0.22 mmol) (as prepared in Example 33, step (d)) in methanol (2 mL) was hydrogenated over 10% Pd/C at 12 psi for 2 h. The solution was filtered and concentrated to give 0.085 g (100%) of the title compound as an oil. Mass spectrum (ESI, m/z): Calcd. for $C_{22}H_{35}N_3O_2$, 374.3 (M+H), found 374.1.

b) 5-Cyano-furan-2-carboxylic acid [2-(4-methyl-piperidin-1-yl)-4-piperidin-4-yl-phenyl]-amide bis (trifluoroacetic acid salt)

The title compound was obtained by coupling 4-[4-amino-3-(4-methyl-piperidin-1-yl)-phenyl]-piperidine-1-carboxylic acid tert-butyl ester (as prepared in the previous step) to 5-cyano-furan-2-carboxylic acid (as prepared in Example 1) and BOC deprotection according to the procedure in Example 33, step (e). The title compound was purified by RP-HPLC (C18), eluting with a linear gradient of 30% to 50% $CH_3CN$ in 0.1% $TFA/H_2O$ over 12 min. $^1$H-NMR (400 MHz, DMSO-$d_6$): δ 9.72 (s, 1H), 9.58 (br s, 1H), 9.28 (br s, 1H), 8.18 (d, 1H), 7.82 (d, 1H), 7.48 (d, 1H), 7.12 (s, 1H), 7.04 (d, 1H), 3.40 (m, 2H), 3.00. (m, 4H), 2.80 (m, 3H), 2.95 (m, 2H), 1.80 (m, 4H), 1.50 (m, 3H), 1.02 (d, 3H). Mass spectrum (ESI, m/z): Calcd. for $C_{23}H_{28}N_4O_2$, 393.2 (M+H), found 393.2.

Example 35

4-Cyano-1H-pyrrole-2-carboxylic acid [2-(4-methyl-piperidin-1-yl)-4-piperidin-4-yl-phenyl]-amide bis (trifluoracetic acid salt)

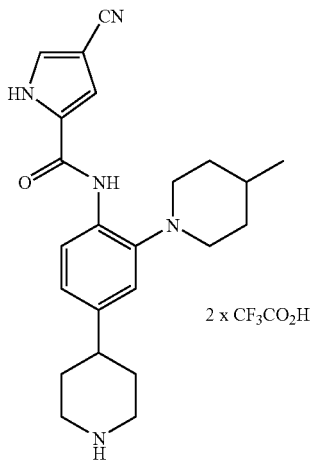

2 x $CF_3CO_2H$

The title compound was obtained by coupling 4-[4-amino-3-(4-methyl-piperidin-1-yl)-phenyl]-piperidine-1-carboxylic acid tert-butyl ester (as prepared in Example 34, step (a)) and 4-cyano-1H-pyrrole-2-carboxylic acid (as prepared in Example 2) followed by BOC deprotection according to the procedure in Example 33, step (e). The title compound was purified by RP-HPLC (C18), eluting with a linear gradient of 30% to 50% $CH_3CN$ in 0.1% $TFA/H_2O$ over 12 min. $^1$H-NMR (400 MHz, $CH_3OD$): δ 7.80 (d, 2H), 7.70 (s, 1H), 7.48 (s, 1H), 7.38 (m, 2H), 3.60. (m, 2H), 3.44 (m, 2H), 3.20 (m, 4H), 3.02 (m, 1H), 2.20-1.50 (m, 9H), 1.08 (d, 3H). Mass spectrum (ESI, m/z): Calcd. for $C_{23}H_{29}N_5O$, 392.2 (M+H), found 392.2.

Example 36

5-Cyano-furan-2-carboxylic acid [4-(1-acetyl-piperidin-4-yl)-2-(4-methyl-piperidin-1-yl)-phenyl]-amide

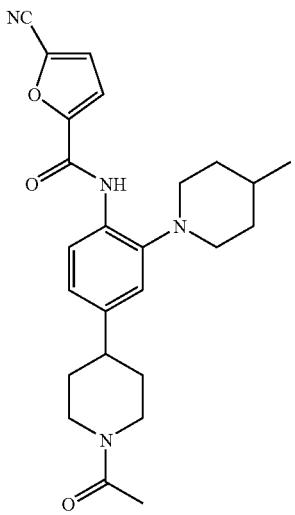

A flask was charged with 5-cyano-furan-2-carboxylic acid [2-(4-methyl-piperidin-1-yl)-4-piperidin-4-yl-phenyl]-amide (0.035 g, 56 µmol) (as prepared in Example 34, step (b)), $NEt_3$ (31.0 µL, 225 µmol), acetic anhydride (6.5 µL, 62 µmol), and DCM (0.5 mL) and stirred at RT for 1 h. The title compound was eluted from a 10-g SPE cartridge (silica) with 5% MeOH/DCM to give 18 mg (75%) of a white solid. $^1$H-NMR (400 MHz, $CDCl_3$): δ 9.78 (s, 1H), 8.34 (d, 1H), 7.24 (m, 2H), 7.01 (m, 2H), 4.80 (m, 2H), 3.96. (m, 2H), 3.20 (t, 1H), 2.98 (m, 2H), 2.70 (m, 4H), 2.28 (s, 3H), 1.88 (m, 4H), 1.60 (m, 5H), 1.10 (d, 3H). Mass spectrum (ESI, m/z): Calcd. for $C_{25}H_{30}N_4O_3$, 435.2 (M+H), found 435.2.

Example 37

5-Cyano-1H-imidazole-2-carboxylic acid [4-(4-methyl-piperazin-1-yl)-2-piperidin-1-yl-phenyl]-amide trifluoroacetic acid salt

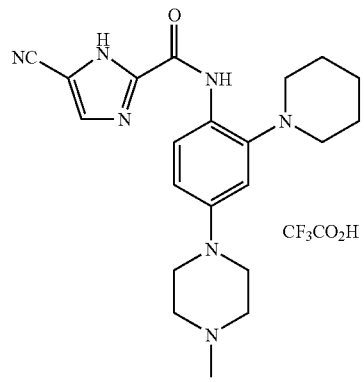

$CF_3CO_2H$ a) 4-Cyano-1-(2-trimethylsilanyl-ethoxymethyl)-1H-imidazole-2-carboxylic acid [4-(4-methyl-piperazin-1-yl)-2-piperidin-1-yl-phenyl]-amide

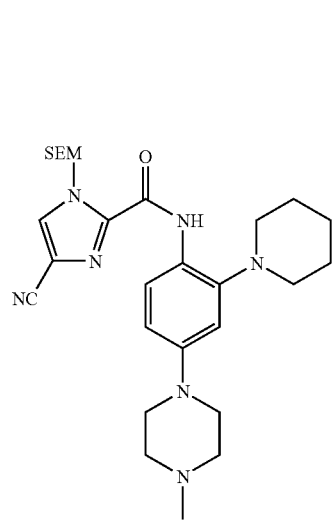

A flask was charged with 4-cyano-1-(2-trimethylsilanyl-ethoxymethyl)-1H-imidazole-2-carboxylate potassium salt (0.043 g, 0.14 mmol) (as prepared in Example 3, step (d)), 4-(4-methyl-piperazin-1-yl)-2-piperidin-1-yl-phenylamine (0.028 g, 0.10 mmol) (as prepared in Example 5, step (b)), EDCI (0.030 g, 0.16 mmol), DMAP (0.012 g, 0.010 mmol), and DMF (0.5 mL) and was stirred for 12 h at RT and then 1 h at 60° C. The reaction mixture was loaded on a 10-g SPE cartridge (silica) and eluted with 10% MeOH/DCM to give 0.030 g (57%) of title compound. Mass spectrum (ESI, m/z): Calcd. for $C_{27}H_{41}N_7O_2Si$, 524.3 (M+H), found 524.1.

b) 5-Cyano-1H-imidazole-2-carboxylic acid [4-(4-methyl-piperazin-1-yl)-2-piperidin-1-yl-phenyl]-amide trifluoroacetic acid salt To a flask charged with 4-cyano-1-(2-trimethylsilanyl-ethoxymethyl)-1H-imidazole-2-carboxylic acid [4-(4-methyl-piperazin-1-yl)-2-piperidin-1-yl-phenyl]-amide (0.030 g, 0.060 mmol) (as prepared in the previous step) was added 6N HCl (0.3 mL) and EtOH (0.6 mL) and the solution heated at 70° C. for 20 min. The reaction was concentrated and the title compound was purified by RP-HPLC (C18), eluting with 10-70% $CH_3CN$ in 0.1% $TFA/H_2O$ over 15 min to give 0.020 g (69%) the title compound. $^1$H-NMR (400 MHz, DMSO-$d_6$): δ 14.28 (s, 1H), 9.84 (s, 1H), 9.65 (br s, 1H), 8.38 (s, 1H), 8.16 (d, 1H), 6.92 (d, 1H), 6.80 (dd, 1H), 3.86 (m, 2H), 3.54. (m, 2H), 3.18 (m, 1H), 2.90 (m, 9H), 1.78 (m, 4H), 1.62 (m, 2H). Mass spectrum (ESI, m/z): Calcd. for $C_{21}H_{27}N_7O$, 394.2 (M+H), found 394.2.

Example 38

3H-Imidazole-4-carboxylic acid [4-(4-methyl-piperazin-1-yl)-2-piperidin-1-yl-phenyl]-amide bis(trifluoroacetic acid salt)

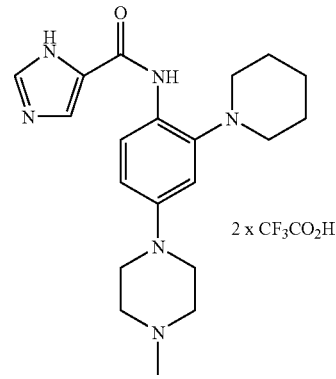

a) 1-(2-Trimethylsilanyl-ethoxymethyl)-1H-imidazole-4-carboxyate sodium salt

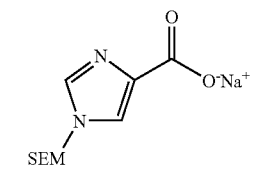

To a solution of 1-(2-trimethylsilanyl-ethoxymethyl)-1H-imidazole-4-carboxylic acid methyl ester (0.42 g, 1.6 mmol) (as prepared in Example 40, step (a)) in MeOH (3.0 mL) was added 1N NaOH (1.6 mL) and mixture was stirred for 8 h at RT. The reaction was concentrated to give 0.43 g (100%) of the title compound as a white solid. Mass spectrum (ESI, m/z): Calcd. for $C_{10}H_{18}N_2O_3Si$, 243.1 (M+H), found 243.1.

b) 3H-Imidazole-4-carboxylic acid [4-(4-methyl-piperazin-1-yl)-2-piperidin-1-yl-phenyl]-amide bis (trifluoroacetic acid salt)

The title compound was prepared by coupling 1-(2-trimethylsilanyl-ethoxymethyl)-1H-imidazole-4-carboxylate sodium salt (as prepared in the previous step) and 4-(4-methyl-piperazin-1-yl)-2-piperidin-1-yl-phenylamine (as prepared in Example 5, step (b)) according to the procedure in Example 37, step (a) followed by SEM deprotection according to the procedure in Example 37, step (b). The title compound was purified by RP-HPLC (C18), eluting with 10-35% $CH_3CN$ in 0.1% $TFA/H_2O$ over 12 min. $^1$H-NMR (400 MHz, $CH_3OD$): δ 8.72 (s, 1H), 8.22 (s, 1H), 7.62 (d, 1H), 7.34 (d, 1H), 7.18 (d, 1H), 4.02 (m, 2H), 3.74 (m, 2H), 3.60 (m, 4H), 3.28 (m, 4H), 3.02 (s, 3H), 2.04 (m, 4H), 1.78 (m, 2H). Mass spectrum (ESI, m/z): Calcd. for $C_{20}H_{28}N_6O$, 369.2 (M+H), found 369.2.

Example 39

1H-Imidazole-2-carboxylic acid [4-(4-methyl-piperazin-1-yl)-2-piperidin-1-yl-phenyl]-amide bis(trifluoroacetic acid salt)

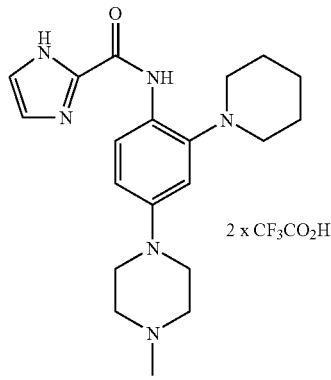

1H-Imidazole-2-carboxylic acid was coupled to 4-(4-methyl-piperazin-1-yl)-2-piperidin-1-yl-phenylamine (as prepared in Example 5, step (b)) according to the procedure in Example 37, step (a). The title compound was purified by RP-HPLC (C18), eluting with 10-35% CH$_3$CN in 0.1% TFA/H$_2$O over 12 min. $^1$H-NMR (400 MHz, CH$_3$OD): δ 8.04 (d, 1H), 7.32 (s, 2H), 7.02 (d, 1H), 6.92 (d, 1H), 3.88 (m, 2H), 3.66 (m, 2H), 3.30 (m, 2H), 3.08 (m, 6H), 3.02 (s, 3H), 1.92 (m, 4H), 1.70 (m, 2H). Mass spectrum (ESI, m/z): Calcd. for C$_{20}$H$_{28}$N$_6$O, 369.2 (M+H), found 369.2.

Example 40

3H-Imidazole-2,4-dicarboxylic acid 2-amide 4-{[4-(4-methyl-piperazin-1-yl)-2-piperidin-1-yl-phenyl]-amide}trifluoroacetic acid salt

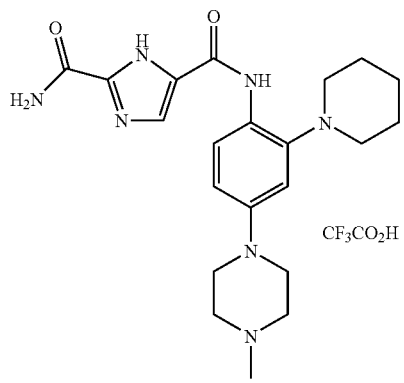

a) 1-(2-Trimethylsilanyl-ethoxymethyl)-1H-imidazole-4-carboxylic acid methyl ester

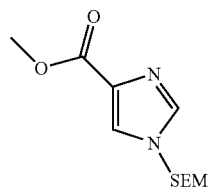

A flask charged with 1H-imidazole-4-carboxylic acid methyl ester (0.54 g, 4.3 mmol), 2-(trimethylsilyl)ethoxymethyl chloride (SEMCl) (1.0 mL, 5.6 mmol), K$_2$CO$_3$ (1.4 g, 10.4 mmol), and DMF (7 mL) was stirred for 10 h at 80° C. The mixture was diluted with EtOAc (20 mL) and washed with water (20 mL) and brine (20 mL) and the organic layer dried over MgSO$_4$ and concentrated. The title compound was eluted from a 20-g SPE cartridge (silica) with 50% EtOAc/hexane to give 0.66 g (60%) of a colorless oil. Mass spectrum (ESI, m/z): Calcd. for C$_{11}$H$_{20}$N$_2$O$_3$Si, 257.1 (M+H), found 257.0.

b) 2-Bromo-1-(2-trimethylsilanyl-ethoxymethyl)-1H-imidazole-4-carboxylic acid methyl ester

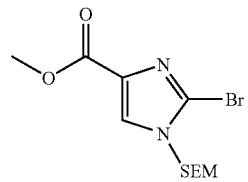

To a solution of 1-(2-trimethylsilanyl-ethoxymethyl)-1H-imidazole-4-carboxylic acid methyl ester (0.43 g, 1.6 mmol) (as prepared in the previous step) in CCl$_4$ (10 mL) was added NBS (0.30 g, 1.7 mmol) and AIBN (cat) and the mixture heated at 60° C. for 4 h. The reaction was diluted with EtOAc (30 ml) and washed with satd NaHCO$_3$ (2×30 mL) and brine (30 mL) and the organic layer concentrated. The title compound was eluted from a 20-g SPE cartridge (silica) with 50% EtOAc/hexane to give 0.40 g (71%) of a yellow solid. Mass spectrum (ESI, m/z): Calcd. for C$_{11}$H$_{19}$BrN$_2$O$_3$Si, 335.0/337.0 (M+H), found 335.0/337.0.

c) 2-Formyl-1-(2-trimethylsilanyl-ethoxymethyl)-1H-imidazole-4-carboxylic acid methyl ester

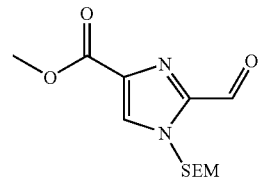

To a solution of 2-bromo-1-(2-trimethylsilanyl-ethoxymethyl)-1H-imidazole-4-carboxylic acid methyl ester (0.25 g, 0.74 mmol) (as prepared in the previous step) in THF (3 mL) at −40° C. was added dropwise a solution of 2M i-PrMgCl in THF (0.37 mL, 0.74 mmol). The reaction was allowed to stir for 10 min at −40° C. and then cooled to −78° C. and DMF (0.3 mL) was added. The reaction was allowed to attain RT and stirred for 1 h. The reaction was quenched with saturated NH$_4$Cl, diluted with EtOAc (10 mL) and washed with brine (2×10 mL) and the organic layer was concentrated. The title compound was eluted from a 10-g SPE cartridge (silica) with 50% EtOAc/hexane to give 0.11 g (53%) of a colorless oil. Mass spectrum (ESI, m/z): Calcd. for C$_{12}$H$_{20}$N$_2$O$_4$Si, 285.1 (M+H), found 284.7.

d) 2-Cyano-1-(2-trimethylsilanyl-ethoxymethyl)-1H-imidazole-4-carboxylic acid methyl ester

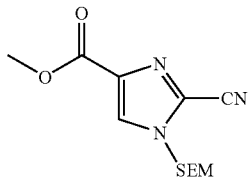

To a solution of 2-formyl-1-(2-trimethylsilanyl-ethoxymethyl)-1H-imidazole-4-carboxylic acid methyl ester (0.11 g, 0.38 mmol) (as prepared in the previous step) in methanol (2 mL) was added a 50% aqueous hydroxylamine solution (30 μL) and the reaction stirred for 3 h at RT and then concentrated. The residue was dissolved in DCM (2 mL), pyridine (0.13 mL), and trifluoroacetic anhydride (0.17 mL, 1.1 mmol) was added and the reaction stirred for 10 h at RT. The reaction was diluted with EtOAc (10 mL) and washed with satd. NaHCO$_3$ (2×10 mL) and the organic layer dried over Na$_2$SO$_4$ and then concentrated. The title compound was eluted from a 10-g SPE cartridge (silica) with 30% EtOAc/hexane to give 0.085 g (76%) of a colorless oil. $^1$H-NMR (400 MHz, CDCl$_3$): δ 7.99 (s, 1H), 5.50 (s, 2H), 3.92 (s, 3H), 3.58 (m, 2H), 0.94 (m, 214), 0.00 (s, 9H).

e) 3H-Imidazole-2,4-dicarboxylic acid 2-amide 4-{[4-(4-methyl-piperazin-1-yl)-2-piperidin-1-yl-phenyl]-amide}trifluoroacetic acid salt To a solution of 2-cyano-1-(2-trimethylsilanyl-ethoxymethyl)-1H-imidazole-4-carboxylic acid methyl ester (85 mg, 0.30 mmol) (as prepared in the previous step) in EtOH was added 6M KOH (50 μL) and the reaction stirred for 1 h at RT and then concentrated. The residue was dissolved in DMF (1 mL) and DMAP (34 mg, 0.30 mmol), EDCI (80 mg, 0.42 mmol) and 4-(4-methyl-piperazin-1-yl)-2-piperidin-1-yl-phenylamine (75 mg, 0.30 mmol) (as prepared in Example 5, step (b)) were added and the reaction stirred for 10 h at RT. The reaction was diluted with EtOAc (10 mL) and washed with brine (2×10 mL) and the organic layer dried (Na$_2$SO$_4$) and concentrated. The residue was dissolved in EtOH (0.3 mL) and 6N HCl (0.3 mL) and heated to 80° C. for 1 h. The reaction was concentrated and the title compound was purified by RP-HPLC (C18) eluting with 10-35% CH$_3$CN in 0.1% TFA/H$_2$O over 12 min to give 33 mg (21%) of the title compound. $^1$H-NMR (400 MHz, CH$_3$OD): δ 8.00 (s, 1H), 7.72 (d, 1H), 7.22 (s, 1H), 7.13 (d, 1H), 3.98 (m, 2H), 3.68 (m, 2H), 3.46 (m, 4H), 3.32 (m, 2H), 3.18 (m, 2H), 3.00 (s, 3H), 1.98 (m, 4H), 1.76 (m, 2H). Mass spectrum (ESI, m/z): Calcd. for C$_{21}$H$_{29}$N$_7$O$_2$, 412.2 (M+H), found 412.2.

Example 41

1H-Imidazole-2-carboxylic acid [3-chloro-4-(4-methyl-piperazin-1-yl)-2-piperidin-1-yl-phenyl]-amide bis(trifluoroacetic acid salt)

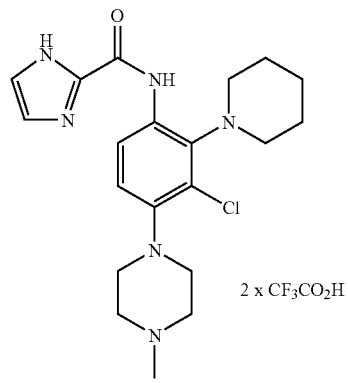

A flask was charged with 1H-imidazole-2-carboxylic acid [4-(4-methyl-piperazin-1-yl)-2-piperidin-1-yl-phenyl]-amide (14 mg, 0.020 μmmol) (as prepared in Example 39), N-chlorosuccinimide (6.0 mg, 0.020 μmol), acetic acid (25 μL), and CH$_3$CN (0.5 mL) and heated at 80° C. for 1 h. The reaction was concentrated and purified by RP-HPLC (C18), eluting with 10-35% CH$_3$CN in 0.1% TFA/H$_2$O over 12 min to give 5 mg (36%) of the title compound. $^1$H-NMR (400 MHz, CH$_3$OD): δ 8.42 (s, 1H), 7.32 (s, 2H), 7.06 (s, 1H), 3.68 (m, 2H), 3.54. (m, 2H), 3.38 (m, 2H), 3.12 (m, 2H), 3.02 (s, 3H), 2.92 (m, 4H), 1.92 (m, 4H), 1.70 (m, 2H). Mass spectrum (ESI, m/z): Calcd. for C$_{20}$H$_{27}$ClN$_6$O, 403.2 (M+H), found 403.1.

Example 42

4-[4-[2-(4-Cyano-1H-pyrrol-2-yl)-2-oxo-ethyl]-3-(4-methyl-piperidin-1-yl)-phenyl]-piperidine-1-carboxylic acid (2-dimethylamino-ethyl)-amide

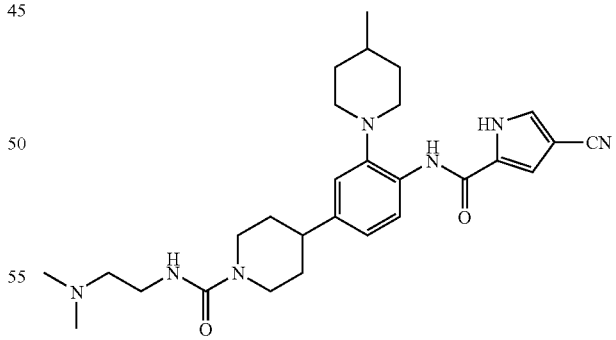

To a mixture of 4-cyano-1H-pyrrole-2-carboxylic acid [2-(4-methyl-piperidin-1-yl)-4-piperidin-4-yl-phenyl]-amide bis(trifluoroacetic acid salt) (as prepared in Example 35, 20.0 mg, 0.0323 mmol) and anh K$_2$CO$_3$ (22 mg, 0.16 mmol) in 0.50 mL of DMF at −78° C. was added a solution of triphosgene (3.8 mg, 0.013 mmol) in 0.5 mL of DCM under Ar. The mixture was warmed to 0° C. and stirred for 3 min, then cooled to −78° C. again. N1,N1-dimethyl-ethane-1,2-diamine (14 µL, 0.13 mmol) was added. The solution was warmed to RT and stirred for 16 h under Ar. Treated with 30 mL of EtOAc, the mixture was washed with H₂O (3×10 mL), brine (10 mL) and dried (Na₂SO₄). Removal of the solvent in vacuo followed by flash chromatography of the residue on silica gel (0-10% MeOH/DCM) gave 7.5 mg (46%) of the title compound as a colorless oil: $^1$H-NMR (CDCl$_3$; 400 MHz): δ 11.0 (s, 1H), 9.15 (s, 1H), 8.28 (d, 1H, J=8.4 Hz), 7.46 (d, 1H, J=1.2 Hz), 7.03 (d, 1H, J=1.9 Hz), 6.98 (dd, 1H, J=8.4, 1.2 Hz), 6.86 (d, 1H, J=1.9 Hz), 5.47 (s, 1H), 4.10 (d, 2H, J=12.9 Hz), 3.40 (ddd, 2H, J=6.1, 5.2, 5.1 Hz), 2.94 (d, 2H, J=11.6 Hz), 2.83 (td, 2H, J=12.9, 1.9 Hz), 2.71 (td, 2H, J=11.7, 2.0 Hz), 2.53-2.66 (m, 3H), 2.33 (s, 6H), 1.77-1.89 (m, 4H), 1.53-1.68 (m, 3H), 1.33-1.44 (m, 2H), 1.08 (d, 3H, J=6.5 Hz). Mass spectrum (ESI, m/z): Calcd. for $C_{28}H_{39}N_7O_2$, 506.3 (M+H), found 506.2.

Example 43

4-Cyano-1H-pyrrole-2-carboxylic acid [4-[1-(imidazole-1-carbonyl)-piperidin-4-yl]-2-(4-methyl-piperidin-1-yl)-phenyl]-amide

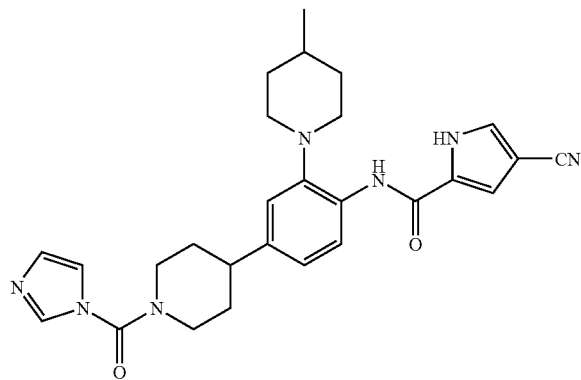

To a mixture of 4-cyano-1H-pyrrole-2-carboxylic acid [2-(4-methyl-piperidin-1-yl)-4-piperidin-4-yl-phenyl]-amide bis(trifluoroacetic acid salt) (as prepared in Example 35, 20.0 mg, 0.0320 mmol) and anh Na₂CO₃ (6.8 mg, 0.065 mmol) in 0.30 mL of DMF was added carbonyldiimidazole (11 mg, 0.068 mmol) in 0.3 mL of THF at RT. The mixture was stirred at RT for 2 h. Treated with 20 mL of EtOAc, the mixture was washed with H₂O, brine and dried with Na₂SO₄. Removal of the solvent under reduced pressure followed by flash chromatography of the residue on silica gel (1-5% MeOH/DCM) gave 14 mg (86%) of the title compound as a white solid: $^1$H-NMR (CDCl$_3$; 400 MHz): δ 10.7 (s, 1H), 9.16 (s, 1H), 8.33 (d, 1H, J=8.3 Hz), 7.95 (s, 1H), 7.47 (s, 1H), 7.13 (s, 1H), 7.06 (s, 1H), 7.03 (s, 1H), 6.88 (s, 1H), 4.28 (d, 2H, J=12.9 Hz), 3.16 (d, 2H, J=12.0 Hz), 2.97 (d, 2H, J=11.6 Hz), 2.71-2.84 (m, 3H), 1.99 (d, 2H, J=12.1 Hz), 1.87 (d, 2H, J=12.1 Hz), 1.71-1.83 (m, 2H), 1.65 (s, 1H), 1.54-1.65 (m, 1H), 1.34-1.48 (m, 2H), 1.10 (d, 3H, J=6.5 Hz). Mass spectrum (ESI, m/z): Calcd. for $C_{27}H_{31}N_7O_2$, 486.2 (M+H), found 486.0.

Example 44

4-Cyano-1H-pyrrole-2-carboxylic acid {2-(4-methyl-piperidin-1-yl)-4-[1-(pyridine-3-carbonyl)-piperidin-4-yl]-phenyl}-amide

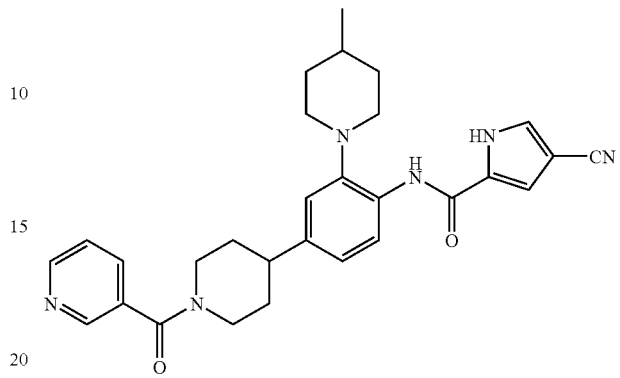

A mixture of 4-cyano-1H-pyrrole-2-carboxylic acid [2-(4-methyl-piperidin-1-yl)-4-piperidin-4-yl-phenyl]-amide bis (trifluoroacetic acid salt) (as prepared in Example 35, 25.0 mg, 0.0400 mmol), nicotinoyl chloride (10.8 mg, 0.0600 mmol) and anh Na₂CO₃ (21.0 mg, 0.200 mmol) in 1 mL of DMF was stirred at RT for 2 days. Treated with 30 mL of EtOAc, the mixture was washed with H₂O (3×10 mL), brine (10 mL) and dried (Na₂SO₄). Removal of the solvent under reduced pressure followed by flash chromatography of the residue on silica gel (1-3% MeOH/DCM) gave 19.6 mg (98%) of the title compound as a white solid: $^1$H-NMR (CDCl$_3$; 400 MHz): δ 10.67, (s, 1H), 9.17 (s, 1H), 8.74 (d, 1H, J=1.6 Hz), 8.69 (dd, 1H, J=4.5, 1.6 Hz), 8.32 (d, 1H, J=8.4 Hz), 7.82 (ddd, 1H, J=7.7, 1.9, 1.9 Hz), 7.47 (dd, 1H, J=3.3, 1.2 Hz), 7.40 (dd, 1H, J=8.0, 4.9 Hz), 7.07 (d, 1H, J=1.9 Hz), 7.04 (dd, 1H, J=8.4, 1.9 Hz), 6.87 (s, 1H), 4.90 (s, 1H), 3.87 (s, 1H), 3.22 (s, 1H), 2.69-3.00 (m, 6H), 1.53-2.06 (m, 7H), 1.35-1.46 (m, 2H), 1.00 (d, 3H, J=6.5 Hz). Mass spectrum (ESI, m/z): Calcd. for $C_{29}H_{32}N_6O_2$, 497.3 (M+H), found 497.2.

Example 45

4-Cyano-1H-pyrrole-2-carboxylic acid [4-[1-(2-dimethylamino-acetyl)-piperidin-4-yl]-2-(4-methyl-piperidin-1-yl)-phenyl]-amide

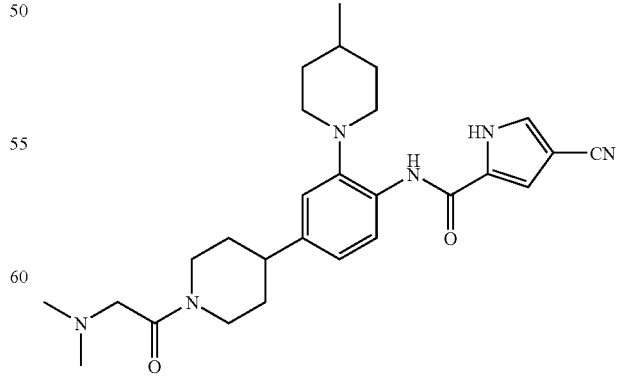

A mixture of 4-cyano-1H-pyrrole-2-carboxylic acid [2-(4-methyl-piperidin-1-yl)-4-piperidin-4-yl-phenyl]-amide bis (trifluoroacetic acid salt) (as prepared in Example 35, 20.0 mg, 0.0320 mmol) in 2 mL of 1:1 1N NaOH/MeOH solution was stirred at RT for 1 h. Treated with 20 mL of EtOAc, the mixture was washed with H$_2$O (3×5 mL). The aqueous layers were extracted with EtOAc (2×5 mL). The combined organic layers were washed with brine (10 mL), dried (Na$_2$SO$_4$) and concentrated in vacuo to give a white solid. The solid was added to a mixture of N,N-dimethylglycine (5.0 mg, 0.048 mmol), EDCI (9.2 mg, 0.048 mmol), HOBt (6.5 mg, 0.048 mmol) and DIEA (16.7 µL, 0.096 mmol) in 0.80 mL of DCM. The resulting mixture was stirred at RT for 4 h. Treated with 30 mL of EtOAc, the mixture was washed with H$_2$O (3×5 mL), brine (5 mL) and dried (Na$_2$SO$_4$). Removal of the solvent under reduced pressure followed by flash chromatography of the residue on silica gel (1-5% MeOH/DCM) gave 12 mg (78%) of the title compound as a white solid: $^1$H-NMR (CDCl$_3$; 400 MHz): δ 11.0 (s, 1H), 9.17 (s, 1H), 8.31 (d, 1H, J=8.4 Hz), 7.48 (d, 1H, J=1.3 Hz), 7.05 (d, 1H, J=1.8 Hz), 7.01 (dd, 1H, J=8.4, 1.8 Hz), 6.87 (d, 1H, J=1.3 Hz), 4.77 (d, 1H, J=13.3 Hz), 4.24 (d, 1H, J=13.3 Hz), 3.07-3.25 (m, 3H), 2.96 (d, 2H, J=11.8 Hz), 2.61-2.77 (m, 4H), 2.33 (s, 6H), 1.82-1.94 (m, 4H), 1.53-1.70 (m, 3H), 1.32-1.47 (m, 2H), 1.09 (d, 3H, J=6.5 Hz). Mass spectrum (ESI, m/z): Calcd. for C$_{27}$H$_{36}$N$_6$O$_2$, 477.3 (M+H), found 477.2.

Example 46

4-Cyano-1H-pyrrole-2-carboxylic acid (2-(4-methyl-piperidin-1-yl)-4-[1-(2,2,2-trifluoroethyl)-piperidin-4-yl]-phenyl)-amide

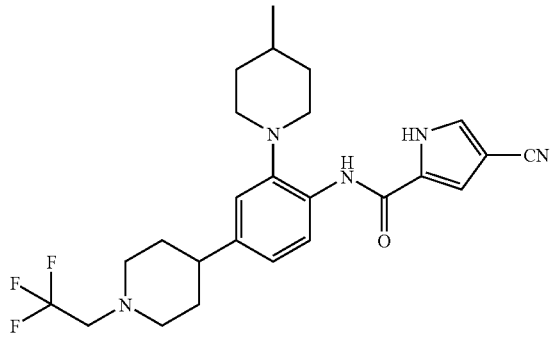

A mixture of 4-cyano-1H-pyrrole-2-carboxylic acid [2-(4-methyl-piperidin-1-yl)-4-piperidin-4-yl-phenyl]-amide bis (trifluoroacetic acid salt) (as prepared in Example 35, 25 mg, 0.040 mmol), trifluoromethanesulfonic acid 2,2,2-trifluoroethyl ester (9.8 mg, 0.042 mmol) and Na$_2$CO$_3$ (21 mg, 0.20 mmol) in 1 mL of DMF was stirred at RT for 8 h. Treated with 30 mL of EtOAc, the mixture was washed with H$_2$O (2×10 mL), brine (10 mL) and dried (Na$_2$SO$_4$). Removal of the solvent under reduced pressure followed by flash chromatography of the residue on silica gel (40% EtOAc/hexane) gave 11 mg (55%) of the title compound as a white solid: $^1$H-NMR (CDCl$_3$; 400 MHz): δ 10.7 (s, 1H), 9.20 (s, 1H), 8.29 (d, 1H, J=8.4 Hz), 7.47 (dd, 1H, J=3.1, 1.4 Hz), 7.10 (d, 1H, J=1.8 Hz), 7.04 (dd, 1H, J=8.4, 1.8 Hz), 6.87 (dd, 1H, J=3.1, 1.4 Hz), 2.90-3.14 (m, 6H), 2.72 (dd, 2H, J=11.5, 11.5 Hz), 2.41-2.52 (m, 3H), 1.74-1.90 (m, 6H), 1.60 (br s, 1H), 1.34-1.44 (m, 2H), 1.09 (d, 3H, J=6.5 Hz). Mass spectrum (ESI, m/z): Calcd. for C$_{25}$H$_{30}$F$_3$N$_5$O, 474.2 (M+H), found 474.1.

Example 47

4-Cyano-1H-imidazole-2-carboxylic acid [4-(1,1-dioxo-hexahydro-1λ$^6$-thiopyran-4-yl)-2-(4-methyl-piperidin-1-yl)-phenyl]-amide

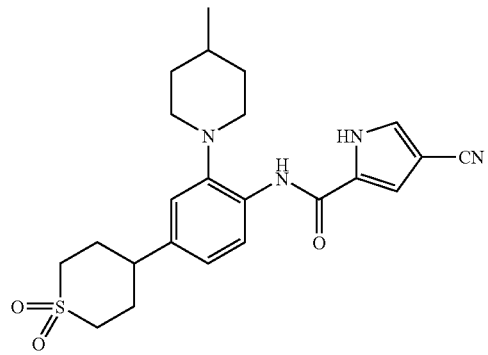

a) Trifluoromethanesulfonic acid 3,6-dihydro-2H-thiopyran-4-yl ester

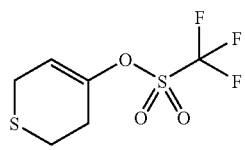

A solution of tetrahydro-thiopyran-4-one (1.00 g, 8.61 mmol) in 10 ml of THF was added to a solution of LDA (2.0 M, 4.52 ml, 9.04 mmol) in 20 ml of THF at −78° C. under Ar. The mixture was warmed to RT and stirred for 0.5 h, then cooled to −78° C. again. A solution of N-phenyltrifluoromethanesulfonimide (3.42 g, 9.47 mmol) in 10 mL of THF was added. The resulting mixture was warmed to RT and stirred for 0.5 h under Ar. Treated with 200 ml of EtOAc, the mixture was washed with H$_2$O (3×50 mL), brine (50 mL) and dried (Na$_2$SO$_4$). Removal of the solvent under reduced pressure followed by flash chromatography of the residue on silica gel (hexane-3% EtOAc/hexane) gave 810 mg (38%) of the title compound as a colorless oil: $^1$H-NMR (CDCl$_3$; 400 MHz): δ 6.01 (m, 1H), 3.30 (m, 2H), 2.86 (dd, 2H, J=5.7, 5.7 Hz), 2.58-2.64 (m, 2H). Mass spectrum (ESI, m/z): Calcd. for C$_6$H$_7$F$_3$O$_3$S$_2$, 249.0 (M+H), found 249.3.

b) 1-[5-(3,6-Dihydro-2H-thiopyran-4-yl)-2-nitro-phenyl]-4-methyl-piperidine

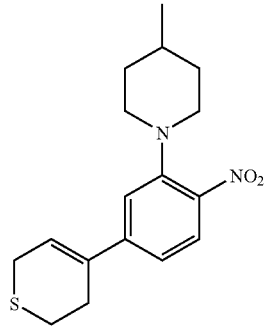

To a mixture of 1-[5-(5,5-dimethyl-[1,3,2]dioxaborinan-2-yl)-2-nitro-phenyl]-4-methyl-piperidine (as prepared in Example 33, step (b), 60 mg, 0.18 mmol), trifluoromethanesulfonic acid 3,6-dihydro-2H-thiopyran-4-yl ester (as prepared in the previous step, 54 mg, 0.22 mmol), Pd(PPh$_3$)$_4$ (31 mg, 0.027 mmol) and LiCl (15 mg, 0.36 mmol) in 1 mL of 1,4-dioxane was added 2.0 M Na$_2$CO$_3$ aq solution (80 μL, 0.16 mmol). The resulting mixture was stirred at 80° C. for 1 h, and then cooled to RT. Treated with 50 mL of EtOAc, the mixture was washed with H$_2$O, brine and dried (Na$_2$SO$_4$). Removal of the solvent under reduced pressure followed by flash chromatography of the residue on silica gel (1% EtOAc/hexane) gave 56 mg (97%) of the title compound as a brown oil: $^1$H-NMR (CDCl$_3$; 400 MHz): δ 7.77 (d, 1H, J=8.6 Hz), 7.01 (d, 1H, J=1.8 Hz), 6.88 (dd, 1H, J=8.6, 1.8 Hz), 6.24 (m, 1H), 3.34-3.37 (m, 2H), 3.26 (d, 2H, J=12.4 Hz), 2.89 (t, 2H, J=5.7 Hz), 2.82 (td, 2H, J=12.0, 1.6 Hz), 2.64-2.69 (m, 2H), 1.70 (dd, 2H, J=12.4, 2.1 Hz), 1.52 (m, 1H), 1.36-1.47 (m, 2H), 0.99 (d, 3H, J=6.2 Hz). Mass spectrum (ESI, m/z): Calcd. for C$_{17}$H$_{22}$N$_2$O$_2$S, 319.1 (M+H), found 319.1.

c) 1-[5-(1,1-Dioxo-1,2,3,6-tetrahydro-1λ$^6$-thiopyran-4-yl)-2-nitro-phenyl]-4-methyl-piperidine

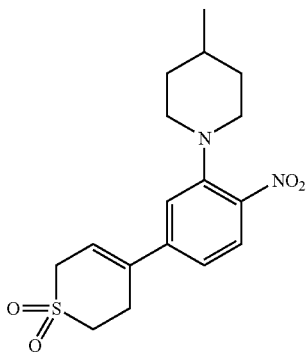

A mixture of 3-chloroperoxybenzoic acid (77 mg, 0.35 mmol, 77%) in 2 mL of DCM was added slowly to a solution of 1-[5-(3,6-dihydro-2H-thiopyran-4-yl)-2-nitro-phenyl]-4-methyl-piperidine (as prepared in the previous step, 50 mg, 0.16 mmol) in 2 mL of DCM at −78° C. under Ar. The mixture was stirred at −78° C. for 0.5 h, and then Warmed to RT. Treated with 2 mL of 10% Na$_2$SO$_3$ solution, the mixture was stirred vigorously for 5 min. The mixture was treated with 30 mL of EtOAc and 10 mL of H$_2$O. The aqueous layer was separated and the organic layer was washed with saturated aq NaHCO$_3$ solution (10 mL), H$_2$O (10 mL) and dried (Na$_2$SO$_4$). Removal of the solvent under reduced pressure followed by flash chromatography of the residue on silica gel (0-2% EtOAc/DCM) gave 35 mg (64%) of the title compound as a yellow oil: $^1$H-NMR (CDCl$_3$; 400 MHz): δ 7.77 (d, 1H, J=8.6 Hz), 7.00 (d, 1H, J=1.9 Hz), 6.88 (dd, 1H, J=8.6, 1.9 Hz), 5.93 (m, 1H), 3.83 (br s, 2H), 3.24-3.30 (m, 4H), 3.11-3.17 (m, 2H), 2.83 (ddd, 2H, J=12.0, 12.0, 2.3 Hz), 1.72 (dd, 2H, J=12.6, 2.3 Hz), 1.53 (m, 1H), 1.35-1.47 (m, 2H), 1.00 (d, 3H, J=6.3 Hz). Mass spectrum (ESI, m/z): Calcd. for C$_{17}$H$_{22}$N$_2$O$_4$S, 351.1 (M+H), found 351.0.

d) 4-(1,1-Dioxo-hexahydro-1λ$^6$-thiopyran-4-yl)-2-(4-methyl-piperidin-1-yl)-phenylamine

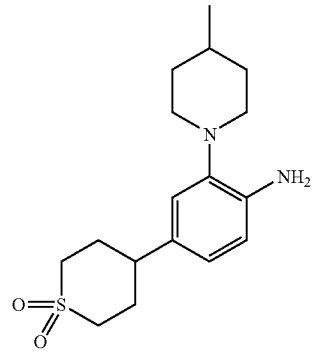

A mixture of 1-[5-(1,1-dioxo-1,2,3,6-tetrahydro-1λ$^6$-thiopyran-4-yl)-2-nitro-phenyl]-4-methyl-piperidine (as prepared in the previous step, 65 mg, 0.19 mmol) and 10% Pd/C (40 mg) in 3 mL of MeOH was stirred at RT under H$_2$ (balloon pressure) for 1 h. The Pd catalyst was removed by filtration on Celite and the filtrate was concentrated to give a white solid. Flash chromatography of the compound on silica gel (5% EtOAc/DCM) gave 42 mg (70%) of the title compound as a white solid: $^1$H-NMR (CDCl$_3$; 400 MHz): δ 6.82 (s, 1H), 6.76 (d, 1H, J=8.2 Hz), 6.68 (d, 1H, J=8.2 Hz), 3.91 (s, 2H), 3.05-3.16 (m, 6H), 2.67 (dddd, 2H, J=12.0, 12.0, 3.2, 3.2 Hz), 2.57 (dd, 2H, J=11.6, 11.6 Hz), 2.36 (m, 2H), 2.14-2.23 (m, 2H), 1.71-1.79 (m, 2H), 1.51 (m, 1H), 1.24-1.40 (m, 2H), 0.99 (d, 3H, J=6.6 Hz). Mass spectrum (ESI, m/z): Calcd. for C$_{17}$H$_{26}$N$_2$O$_2$S, 323.2 (M+H), found 323.2.

e) 4-Cyano-1-(2-trimethylsilanyl-ethoxymethyl)-1H-imidazole-2-carboxylic acid [4-(1,1-dioxo-hexahydro-1λ$^6$-thiopyran-4-yl)-2-(4-methyl-piperidin-1-phenyl]-amide

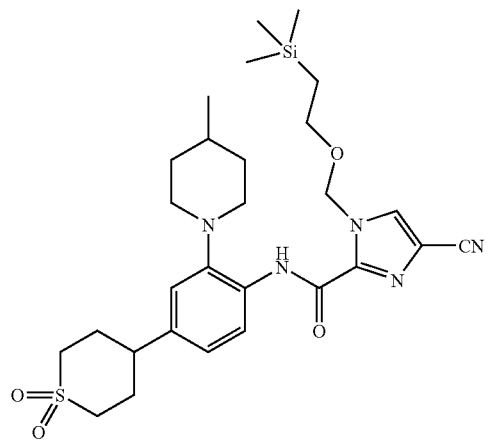

To a mixture of 4-(1,1-dioxo-hexahydro-1λ$^6$-thiopyran-4-yl)-2-(4-methyl-piperidin-1-yl)-phenylamine (as prepared in the previous step, 16 mg, 0.050 mmol), 4-cyano-1-(2-trimethylsilanyl-ethoxymethyl)-1H-imidazole-2-carboxylate potassium (as prepared in Example 3, step (d), 17 mg, 0.055 mmol) and PyBroP (35 mg, 0.075 mmol) in 1 mL of DCM was added DIEA (17 μL, 0.10 mmol). The resulting mixture was stirred at RT for 20 h under Ar. Treated with 30 mL of EtOAc, the mixture was washed with H$_2$O (3×10 mL), brine (10 mL) and dried (Na$_2$SO$_4$). Removal of the solvent under reduced pressure followed by flash chromatography of the residue on silica gel (1-2% EtOAc/DCM) gave 19 mg (68%) of the title compound as a colorless oil: $^1$H-NMR (CDCl$_3$; 400 MHz): δ 10.4 (s, 1H), 8.29 (d, 1H, J=8.4 Hz), 7.79 (s, 1H), 7.02 (d, 1H, J=1.9 Hz), 6.99 (dd, 1H, J=8.4, 1.9 Hz), 5.97 (s, 2H), 3.67 (app t, 2H, J=8.3 Hz), 3.14 (m, 4H), 2.99 (d, 2H, J=12.0 Hz), 2.67-2.80 (m, 3H), 2.40 (m, 2H), 2.22 (m, 2H), 1.79 (m, 2H), 1.52-1.67 (m, 3H), 1.08 (d, 3H, J=5.9 Hz), 0.98 (app t, 2H, J=8.3 Hz), 0.001 (s, 9H). Mass spectrum (ESI, m/z): Calcd. for C$_{28}$H$_{41}$N$_5$O$_4$SSi, 572.3 (M+H), found 572.0.

f) 4-Cyano-1H-imidazole-2-carboxylic acid [4-(1,1-dioxo-hexahydro-1λ$^6$-thiopyran-4-yl)-2-(4-methyl-piperidin-1-yl)-phenyl]-amide A solution of 4-cyano-1-(2-trimethylsilanyl-ethoxymethyl)-1H-imidazole-2-carboxylic acid [4-(1,1-dioxo-hexahydro-1λ$^6$-thiopyran-4-yl)-2-(4-methyl-piperidin-1-yl)-phenyl]-amide (as prepared in the previous step, 19.0 mg, 0.0330 mmol) in 1 mL of 2:1 TFA/DCM was stirred at RT for 4 h. Removal of the solvent under reduced pressure followed by flash chromatography of the residue on silica gel (10-20% EtOAc/DCM) gave 13.2 mg (90%) of the title compound as a white solid: $^1$H-NMR (CDCl$_3$; 400 MHz): δ 12.00 (s, 1H), 10.29 (s, 1H), 8.33 (d, 1H, J=8.3 Hz), 7.76 (d, 1H, J=2.3 Hz), 7.12 (dd, 1H, J=8.3, 1.7 Hz), 7.06 (d, 1H, J=1.7 Hz), 3.14-3.22 (m, 4H), 3.01 (d, 2H, J=12.0 Hz), 2.68-2.83 (m, 3H), 2.38-2.53 (m, 2H), 2.23 (d, 2H, J=14.5 Hz), 1.50-1.85 (m, 5H), 1.09 (d, 3H, J=5.8 Hz). Mass spectrum (ESI, m/z): Calcd. for C$_{22}$H$_{27}$N$_5$O$_3$S, 442.2 (M+H), found 442.2.

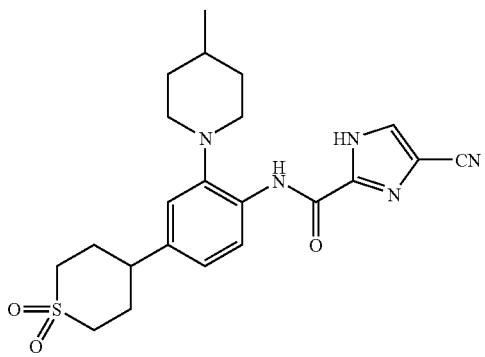

The following compounds have been prepared according to the examples as indicated:

| Example | Structure | Mass Spectrum Calcd [M + H]$^+$ | Mass Spectrum Found [M + H]+ | Formula | Proc. of Ex |
|---|---|---|---|---|---|
| 48 | 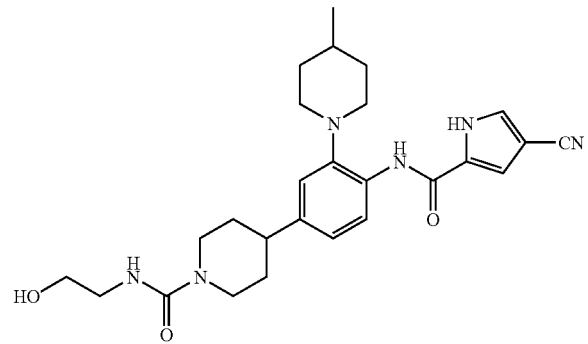 | 479.3 | 479.2 | C$_{26}$H$_{34}$N$_6$O$_3$ | 42 |

4-[4-[(4-Cyano-1H-pyrrole-2-carbonyl)-amino]-3-(4-methyl-piperidin-1-yl)-phenyl]-piperidine-1-carboxylic acid (2-hydroxy-ethyl)-amide

| | | | | | |
|---|---|---|---|---|---|
| 49 | 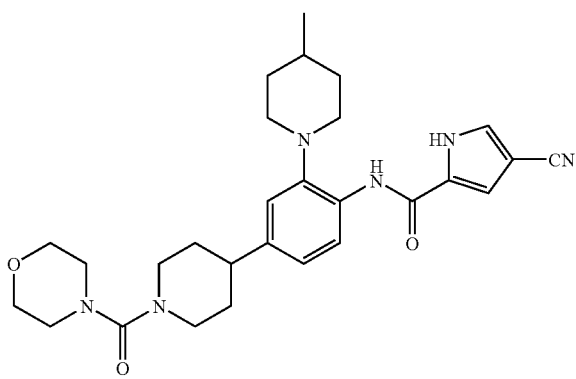<br>4-Cyano-1H-pyrrole-2-carboxylic acid<br>{2-(4-methyl-piperidin-1-yl)-4-[1-<br>(morpholine-4-carbonyl)-piperidin-4-yl]-phenyl}-amide | 505.3 | 505.2 | $C_{26}H_{36}N_6O_3$ | 42 |
| 50 | 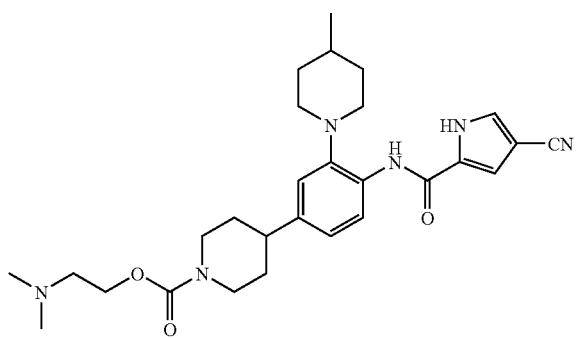<br>4-[4-[(4-Cyano-1H-pyrrole-2-carbonyl)-amino]-<br>3-(4-methyl-piperidin-1-yl)-phenyl]-<br>piperidine-1-carboxylic acid 2-dimethylamino-ethyl ester | 507.3 | 507.1 | $C_{28}H_{38}N_6O_3$ | 42 |
| 51 | 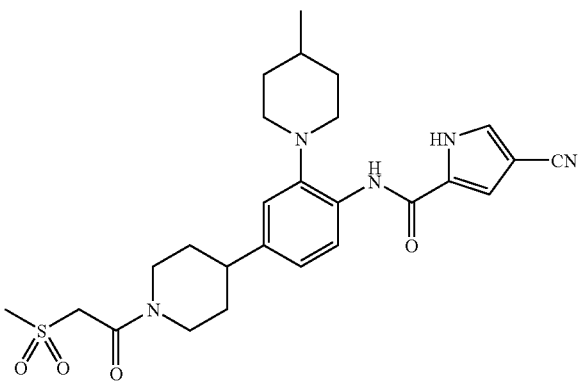<br>4-Cyano-1H-pyrrole-2-carboxylic acid<br>[4-[1-(2-methanesulfonyl-acetyl)-piperidin-<br>4-yl]-2-(4-methyl-piperidin-1-yl)-phenyl]-amide | 512.2 | 512.2 | $C_{26}H_{33}N_5O_4S$ | 45 |

| 52 | 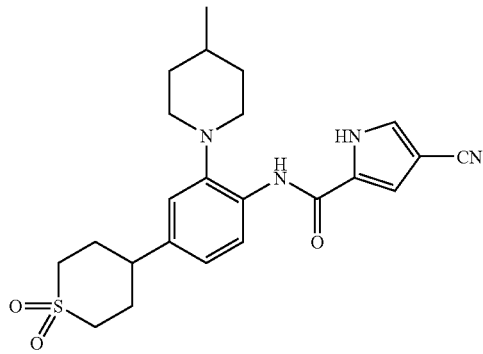 4-Cyano-1H-pyrrole-2-carboxylic acid [4-(1,1-dioxo-hexahydro-1λ⁶-thiopyran-4-yl)-2-(4-methyl-piperidin-1-yl)-phenyl]-amide | 441.2 | 441.1 | $C_{23}H_{28}N_4O_3S$ | 47 steps a-f |

Example 53

4-Cyano-1H-pyrrole-2-carboxylic acid [4-(4-methyl-piperazin-1-yl)-2-piperidin-1-yl-phenyl]-amide

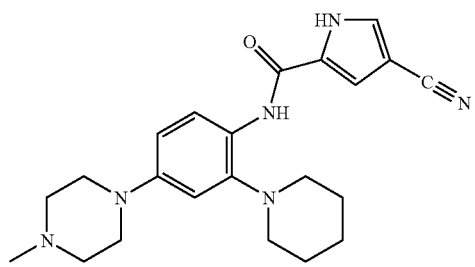

To 62 mg (0.44 mmol) of 4-cyano-1H-pyrrole-2-carboxylic acid (as prepared in Example 2) in dichloromethane (20 mL) was added 1-(3-dimethylaminopropyl)-3-ethylcarbodiimide hydrochloride (EDCI) (107 mg, 0.560 mmol), hydroxybenzotriazole (HOBt) (65 mg, 0.48 mmol), and 4-(4-methyl-piperazin-1-yl)-2-piperidin-1-yl-phenylamine (as prepared in Example 5, step (b), 100 mg, 0.370 mmol) and the mixture stirred for 24 h at RT. The mixture was poured into satd aq sodium bicarbonate (50 mL) and extracted with dichloromethane (2×20 mL). The organic layers were washed with brine (20 mL), dried over $Na_2SO_4$ and the solvent was removed in vacuo. Purification of the resulting residue by silica gel preparative TLC eluting with 10% methanol in dichloromethane yielded 63 mg (44%) of the title compound as a tan solid. ¹H-NMR (400 MHz, CDCl₃): δ 11.09 (br s, 1H), 9.11 (s, 1H), 8.25 (d, 1H, J=8.9 Hz), 7.45 (d, 1H, J=1.3 Hz), 6.88 (d, 1H, J=1.1 Hz), 6.81 (d, 1H, J=2.6 Hz), 6.75 (dd, 1H, J=8.9, 2.6), 3.21 (m, 4H), 2.84 (m, 4H), 2.62 (m, 4H), 2.38 (s, 3H), 1.78 (m, 5H). LC-MS (ESI, m/z): Calcd. for $C_{22}H_{29}N_6O$, 393.2 (M+H); found: 393.2.

Example 54

4-Cyano-1H-pyrrole-2-carboxylic acid [4-(4-methyl-piperazin-1-yl)-2-(4-methyl-piperidin-1-yl)-phenyl]-amide

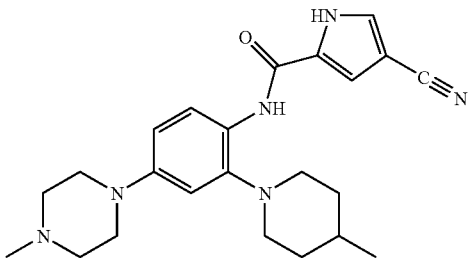

The procedure of Example 53 was followed using 4-cyano-1H-pyrrole-2-carboxylic acid (as prepared in Example 2, 56 mg, 0.22 mmol) and 4-(4-methyl-piperazin-1-yl)-2-(4-methyl-piperidin-1-yl)-phenylamine (as prepared in Example 13, step (a), 61 mg 0.21 mmol). Purification of the resulting residue by silica gel preparative TLC eluting with 10% methanol in dichloromethane yielded 47 mg (55%) of the title compound as an off-white solid. ¹H-NMR (400 MHz, CDCl₃): δ 9.60 (br s, 1H), 8.30 (d, 1H, J=8.9), 7.24 (d, 1H, J=3.7 Hz), 7.21 (d, 1H, J=3.7 Hz), 6.79 (d, 1H, J=2.7 Hz), 6.73 (dd, 1H, J=8.9, 2.7 Hz), 3.20 (m, 4H), 3.00-2.97 (m, 2H), 2.76-2.70 (m, 2H), 2.59 (m, 4H), 2.37 (s, 3H), 1.85-1.82 (m, 2H), 1.56-1.46 (m, 2H), 1.07 (d, 3H, J=6.2 Hz). LC-MS (ESI, m/z): Calcd. for $C_{23}H_{31}N_6O$, 407.3 (M+H); found: 407.2.

Example 55

5-Cyano-furan-2-carboxylic acid [4-methyl-6'-(4-methyl-piperazin-1-yl)-3,4,5,6-tetrahydro-2H-[1,2']bipyridinyl-3'-yl]-amide

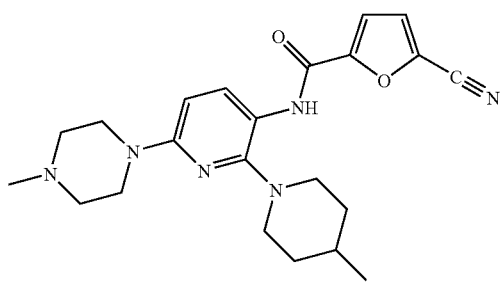

a) 6'-Chloro-4-methyl-3'-nitro-3,4,5,6-tetrahydro-2H-[1,2']bipyridinyl

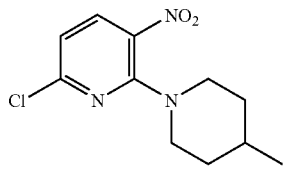

A flask was charged with 2,6-dichloro-3-nitropyridine (1.00 g, 5.00 mmol), absolute ethanol (25 mL), and 4-methylpiperidine (0.65 mL, 5.5 mmol) and stirred 15 h at RT. The solvents were removed in vacuo and purification of the resulting residue by silica gel preparative TLC eluting with 10% ethyl acetate in hexane yielded 577 mg (45%) of the title compound as a yellow glass. LC-MS (ESI, m/z): Calcd. for $C_{11}H_{15}ClN_3O_2$, 256.1/258.1 (M+H); found: 256.1/258.1.

b) 4-Methyl-6'-(4-methyl-piperazin-1-yl)-3'-nitro-3,4,5,6-tetrahydro-2H-[1,2']bipyridinyl

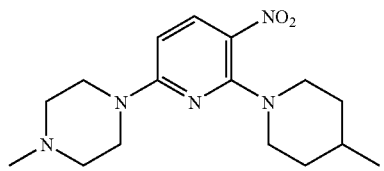

A flask was charged with 6'-chloro-4-methyl-3'-nitro-3,4,5,6-tetrahydro-2H-[1,2']bipyridinyl (210 mg, 0.820 mmol) (as prepared in the previous step), and 1-methylpiperazine (182 µL, 1.65 mmol) and the mixture was stirred at 145° C. for 3 h. Purification of the resulting residue by silica gel preparative TLC eluting with 10% methanol in dichloromethane yielded 202 mg (77%) of the title compound as yellow glass. $^1$H-NMR (400 MHz, CDCl$_3$): δ 8.19 (d, 1H, J=9.2 Hz), 6.03 (d, 1H, J=9.2 Hz), 3.82 (m, 2H), 3.70 (m, 4H), 2.98 (m, 2H), 2.48 (m, 2H), 2.34 (s, 3H), 1.71-1.60 (m, 3), 1.35 (m, 2H), 0.97 (d, 3H, J=6.3 Hz). LC-MS (ESI, m/z): Calcd. for $C_{16}H_{26}N_5O_2$, 320.2 (M+H); found: 320.1.

c) 4-Methyl-6'-(4-methyl-piperazin-1-yl)-3,4,5,6-tetrahydro-2H-[1,2']bipyridinyl-3'-ylamine

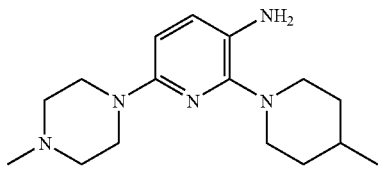

A flask was charged with 4-methyl-6'-(4-methyl-piperazin-1-yl)-3'-nitro-3,4,5,6-tetrahydro-2H-[1,2']bipyridinyl (101 mg, 0.320 mmol), methanol (10 mL), ammonium chloride (171 mg, 3.20 mmol), and iron powder (88 mg, 1.6 mmol) and refluxed for 10 h. Additional amounts of ammonium chloride (171 mg, 3.20 mmol) and iron powder (88 mg, 1.6 mmol) were added after 2.5 h and 6 h during the reflux operation. The cooled mixture was poured into satd aq sodium bicarbonate (100 mL), extracted with dichloromethane (4×20 mL), and the organic layers were dried over Na$_2$SO$_4$. The solvents were removed in vacuo to yield 80 mg (87%) of the title compound as a green glass. $^1$H-NMR (400 MHz, CDCl$_3$): δ 6.89 (d, 1H, J=8.3), 6.21 (d, 1H, J=8.3 Hz), 3.45-3.36 (m, 8H), 2.71 (m, 2H), 2.54 (m, 4H), 2.34 (s, 3H), 1.74-1.71 (m, 2H), 1.52 (m, 1H), 1.31 (m, 2H), 0.98 (d, 3H, J=6.5 Hz). LC-MS (ESI, m/z): Calcd. for $C_{16}H_{28}N_5$, 290.2 (M+H); found: 290.2.

d) 5-Cyano-furan-2-carboxylic acid [4-methyl-6'-(4-methyl-piperazin-1-yl)-3,4,5,6-tetrahydro-2H-[1,2]bipyridinyl-3'-yl]-amide The title compound was prepared according to the procedure from Example 4, step (c) using 2-cyano-5-furancarboxylic acid (as prepared in Example 1) and 4-methyl-6'-(4-methyl-piperazin-1-yl)-3,4,5,6-tetrahydro-2H-[1,2']bipyridinyl-3'-ylamine (as prepared in the previous step). Purification of the resulting residue by silica gel preparative TLC eluting with 10% methanol in dichloromethane afforded the title compound in 50% as a yellow glass. $^1$H-NMR (400 MHz, CDCl$_3$): δ 8.76 (br s, 1H), 8.410 (d, 1H, J=8.8 Hz), 7.24 (d, 1H, J=3.7 Hz), 7.21 (d, 1H, J=3.7 Hz), 6.37 (d, 1H, J=8.8 Hz), 3.53 (m, 4H), 3.21-3.18 (m, 2H), 2.85 (m, 2H), 2.52 (m, 4H), 2.34 (s, 3H), 1.82-1.79 (m, 2H), 1.57 (m, 1H), 1.47-1.37 (m, 2H) 1.05 (d, 3H, J=6.5 Hz). NOE 1H-NMR experiments confirmed the correct regiochemical assignment. LC-MS (ESI, m/z): Calcd. for $C_{22}H_{29}N_6O_2$, 409.2 (M+H); found: 409.2.

Example 56

4-Cyano-1H-pyrrole-2-carboxylic acid [2-(4-methyl-piperidin-1-yl)-4-piperazin-1-yl-phenyl]-amide bis (trifluoroacetic acid salt)

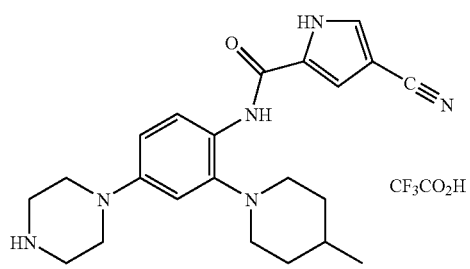

85 a) 4-[4-[(4-Cyano-1H-pyrrole-2-carbonyl)-amino]-3-(4-methyl-piperidin-1-yl)-phenyl]-piperazine-1-carboxylic acid tert-butyl ester

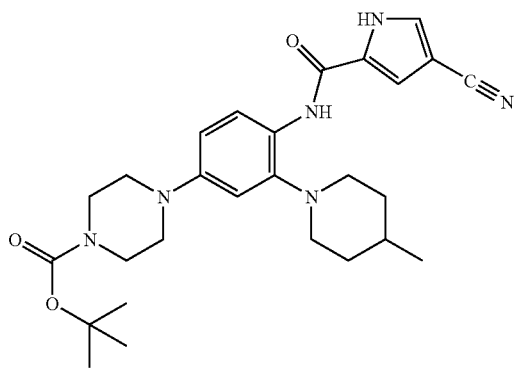

Prepared according to the procedure from Example 53 using 4-cyano-1H-pyrrole-2-carboxylic acid (as prepared in Example 2) and 4-[4-amino-3-(4-methyl-piperidin-1-yl)-phenyl]-piperazine-1-carboxylic acid tert-butyl ester as prepared in Example 15, step (c). Purification of the resulting residue by silica gel preparative TLC eluting with 20% ethyl acetate in dichloromethane afforded the title compound in 47% as an off-white solid. $^1$H-NMR (400 MHz, CDCl$_3$): δ 11.13 (br s, 1H), 9.05 (s, 1H), 8.29 (d, 1H, J=8.9), 7.48 (dd, 1H, J=3.0, 1.3 Hz), 6.88 (s, 1H), 6.84 (d, 1H, J=2.6 Hz), 6.76 (dd, 1H, J=8.9, 2.2 Hz), 3.62 (m, 4H), 3.13 (m, 4H), 3.01-2.98 (m, 2H), 2.73 (m, 2H), 1.88-1.85 (m, 2H), 1.61-1.56 (m, 2H), 1.51 (s, 9H), 1.50-1.37 (m, 2H), 1.10 (d, 3H, J=6.5 Hz). LC-MS (ESI, m/z): Calcd. for C$_{27}$H$_{37}$N$_6$O$_3$, 493.3 (M+H); found: 493.1.

b) 4-Cyano-1H-pyrrole-2-carboxylic acid [2-(4-methyl-piperidin-1-yl)-4-piperazin-1-yl-phenyl]-amide bis(trifluoroacetic acid salt)

To 4-[4-[(4-cyano-1H-pyrrole-2-carbonyl)-amino]-3-(4-methyl-piperidin-1-yl)-phenyl]-piperazine-1-carboxylic acid tert-butyl ester (80 mg, 0.16 mmol, as prepared in the previous step) in dichloromethane (2 mL) was added TFA (2 mL) and water (50 μL) and the mixture was stirred for 2 h at RT. The solvents were removed in vacuo and the resulting residue was purified by silica gel preparative TLC eluting with 10% methanol in dichloromethane yielding 92 mg (92%) of the title compound as an off-white solid. $^1$H-NMR (400 MHz, CDCl$_3$): δ 12.67 (br s, 1H), 9.04 (s, 1H), 8.72 (br s, 2H), 7.78 (d, 1H, J=1.5 Hz), 7.63 (d, 1H, J=8.4 Hz), 7.31 (s, 1H), 6.76 (d, 1H, J=2.6 Hz), 6.69 (dd, 1H, J=8.8, 2.6 Hz), 3.46-3.17 (m, 8H), 3.00-2.97 (m, 2H), 2.62 (m, 2H), 1.69-1.67 (m, 2H), 1.47 (m, 1H), 1.35 (m, 2H), 0.97 (d, 3H, J=6.3 Hz). LC-MS (ESI, m/z): Calcd. for C$_{22}$H$_{29}$N$_6$O, 393.2 (M+H); found: 393.1.

86

Example 57

4-Cyano-1H-pyrrole-2-carboxylic acid [4-(4-acetyl-piperazin-1-yl)-2-(4-methyl-piperidin-1-yl)-phenyl]-amide

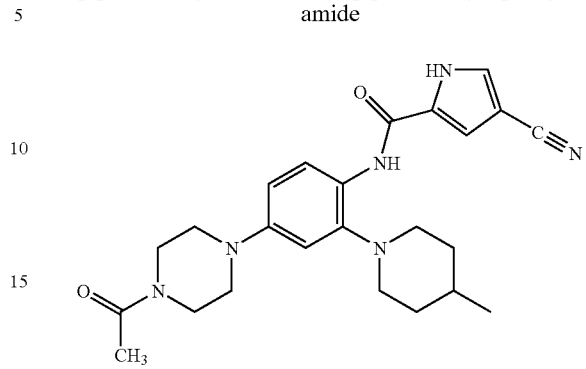

To 4-cyano-1H-pyrrole-2-carboxylic acid [2-(4-methyl-piperidin-1-yl)-4-piperazin-1-yl-phenyl]-amide trifluoroacetic acid salt (as prepared in Example 56, step (b)) (30 mg, 0.048 mmol) in dichloromethane (5 mL) was added acetic anhydride (7.0 μL, 0.072 mmol) and DIEA (31 μL, 0.18 mmol) and the mixture was stirred for 5 h at RT. The mixture was poured into saturated aq sodium bicarbonate (5 mL), extracted with dichloromethane (5 mL), and the organic layer was dried (Na$_2$SO$_4$). The solvents were removed in vacuo and the resulting residue was purified by silica gel preparative TLC eluting with 10% methanol in dichloromethane to yield 4.9 mg (23%) of the title compound as an off-white solid. $^1$H-NMR (400 MHz, CDCl$_3$): δ 10.57 (br s, 1H), 8.99 (s, 1H), 8.27 (d, 1H, J=8.8 Hz), 7.45 (dd, 1H, J=3.1, 1.3 Hz), 6.851 (s, 1H), 6.81 (d, 1H, J=3.5 Hz), 6.73 (dd, 1H, J=8.9, 2.6 Hz), 3.79 (m, 2H), 3.64 (m, 2H), 3.17-2.96 (m, 4H), 2.74 (m, 2H), 2.70 (m, 2H), 2.15 (s, 3H), 1.87-1.84 (m, 2H), 1.58 (m, 1H), 1.44-1.34 (m, 2H), 1.08 (d, 3H, J=6.5 Hz). LC-MS (ESI, m/z): Calcd. for C$_{24}$H$_{31}$N$_6$O$_2$, 435.2 (M+H); found: 435.1.

Example 58

4-Cyano-1H-pyrrole-2-carboxylic acid [4-methyl-6'-(4-methyl-piperazin-1-yl)-3,4,5,6-tetrahydro-2H-[1,2']bipyridinyl-3'-yl]-amide

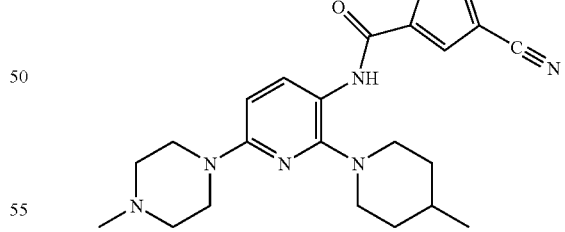

A flask was charged with 4-cyano-pyrrole-2-carboxylic acid (as prepared in Example 2, 200 mg, 1.43 mmol), dichloromethane (30 ml), DMF (150 μL), and oxalyl chloride (275 μL, 1.60 mmol) and the mixture was stirred for 20 min at RT. Toluene (10 mL) was then added and the solvents were removed in vacuo. To the resulting acid chloride, dichloromethane (30 mL), DIEA (750 μL, 4.30 mmol), and 4-methyl-6'-(4-methyl-piperazin-1-yl)-3,4,5,6-tetrahydro-2H-[1,2']bipyridinyl-3'-ylamine (as prepared in Example 55, step (c), 385 mg, 1.33 mmol) were added and the mixture was stirred at RT for 4 days. The mixture was poured into saturated aq sodium bicarbonate (100 mL), and extracted with dichloromethane (2×25 mL) and the solvents were removed in vacuo. Purification of the resulting residue by silica gel preparative TLC eluting with 10% methanol in dichloromethane, then repurification by alumina preparative TLC eluting with dichloromethane-acetonitrile-methanol (7:2.5:0.5) yielded 38 mg (7%) of the title compound as a green solid. $^1$H-NMR (400 MHz, CDCl$_3$): δ 11.32 (br s, 1H), 8.33 (d, 1H, J=8.8 Hz), 7.44 (s, 1H), 6.87 (s, 1H), 6.39 (d, 1H, J=8.8 Hz), 3.54 (m, 4H), 3.18-3.15 (m, 2H), 2.84 (m, 2H), 2.56 (m, 4H), 2.38 (s, 3H), 1.82-1.79 (m, 2H), 1.56 (m, 1H), 1.40-1.33 (m, 2H) 1.06 (d, 3H, J=6.5 Hz). LC-MS (ESI, m/z): Calcd. for $C_{22}H_{30}N_7O$, 408.2 (M+H); found: 408.2.

Example 59

5-Cyano-furan-2-carboxylic acid [2-(4-methyl-piperazin-1-yl)-4-(4-methyl-piperidin-1-yl)-pyrimidin-5-yl]-amide trifluoroacetic acid salt

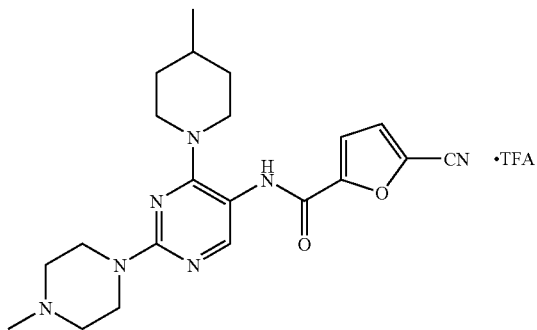

a) 2-Chloro-4-(4-methyl-piperidin-1-yl)-5-nitro-pyrimidine

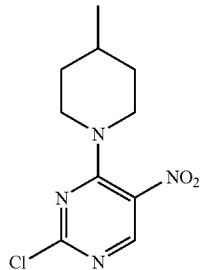

To a solution of 2,4-dichloro-5-nitropyrimidine (194 mg, 1.00 mmol) in THF (10 mL) at −40° C., 4-methylpiperidine (118 μL, 1.00 mmol) was added dropwise. The resulting mixture was stirred at −40° C. for 3 h and the solvent was removed in vacuo. The resulting yellow residue was chromatographed on silica (5-20% EtOAc:hexane) to obtain the title compound (103 mg, 40%). $^1$H-NMR (CDCl$_3$; 400 MHz): δ 8.69 (s, 1H), 4.24 (br m, 2H), 3.10 (m, 2H, J=12.9, 2.7 Hz), 1.82-1.71 (m, 3H), 1.36-1.25 (m, 2H), 1.01 (d, 3H, J=4.8 Hz).

b) 2-(4-Methyl-piperazin-1-yl)-4-(4-methyl-piperidin-1-yl)5-nitro-pyrimidine

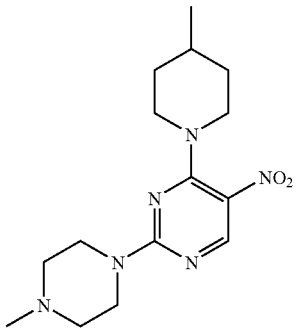

To a solution of 2-chloro-4-(4-methyl-piperidin-1-yl)-5-nitro-pyrimidine (as prepared in the previous step) (257 mg, 1.00 mmol) in DMF (10 mL) was added 1-methyl piperazine (110 μL, 1.00 mmol). The resulting mixture was heated at 80° C. for 48 h. The reaction mixture was allowed to cool to room temperature and partitioned between water/EtOAc. The EtOAc layer was separated, dried (Na$_2$SO$_4$) and concentrated in vacuo. The residue obtained was purified on silica (0-10% MeOH:EtOAc) to obtain the title compound (192 mg, 63%). $^1$H-NMR (CDCl$_3$; 400 MHz): δ 8.76 (s, 1H), 3.90 (br m, 6H), 2.96 (m, 2H), 2.40 (m, 4H), 2.32 (s, 3H), 1.82-1.6 (m, 3H), 1.2-1.3 (m, 2H), 1.02 (d, 3H, J=6.5 Hz).

c. 5-Cyano-furan-2-carboxylic acid[2-(4-methyl-piperazin-1-yl)-4-(4-methyl-piperidin-1-yl)-pyrimidin-5-yl]-amide trifluoroacetic acid salt

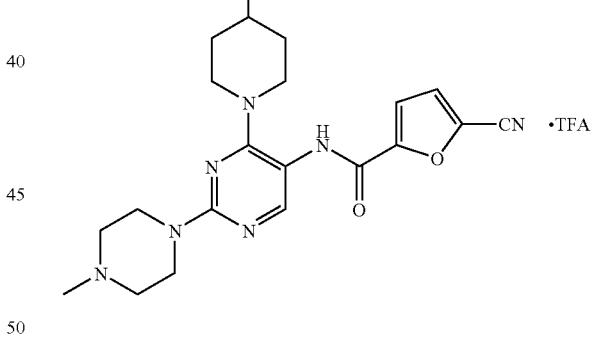

2-(4-Methyl-piperazin-1-yl)-4-(4-methyl-piperidin-1-yl)-5-nitro-pyrimidine (as prepared in the previous step) (320 mg, 1.00 mmol) was converted to corresponding amine according to the procedure in Example 55, step (c) and coupled with 5-cyano-furan-2-carbonyl chloride as prepared in Example 4, step (c) (obtained from 137 mg, 1.00 mmol of 5-cyano-furan-2-carboxylic acid as prepared in Example 1) in DMF (2 mL) at 0° C. The product was isolated by reversed-phase chromatography on C-18 column (eluting with 20-80% CH$_3$CN/1% TFA:H$_2$O) to obtain the title compound (28 mg, 6%). $^1$H-NMR (CDCl$_3$; 400 MHz): δ 9.79 (s, 1H), 8.05 (s, 1H), 7.31 (d, 1H, J=3.7 Hz), 7.18 (d, 1H, J=3.7 Hz), 6.08 (br m, 3H), 4.61 (m, 3H), 3.69 (br m, 3H),), 3.07 (m, 3H), 2.92 (s, 3H), 1.92-1.80 (m, 3H), 1.15-1.3 (m, 2H), 0.97 (d, 3H, J=6.3 Hz). LC-MS (ESI, m/z): Calcd. for $C_{21}H_{27}N_7O_2$, 410.2 (M+H), found 410.2.

Example 60

5-Cyano-furan-2-carboxylic acid[4-methyl-5'-(4-methyl-piperazin-1-yl)-3,4,5,6-tetrahydro-2H-[1,3']bipyridinyl-2'-yl]-amide

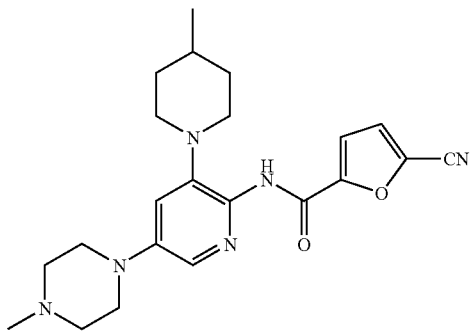

a) 3,5-dicholoro-2-nitro pyridine

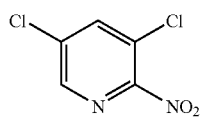

2-Amino-3,5-dichloropyridine (193 mg, 1.00 mmol) was dissolved in conc $H_2SO_4$ (5 mL) and $K_2S_2O_8$ (1.3 g, 5.0 mmol) was added portionwise. The resulting mixture was stirred at RT overnight and poured onto crushed ice and neutralized with satd aq $NaHCO_3$. The product was extracted with $CH_2Cl_2$ (3×20 mL), dried ($Na_2SO_4$) and concentrated in vacuo to obtain the title compound (123 mg, 63.7%). $^1$H-NMR (CDCl$_3$; 400 MHz): δ 8.40 (d, 1H, J=2.1 Hz), 8.05 (d, 1H, J=2.1 Hz).

d) 5'-Chloro-4-methyl-2'-nitro-3,4,5,6-tetrahydro-2H-[1,3']bipyridinyl

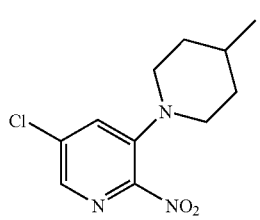

A mixture of 3,5-dichloro-2-nitropyridine (193 mg, 1.00 mmol), 4-methylpiperidine (118 μL, 1.00 mmol) and $K_2CO_3$ (138 mg, 1.00 mmol) in toluene (10 mL) was heated at 50° C. for 3 h. Toluene was removed in vacuo and the residue obtained was purified on silica (2% EtOAc/hexane) to obtain the title compound (153 mg, 60%). $^1$H-NMR (CDCl$_3$; 400 MHz): δ 7.95 (s, 1H, J=2.5 Hz), 7.58 (s, 1H, J=2.5 Hz), 3.30 (m, 2H), 2.95 (m, 2H), 1.87 (m; 2H), 1.65 (m, 1H), 1.35 (m, 2H), 1.0 (d, 3H, J=6.3 Hz).

c) 4-Methy-5'-(4-methyl-piperazin-1-yl)-2'-nitro-3,4,5,6-tetrahydro-2H-[1,3']bipyridinyl

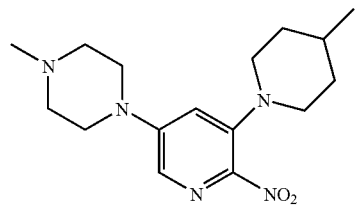

To a solution of 5'-chloro-4-methyl-2'-nitro-3,4,5,6-tetrahydro-2H-[1,3']bipyridinyl (as prepared in the previous step) (255 mg, 1.00 mmol) in DMF (10 mL) was added 1-methyl piperazine (110 μL, 1.00 mmol). The resulting mixture was heated at 125° C. overnight. The reaction mixture was allowed to cool to room temperature and partitioned between water and EtOAc. The EtOAc layer was separated, dried ($Na_2SO_4$) and concentrated in vacuo. The residue obtained was purified on silica (10-50% EtOAc:hexane) to obtain the title compound (204 mg, 64%). $^1$H-NMR (CDCl$_3$; 400 MHz): δ 7.67 (d, 1H, J=2.52 Hz), 6.69 (d, 1H, J=2.52 Hz), 3.39 (m, 4H), 3.29 (m, 2H), 2.75 (m, 2H), 2.56 (m, 4H), 2.35 (s, 3H), 1.71 (m, 2H), 1.6-1.5 (m, 3H), 0.99 (d, 3H, J=6.3 Hz).

d) 5-Cyano-furan-2-carboxylic acid[4-methyl-5'-(4-methyl-piperazin-1-yl)-3,4,5,6-tetrahydro-2H-[1,3']bipyridinyl-2'-yl]-amide

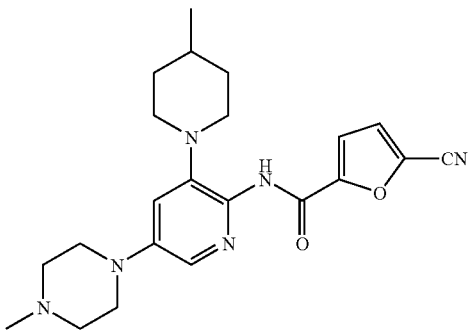

4-Methy-5'-(4-methyl-piperazin-1-yl)-2'-nitro-3,4,5,6-tetrahydro-2H-[1,3']bipyridinyl (as prepared in the previous step) (319 mg, 1.00 mmol) was converted to corresponding amine according to the procedure in Example 55, step (c) and coupled with 5-cyano-furan-2-carbonyl chloride as prepared in Example 4, step (c) (obtained from 137 mg, 1.00 mmol of 5-cyano-furan-2-carboxylic acid as prepared in Example 1) in DMF (2 mL) at 0° C. The product was isolated by flash chromatography on silica (20% EtOAc/hexane-10% MeOH/EtOAc) to obtain the title compound (16 mg, 4%). $^1$H-NMR (CDCl$_3$; 400 MHz): δ 9.35 (br s, 1H), 7.95 (br s, 1H), 7.33 (d, 1H, J=3.5 Hz), 7.22 (d, 1H), J=3.5 Hz), 7.06 (br s, 1H), 3.21 (m, 4H), 3.06 (m, 2H), 2.71 (m, 2H), 2.58 (m, 4H), 2.37 (s, 3H), 1.84 (m, 2H), 1.7-1.5 (m, 3H), 1.07 (d, 3H, J=6.3 Hz). LC-MS (ESI, m/z); Calcd. for $C_{22}H_{28}N_6O_2$, 409.2 (M+H), found 409.2.

Example 61

5-Cyano-furan-2-carboxylic acid[4-methyl-6'-(4-methyl-2-oxo-piperazin-1-yl)-3,4,5,6-tetrahydro-2H-[1,3']bipyridinyl-2'-yl]-amide

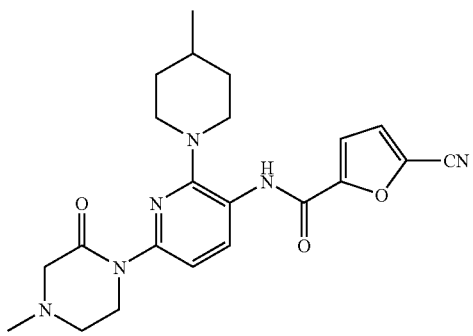

a) 6'-Bromo-4-methyl-3'-nitro-3,4,5,6-tetrahydro-2H-[1,2']bipyridinyl

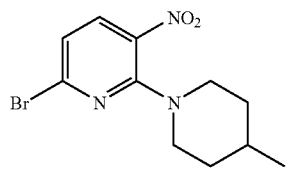

A mixture of 2,6-dibromo-3-nitropyridine (Duffy, J., et al, J. Org. Chem. 56, (9), 3006, (1991)) (282 mg, 1.00 mmol), 4-methylpiperidine (118 µL, 1.00 mmol) and $K_2CO_3$ (138 mg, 1.00 mmol) in toluene (10 mL) was heated at 50° C. for 3 h. Toluene was removed in vacuo and the residue obtained was purified on silica (2% EtOAc/hexane) to obtain the title compound (197 mg, 66%). $^1$H-NMR (CDCl$_3$; 400 MHz): δ 8.32 (d, 1H J=8.2 Hz), 7.94 (d, 1H J=8.2 Hz), 3.82 (m, 2H), 3.04 (m, 2H), 1.85 (m, 3H), 1.3 (m, 2H), 0.99 (d, 3H, J=6.4 Hz).

b) 4-Methyl-1-(4-methyl-3'-nitro-3,4,5,6-tetrahydro-2H-[1,2']bipyridinyl-6'-yl)-piperazin-2-one

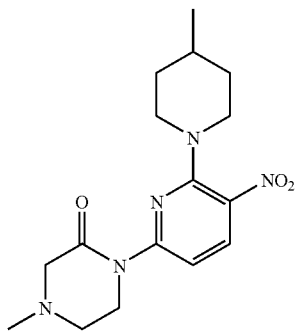

To a solution of 6'-bromo-4-methyl-3'-nitro-3,4,5,6-tetrahydro-2H-[1,2']bipyridinyl (as prepared in the previous step) (300 mg, 1.00 mmol) in toluene (5 mL) was added 3-oxo-piprazine-1-carboxylic acid benzyl ester (351 mg, 1.50 mmol), $K_3PO_4$ (424 mg, 2.00 mmol) and CuI (38 mg, 0.20 mmol) followed by N,N'-dimethylethylenediamine (20 µL, 0.18 mmol) under Ar. The resulting mixture was heated at reflux overnight. The reaction mixture was allowed to cool to room temperature and filtered through a thin pad of Celite. The filtrate was concentrated in vacuo and the residue obtained was purified by chromatography on silica (20% EtOAc:hexane) to obtain 4-(4-methyl-3'-nitro-3,4,5,6-tetrahydro-2H-[1,2']bipyridinyl-6'-yl)-3-oxo-piperazine-1-carboxylic acid benzyl ester (258 mg, 57%). This compound (453 mg, 1.00 mmol) was dissolved in 30% HBr/HOAc (1 mL). The resulting mixture was stirred at room temperature overnight and $Et_2O$ (20 mL) was added dropwise. The resulting mixture was stirred for another hour, the precipitated hydrobromide was collected by suction filtration, washed with $Et_2O$ (3×20 mL), dried in vacuo for 1 h and used directly in next step.

The above hydrobromide (48 mg, 0.10 mmol) was added to 37% aq HCHO (ca. 0.05 mL, 0.05 mmol) followed by NaBH(OAc)$_3$ (106 mg, 0.050 mmol). The resulting mixture was stirred at room temperature for 30 min and the product was extracted with $CH_2Cl_2$ (3×10 mL). The $CH_2Cl_2$ layers were combined, dried (Na$_2$SO$_4$) and concentrated in vacuo. The residue obtained was purified on silica (10-50% EtOAc:hexane) to obtain the title compound (27 mg, 81%). $^1$H-NMR (CDCl$_3$; 400 MHz): δ 8.21 (d, 1H, J=8.9 Hz), 7.58 (d, 1H, J=8.9 Hz), 3.98 (m, 2H), 3.75 (m, 2H), 3.31 (s, 2H), 2.96 (m, 2H), 2.72 (m, 2H), 2.39 (s, 3H), 1.9-1.65 (m, 3H), 1.25 (m, 2H), 0.99 (d, 3H, J=6.42 Hz).

c) 5-Cyano-furan-2-carboxylic acid[4-methyl-6'-(4-methyl-2-oxo-piperazin-1-yl)-3,4,5,6-tetrahydro-2H-[1,2']bipyridinyl-3'-yl]-amide

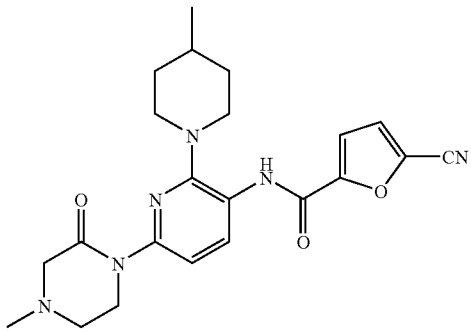

4-Methyl-1-(4-methyl-3'-nitro-3,4,5,6-tetrahydro-2H-[1,2']bipyridinyl-6'-yl)-piperazin-2-one (as prepared in the previous step) (99 mg, 0.29 mmol) was converted to corresponding amine according to the procedure in Example 55, step (c) and coupled with 5-cyano-furan-2-carbonyl chloride as prepared in Example 4, step (c) (obtained from 68.5 mg, 0.500 mmol of 5-cyano-furan-2-carboxylic acid as prepared in Example 1) in $CH_2Cl_2$ (2 mL) at 0° C. The product was isolated flash chromatography on silica (20% EtOAc/hexane-10% MeOH/EtOAc) to give the title compound (53 mg, 43%). $^1$H-NMR (CDCl$_3$; 400 MHz): δ 8.98 (br s, 1H), 8.61 (d, 1H, J=8.7 Hz), 7.71 (d, 1H, J=8.7 Hz), 7.28 (d, 1H, J=3.7 Hz), 7.22 (d, 1H, J=3.7 Hz), 3.99 (m, 2H), 3.28 (s, 2H), 3.16 (m, 2H), 2.87-2.77 (m, 4H), 2.38 (s, 3H), 1.83 (m, 2H), 1.62 (m, 1H), 1.44 (m, 2H), 1.04 (d, 3H, J=6.3 Hz). LC-MS (ESI, m/z): Calcd. for $C_{22}H_{26}N_6O_3$, 423.2 (M+H), found 423.1

Example 62

5-Cyano-furan-2-carboxylic acid[4-methyl-6'-(4-methyl-3-oxo-piperazin-1-yl)-3,4,5,6-tetrahydro-2H-[1,2']bipyridinyl-3'-yl]-amide

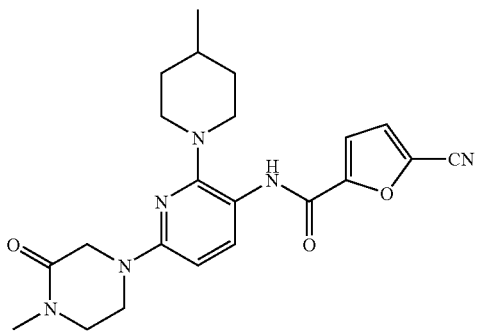

a) 4-Methyl-3-oxo-piperazine-1-carboxylic acid benzyl ester

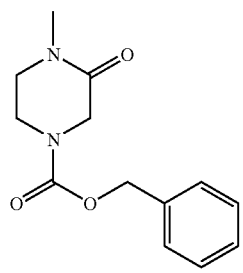

To a solution of 3-oxo-piperazine-1-carboxylic acid benzyl ester (2.00 g, 8.54 mmol) in DMF (30 mL) was added KOtBu (1.54 g, 13.7 mmol) under Ar. The resulting solution was stirred at room temperature for 15 min and cooled to 0° C. MeI (0.85 mL, 14 mmol) was then added dropwise. The reaction mixture was allowed to warm to room temperature and stirred for 3 h. DMF was removed in vacuo and the residue was chromatographed on silica (5-50% EtOAc:hexane) to obtain the title compound (1.40 g, 66%). $^1$H-NMR (CDCl$_3$; 400 MHz): δ 7.32 (m, 5H), 5.13 (s, 2H), 4.13 (s, 2H), 3.70 (m, 2H), 3.34 (m, 2H), 2.97 (s, 3H)

b) 1-Methyl-4-(4-methyl-3'-nitro-3,4,5,6-tetrahydro-2H-[1,2']bipyridinyl-6'-yl)-piperazin-2-one

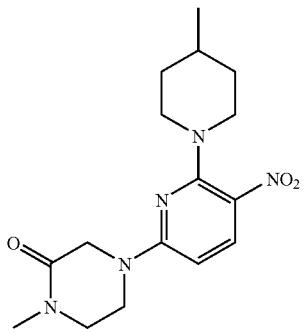

4-Methyl-3-oxo-piperazine-1-carboxylic acid benzyl ester (as prepared in the previous step) (124 mg, 0.50 mmol) was dissolved in 30% HBr/HOAc (0.5 mL). The resulting mixture was stirred at room temperature overnight and Et$_2$O (20 mL) was added drop wise. The resulting mixture was stirred for another hour and the precipitate formed was collected by suction filtration, washed with Et$_2$O (3×20 mL), dried in vacuo for 1 h and directly used in next step.

To a solution of 6'-chloro-4-methyl-3'-nitro-3,4,5,6-tetrahydro-2H-[1,2']bipyridinyl (as prepared in Example 55, step (a)) (510 mg, 2.00 mmol) in DMF (10 mL) was added 1-methyl piperazinone hydrobromide (390 mg, 2.00 mmol) and K$_2$CO$_3$ (691 mg, 5.00 mmol). The resulting mixture was heated at 100° C. overnight. DMF was removed in vacuo and the residue obtained was purified on silica (20-100% EtOAc: hexane) to obtain the title compound (540 mg, 81%). $^1$H-NMR (CDCl$_3$; 400 MHz): δ 8.15 (d, 1H, J=9.1 Hz), 5.94 (d, 1H, J=9.1 Hz), 4.22 (s, 2H), 3.88 (m, 2H), 3.76 (m, 2H), 3.46 (m, 2H), 3.01-2.92 (m, 5H), 1.68 (m, 3H), 1.25 (m, 2H), 0.93 (d, 3H, J=6.3 Hz).

c) 5-Cyano-furan-2-carboxylic acid[4-methyl-6'-(4-methyl-3-oxo-piperazin-1-yl)-3,4,5,6-tetrahydro-2H-[1,2']bipyridinyl-3'-yl]-amide 1-Methyl-4-(4-methyl-3'-nitro-3,4,5,6-tetrahydro-2H-[1,2']bipyridinyl-6'-yl)-piperazin-2-one (as prepared in previous step) (166 mg, 0.50 mmol) was converted to the corresponding amine according to the procedure in Example 55, step (c) and coupled with 5-cyano-furan-2-carbonyl chloride as prepared in Example 4, step (c) (obtained from 137 mg, 1.00 mmol of 5-cyano-furan-2-carboxylic acid as prepared in Example 1) in CH$_2$Cl$_2$ (2 mL) at 0° C. The product was isolated by flash chromatography on silica (20% EtOAc/hexane-10% MeOH/EtOAc) to obtain the title compound (108 mg, 51%). $^1$H-NMR (CDCl$_3$; 400 MHz): δ 8.73 (br s, 1H), 8.44 (d, 1H, J=8.7 Hz), 7.24 (d, 1H, J=3.7 Hz), 7.22 (d, 1H, J=3.7 Hz), 6.32 (d, 1H, J=8.7 Hz), 4.16 (m, 2H), 3.84 (m, 2H), 3.46 (m, 2H), 3.20 (m, 2H), 3.04 (s, 3H), 2.84 (m, 2H), 1.8 (m, 2H), 1.4 (m, 1H), 1.32 (m, 2H), 1.04 (d, 3H, J=6.3 Hz). LC-MS (ESI, m/z): Calcd. for C$_{22}$H$_{26}$N$_6$O$_3$, 423.2 (M+H), found 423.1

Example 63

5-Cyano-furan-2-carboxylic acid[4,1''-dimethy-3,4,5,6,1'',2'', 3'',4'',5'',6''-decahydro-2H-{1,2',6',4''] terpyridin-3'-yl)-amide

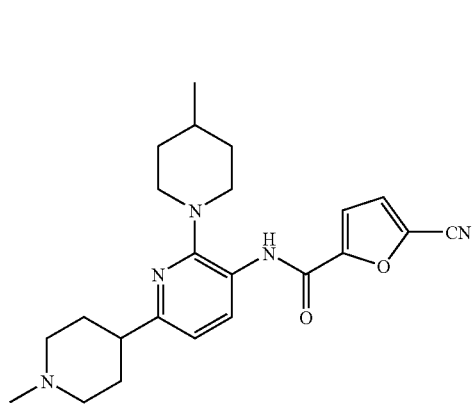

a) 4,1''-Dimethyl-3'-nitro-3,4,5,6,1'',2'',3'',6''-octahydro-2H-[1,2',6',4'']terpyridine

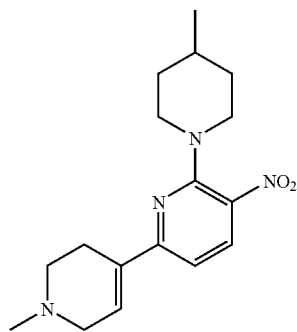

5'-Chloro-4-methyl-2'-nitro-3,4,5,6-tetrahydro-2H-[1,3'] bipyridinyl (as described in Example 55, step (a)) (159 mg, 0.790 mmol), $K_2CO_3$ (310 mg, 2.25 mmol) and 4-(4,4,5,5-tetramethyl-[1,3,2]dioxaborolan-2-yl)-3,6-dihydro-2H-pyridine-1-carboxylic acid tert-butyl ester (Eastwood, P. R., Tetrahedron Letters, 41, (19), (2000)) (231 mg, 0.750 mmol) in dioxane (5 mL) were heated at 80° C. overnight under Ar. The reaction mixture was allowed to cool to RT, concentrated and the resulting residue was chromatographed on silica (10% EtOAc/hexane) to obtain the coupled compound (139 mg, 44%). This compound (139 mg, 0.340 mmol) was dissolved in 1:1 mixture of TFA/$CH_2Cl_2$ (5 mL) and the resulting mixture was stirred at RT for 1 hr. The reaction mixture was concentrated and the resulting residue was dried in vacuo for 2 h and dissolved in 37% aq. HCHO (1 mL). $Na(OAc)_3BH$ (464 mg, 2.10 mmol) was then added and the resulting mixture was stirred for 1 h. The reaction mixture was diluted with std aq $NaHCO_3$ and the product was extracted with $CH_2Cl_2$ (3×10 mL). The organic layers were combined, dried ($Na_2SO_4$) and concentrated. The product was isolated by flash chromatography on silica (20% EtOAc/hexane) to obtain the title compound (66 mg, 60%). LC-MS (ESI, m/z): Calcd. for $C_{17}H_{24}N_4O_2$, 317.2 (M+H), found 317.0 b) 4,1''-Dimethyl-3,4,5,6,1'',2'',3'',4'',5'',6''-decahydro-2H-[1,2',6',4'']terpyridine-3'-ylamine

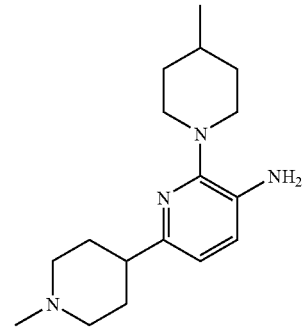

4,1''-Dimethyl-3'-nitro-3,4,5,6,1'',2'',3'',6''-octahydro-2H-[1,2',6',4'']terpyridine (as prepared in the previous step) (60 mg, 0.20 mmol) was dissolved in MeOH (10 mL) and hydrogenated over 10% Pd/C (30 mg) under $H_2$ balloon pressure for 2 h. The reaction mixture was filtered through a thin pad of Celite. The filtrate was concentrated and the residue obtained was purified on silica with 5% $NH_3$/MeOH to obtain the title compound (41 mg, 75%). LC-MS (ESI, m/z): Calcd. for $C_{17}H_{28}N_4$, 289.23 (M+H), found 289.3.

c) 5-Cyano-furan-2-carboxylic acid[4,1''-dimethy-3,4,5,6,1'',2'',3'',4'',5'',6''decahydro2H-{1,2',6',4''] terpyridin-3'-yl)-amide

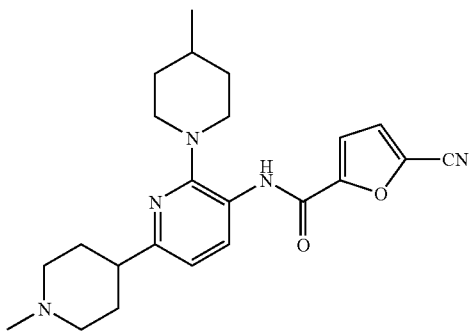

4,1''-Dimethyl-3,4,5,6,1'',2'',3'',4'',5'',6''-decahydro-2H-[1,2',6',4'']terpyridine-3'-ylamine as prepared in the previous step (41 mg, 0.12 mmol) was coupled with 5-cyano-furan-2-carbonyl chloride as prepared in Example 4, step (c) (obtained from 69 mg, 0.50 mmol of 5-cyano-furan-2-carboxylic acid as prepared in Example 1) in $CH_2Cl_2$ (2 mL) at 0° C. The product was isolated by flash chromatography on silica (20% EtOAc/hexane-10% MeOH/EtOAc) to obtain the title compound (20 mg, 35%). $^1$H-NMR (CDCl$_3$; 400 MHz): δ 9.12 (br s, 1H), 8.52 (d, 1H, J=8.7 Hz), 7.29 (d, 1H, J=3.7 Hz), 7.24 (d, 1H, J=3.7 Hz), 6.92 (d, 1H, J=8.7 Hz), 3.20 (m, 2H), 2.9 (m, 4H), 2.6 (m, 1H), 2.34 (s, 3H), 2.05 (m, 2H), 1.86 (m, 6H), 1.7 (m, 1H), 1.5 (m, 2H), 1.04 (d, 3H, J=6.3 Hz). LC-MS (ESI, m/z): Calcd. for $C_{23}H_{29}N_5O_2$, 408.2 (M+H), found 408.2.

Example 64

5-Cyano-furan-2-carboxylic acid[4-[4-methyl-pierazin-1-yl)-2-morpholin-4-yl-phenyl]-amide

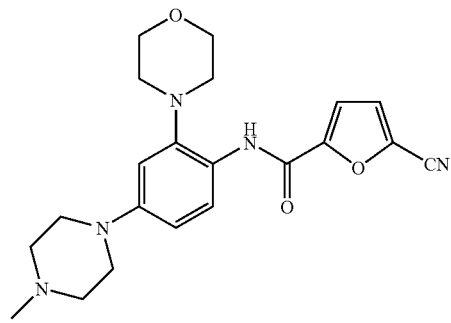

a) 4-[5-(4-methyl-piperazin-1 yl)-2-nitro-phenyl)-morpholine

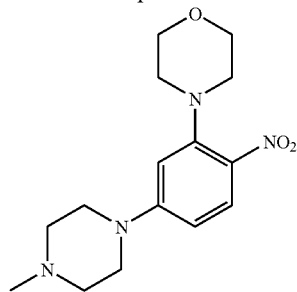

To a mixture of 4-chloro-2-fluoronitrobenzene (175 mg, 1.00 mmol) and K$_2$CO$_3$ (139 mg, 1.00 mmol) in toluene (2 mL), morpholine (87 μL, 1.0 mmol) was added at 0° C. The resulting mixture was allowed to warm to RT and stirred overnight. The reaction mixture was concentrated and the product was isolated by flash chromatography on silica (20% EtOAc/hexane) to obtain 4-(5-Chloro-2-nitro-phenyl)-morpholine (205 mg, 67%). This compound (243 mg, 1.00 mmol) was dissolved in 1-methylpiperazine (1 mL) and the resulting mixture was heated at 130° C. overnight. The reaction mixture was diluted with water and the product was extracted with DCM (3×10 mL). The DCM layers were combined, dried (Na$_2$SO$_4$) and concentrated to obtain the title compound (177 mg, 58%). $^1$H-NMR (CDCl$_3$; 400 MHz): δ 8.04 (d, 1H, J=9.4 Hz), 6.46 (dd, 1H, J=9.4, 2.6 Hz), 6.31 (d, 1H, =2.6 Hz), 3.89 (m, 4H), 3.40 (m, 4H), 3.07 (m, 4H), 2.50 (m, 4H), 2.36 (s, 3H).

b) 5-Cyano-furan-2-carboxylic acid[4-[4-methyl-pierazin-1-yl)-2-morpholin-4-yl-phenyl]-amide

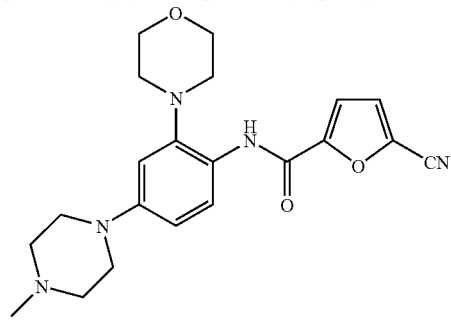

4-[5-(4-Methyl-piperazin-1-yl)-2-nitro-phenyl)-morpholine (as prepared in the previous step) (138 mg, 0.480 mmol) was converted to corresponding amine according to the procedure in Example 55, step (c) and coupled with 5-cyano-furan-2-carbonyl chloride as prepared in Example 4, step (c) (obtained from 137 mg, 1.00 mmol of 5-cyano-furan-2-carboxylic acid as prepared in Example 1) in CH$_2$Cl$_2$ (2 mL) at 0° C. The product was isolated by flash chromatography on silica (25% EtOAc/hexane-10% MeOH/EtOAc) to obtain the title compound (87 mg, 49%). $^1$H-NMR (CDCl$_3$; 400 MHz): δ 9.40 (br s, 1H), 8.32 (d, 1H, J=8.7 Hz), 7.26 (d, 1H, J=3.7 Hz), 7.22 (d, 1H, J=3.7 Hz), 6.80 (d, 1H, =2.6 Hz), 6.78 (d, 1H, J=8.7 Hz), 3.93 (m, 4H), 3.20 (m, 4H), 2.92 (m, 4H), 2.60 (m, 4H), 2.36 (s, 3H). LC-MS (ESI, m/z): Calcd. for C$_{21}$H$_{25}$N$_5$O$_3$, 396.2 (M+H), found 396.2.

Example 65

5-Cyano-furan-2-carboxylic acid [4-methyl-6'-(tetrahydro-pyran-4-yl)-3,4,5,6-tetrahydro-2H-[1,2']bipyridinyl-3'-yl]-amide

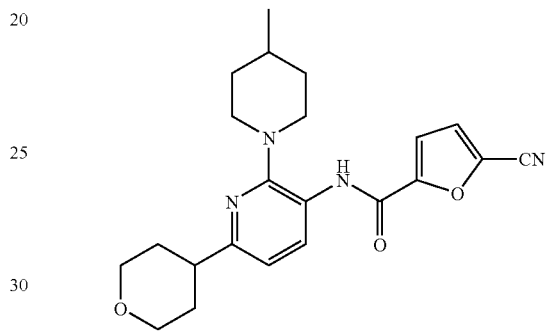

a) 6'-(3,6-Dihydro-2H-pyran-4-yl)-4-methyl-3'-nitro-3,4,5,6-tetrahydro-2H-[1,2']bipyridinyl

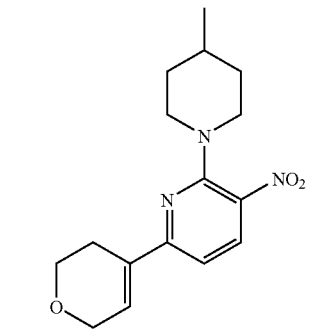

A mixture of 6'-bromo-4-methyl-3'-nitro-3,4,5,6-tetrahydro-2H-[1,2']bipyridinyl (as prepared in Example 61, step (a)) (237 mg, 0.79 mmol), anhydrous K$_2$CO$_3$ (311 mg, 2.25 mmol) and 4-(4,4,5,5-tetramethyl-[1,3,2]dioxaborolan-2-yl)-3,6-dihydro-2H-pyran (Murata, M., Synthesis, 778, (2000)) (157 mg, 0.750 mmol) in dioxane (5 mL) was heated at 80° C. overnight under Ar. The reaction mixture was allowed to cool to RT, concentrated and the resulting residue was purified on silica (10% EtOAc/hexane) to obtain the expected coupled compound (71 mg, 30%). $^1$H-NMR (CDCl$_3$; 400 MHz): δ 8.15 (d, 1H, J=8.4 Hz), 6.80 (m, 2H), 4.39 (m, 2H), 3.92 (t, 2H, J=5.4 Hz), 3.76 (m, 2H), 3.04 (m, 2H), 2.62 (m, 2H), 1.67 (m, 3H), 1.33 (m, 2H), 0.99 (d, 3H, J=6.3 Hz).

b) 5-Cyano-furan-2-carboxylic acid [4-methyl-6'-(tetrahydro-pyran-4-yl)-3,4,5,6-tetrahydro-2H-[1,2']bipyridinyl-3'-yl]-amide

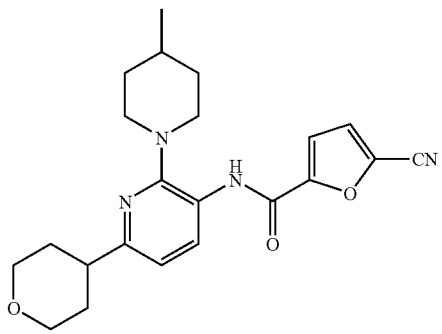

6'-(3,6-Dihydro-2H-pyran-4-yl)-4-methyl-3'-nitro-3,4,5,6-tetrahydro-2H [1,2']bipyridinyl (as prepared in the previous step) (70 mg, 0.23 mmol) was dissolved in MeOH (10 mL) and hydrogenated over 10% Pd/C (30 mg) under H$_2$ balloon pressure for 2 h. The reaction mixture was filtered through a thin pad of Celite. The filtrate was concentrated and the residue obtained was purified on silica 5% NH$_3$/MeOH to obtain the corresponding aniline compound (46 mg, 72%).

The above aniline (138 mg, 0.500 mmol) was coupled with 5-cyano-furan-2-carbonyl chloride as prepared in Example 4, step (c) (obtained from 137 mg, 1.00 mmol of 5-cyano-furan-2-carboxylic acid as prepared in the Example 1) in CH$_2$Cl$_2$ (2 mL) at 0° C. The product was isolated by flash chromatography on silica (20% EtOAc/hexane-10% MeOH/EtOAc) to obtain the title compound (69 mg, 35%). $^1$H-NMR (CDCl$_3$; 400 MHz): δ 9.10 (br s, 1H), 8.52 (d, 1H, J=8.2 Hz), 7.28 (d, 1H, J=4.4 Hz), 7.24 (d, 1H, J=4.4 Hz), 6.91 (d, 1H, J=8.2 Hz), 4.07 (m, 2H), 3.53 (m, 2H), 3.15 (m, 2H), 2.80 (m, 3H), 1.85 (m, 6H), 1.65 (m, 1H), 1.45 (m, 2H), 1.04 (d, 3H, J=6.3 Hz). LC-MS (ESI, m/z): Calcd. for C$_{22}$H$_{26}$N$_4$O$_3$, 395.2 (M+H), found 395.2.

Example 66

5-Cyano-1H-imidazole-2-carboxylic acid [4-methyl-6'-(tetrahydro-pyran-4-yl)-3,4,5,6-tetrahydro-2H-[1,2']bipyridinyl-3'-yl]-amide

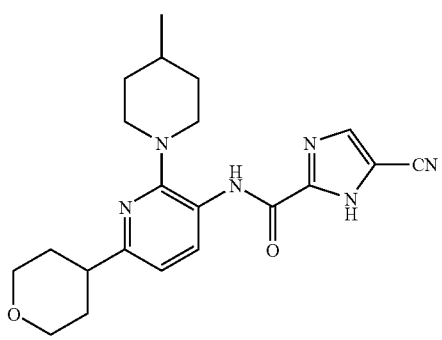

6'-(3,6-Dihydro-2H-pyran-4-yl)-4-methyl-3'-nitro-3,4,5,6-tetrahydro-2H [1,2']bipyridinyl (as prepared in Example 65, step (a)) (70 mg, 0.23 mmol) was dissolved in MeOH (10 mL) and hydrogenated over 10% Pd/C (30 mg) under H$_2$ balloon pressure for 2 hr. The reaction mixture was filtered through a thin pad of Celite. The filtrate was concentrated and the residue obtained was purified on silica 5% NH$_3$/MeOH to obtain the corresponding aniline compound (46 mg, 72%).

The above aniline (112 mg, 0.400 mmol) was coupled with 5-cyano-1-(2-trimethylsilanyl-ethoxymethyl)-1H-imidazole-2-carboxylic acid potassium salt (as prepared in Example 3) as described in Example 47, step (e). The product was isolated by flash chromatography on silica (20% EtOAc/hexane-10% MeOH/EtOAc) (97 mg, 45%). This compound (84 mg, 0.15 mmol) was dissolved in 2:1 TFA/DCM (5 mL) and allowed to stir at RT for 4 h. The reaction mixture was concentrated and the product was partitioned between DCM and satd aq NaHCO$_3$. The DCM layer was separated, dried (Na$_2$SO$_4$) and concentrated to obtain the titled compound (55 mg, 88%). $^1$H-NMR (CDCl$_3$; 400 MHz): δ 12.63 (br s, 1H), 9.84 (br s, 1H), 8.46 (d, 1H, J=8.2 Hz), 7.82 (s, 1H), 6.91 (d, 1H, J=8.2 Hz), 4.10 (m, 2H), 3.61 (m, 2H), 3.23 (m, 2H), 2.92 (m, 3H), 1.98 (m, 7H), 1.35 (m, 2H), 0.98 (d, 3H, J=6.3 Hz). LC-MS (ESI, m/z): Calcd. for C$_{21}$H$_{26}$N$_6$O$_2$, 395.2 (M+H), found 395.4.

Example 67

5-Cyano-furan-2-carboxylic acid {4-methyl-6'-[4-(2-morpholin-4-yl-2-oxo-ethyl)-piperazin-1-yl]-3,4,5,6-tetrahydro-2H-[1,2']bipyridinyl-3'-yl}-amide

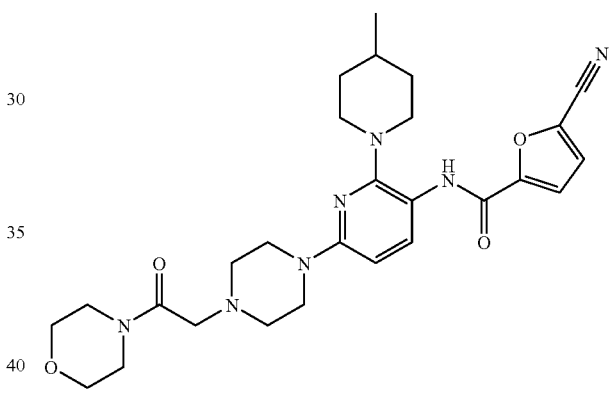

a) 6'-Chloro-4-methyl-3'-nitro-3,4,5,6-tetrahydro-2H-[1,2']bipyridinyl

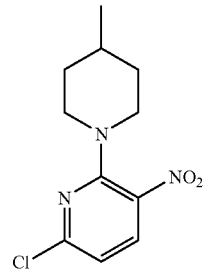

A solution of 2,6-dichloro-3-nitro-pyridine (1.47 g, 7.61 mmol) in toluene (40 mL) was treated with, solid K$_2$CO$_3$ (1.26 g, 9.13 mmol) and 4-methyl-piperidine (0.90 mL, 7.6 mmol). The reaction was stirred at room temperature for 1.5 h, additional toluene (10 mL) was added, and the reaction was stirred an additional 5 h. The reaction was diluted with EtOAc and washed with water. The aqueous layer was further extracted with EtOAc. The combined organic layers were dried over MgSO$_4$ and concentrated in vacuo to afford the title compound (2.00 g, 100%) as a waxy, bright yellow solid. $^1$H-NMR (CDCl$_3$; 400 MHz): δ 8.06 (d, 1H, J=4.0 Hz), 7.61 (d, 1H, J=4.0 Hz), 3.83-3.75 (m, 2H), 3.08-2.97 (m, 2H), 1.77-1.68 (m, 2H), 1.57 (br s, 1H), 1.37-1.23 (m, 2H), 0.98 (d, 3H, J=6.4 Hz). LC-MS (ESI, m/z): Calcd. for C$_{11}$H$_{14}$ClN$_3$O$_2$, 256.1 (M+H), found 256.1.

b) 4-(4-Methyl-3'-nitro-3,4,5,6-tetrahydro-2H-[1,2']bipyridinyl-6'-yl)-piperazine-1-carboxylic acid benzyl ester

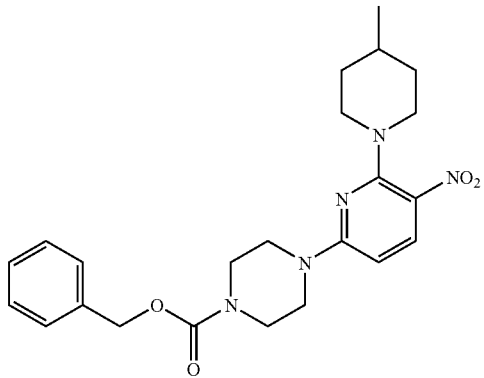

A solution of 6'-chloro-4-methyl-3'-nitro-3,4,5,6-tetrahydro-2H-[1,2']bipyridinyl (as prepared in the previous step, 2.0 g, 7.8 mmol) in DMF (40 mL) was treated with solid Na$_2$CO$_3$ (0.99 g, 9.4 mmol) and piperazine-1-carboxylic acid benzyl ester (1.5 mL, 7.8 mmol), then heated to 90° C. for 1 h and to 40° C. for 15 h. The reaction was concentrated to 20 mL volume, diluted with EtOAc, and washed well with water. The combined aqueous layers were further extracted with EtOAc. The combined organic layers were dried over MgSO$_4$ and concentrated in vacuo. Silica gel chromatography (25% EtOAc in hexane) afforded the title compound (3.2 g, 94%) as a yellow solid. $^1$H-NMR (CDCl$_3$; 400 MHz): δ 8.19 (d, 1H, J=9.2 Hz), 7.39-7.31 (m, 5H), 6.01 (d, 1H, J=9.2 Hz), 5.16 (s, 2H), 3.84-3.76 (m, 2H), 3.71-3.65 (m, 4H), 3.64-3.58 (m, 4H), 3.02-2.93 (m, 2H), 1.74-1.65 (m, 2H), 1.66-1.60 (m, 1H), 1.38-1.26 (m, 2H), 0.97 (d, 3H, J=6.4 Hz). LC-MS (ESI, m/z): Calcd. for C$_{23}$H$_{29}$N$_5$O$_4$, 440.2 (M+H), found 439.9.

c) 4-Methyl-3'-nitro-6'-piperazin-1-yl-3,4,5,6-tetrahydro-2H-[1,2']bipyridinyl dihydrobromide

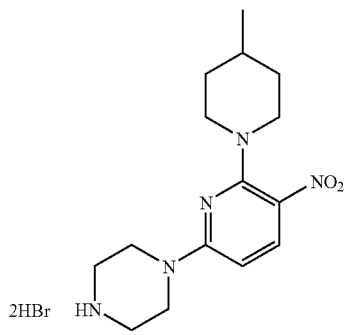

A solution of 4-(4-methyl-3'-nitro-3,4,5,6-tetrahydro-2H-[1,2']bipyridinyl-6'-yl)-piperazine-1-carboxylic acid benzyl ester (as prepared in the previous step, 3.2 g, 7.3 mmol) in HOAc (50 mL) was treated with 30% HBr in HOAc (7.3 mL, 1 mL/mmol benzyl ester) and heated to 60° C. for 1 h. The reaction was cooled to room temperature and allowed to stir for 5 h, after which time Et$_2$O was added to the reaction while stirring. The bright yellow precipitate was filtered and washed with Et$_2$O to afford the title compound (2.6 g, 77%). $^1$H-NMR (CD$_3$OD; 400 MHz): δ 8.44 (d, 1H, J=9.6 Hz), 6.95 (d, 1H, J=9.6 Hz), 4.13 (app t, 4H, J=5.2 Hz), 3.87-3.79 (m, 2H), 3.71-3.60 (m, 2H), 3.42 (app t, 4H, J=5.2 Hz), 2.09-2.00 (m, 2H), 1.99-1.88 (m, 1H), 1.69-1.55 (m, 2H), 1.09 (d, 3H, J=6.8 Hz). LC-MS (ESI, m/z): Calcd. for C$_{15}$H$_{23}$N$_5$O$_2$, 306.2 (M+H), found 306.1.

d) 2-Chloro-1-morpholin-4-yl-ethanone

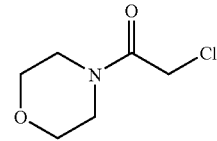

A solution of morpholine (0.50 g, 5.7 mmol) in CH$_2$Cl$_2$ (10 mL) was treated with Et$_3$N and cooled to 0° C. The mixture was treated with chloroacetyl chloride (0.50 mL, 6.3 mmol) as a solution in CH$_2$Cl$_2$ (2 mL). The reaction was stirred at 0° C. for 15 min and then at room temperature for 30 min. The reaction was diluted with CH$_2$Cl$_2$ and washed with water. The organic layer was dried over MgSO$_4$ and concentrated in vacuo to afford the title compound (0.72 g, 76%) as a colorless oil. $^1$H-NMR (CDCl$_3$; 400 MHz): δ 4.06 (s, 2H), 3.73-7.67 (m, 4H), 3.62 (app t, 2H, J=4.0 Hz), 3.52 (app t, 2H, J=4.0 Hz).

e) 2-[4-(4-Methyl-3'-nitro-3,4,5,6-tetrahydro-2H-[1,2']bipyridinyl-6'-yl)-piperazin-1-yl]-1-morpholin-4-yl-ethanone

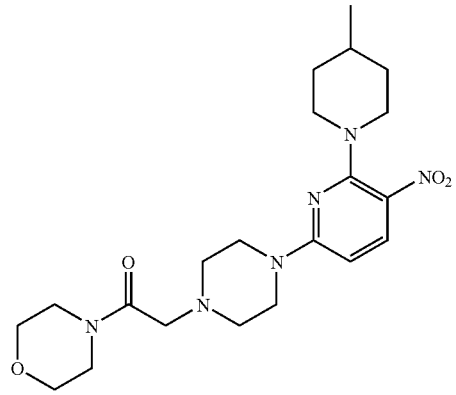

A solution of 4-methyl-3'-nitro-6'-piperazin-1-yl-3,4,5,6-tetrahydro-2H-[1,2']bipyridinyl dihydrobromide (as prepared in Example 67, step (c), 0.10 g, 0.21 mmol) in CH$_2$Cl$_2$ (5 mL) was treated with Et$_3$N (0.10 mL, 0.75 mmol) and 2-chloro-1-morpholin-4-yl-ethanone (as prepared in the previous step, 39 mg, 0.24 mmol). The reaction stirred at room temperature for 18.5 h. The reaction was diluted with CH$_2$Cl$_2$ and washed with water. The aqueous layer was further extracted with CH$_2$Cl$_2$. The combined organic layers were dried over MgSO$_4$ and concentrated in vacuo to afford the title compound (0.11 g, 117%, some salt remains) as a yellow solid, which was used directly in the next step without further purification. $^1$H-NMR (CDCl$_3$; 400 MHz): δ 8.19 (d, 1H, J=9.2 Hz), 6.02 (d, 1H, J=9.2 Hz), 3.76-3.67 (m, 8H), 3.26 (br s, 2H), 3.14-3.07 (m, 2H), 3.03-2.93 (m, 2H), 2.63 (br s, 4H), 1.74-1.65 (m, 2H), 1.65-1.58 (m, 1H), 1.45-1.39 (m, 3H), 1.37-1.24 (m, 3H), 0.97 (d, 3H, J=6.4 Hz). LC-MS (ESI, m/z): Calcd. for $C_{21}H_{32}N_6O_4$, 433.2 (M+H), found 433.1.

f) 2-[4-(3'Amino-4-methyl-3,4,5,6-tetrahydro-2H-[1, 2']bipyridinyl-6'-yl)-piperazin-1-morpholin-4-yl-ethanone

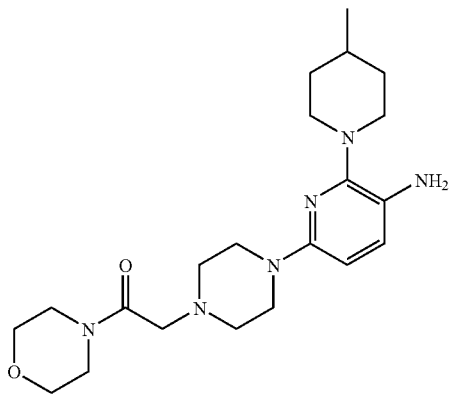

A solution of 2-[4-(4-2-ethyl-3'-nitro-3,4,5,6-tetrahydro-2H-[1,2']bipyridinyl-6'-yl)-piperazin-1-yl]-1-morpholin-4-yl-ethanone (as prepared in the previous step, 0.11 g, 0.25 mmol) in 2:1 EtOH:water (15 mL) was treated with $NH_4Cl$ (0.14 g, 2.5 mmol) and was heated to 100° C. Iron powder (70.4 mg, 1.26 mmol) was added and the reaction stirred at 100° C. for 2 h. The reaction was neutralized with saturated aqueous $NaHCO_3$ and extracted with $CH_2Cl_2$. The combined organic layers were dried over $MgSO_4$ and concentrated in vacuo to afford the title compound (0.10 g, 98%), which was used immediately in the next reaction.

g) 5-Cyano-furan-2-carboxylic acid {4-methyl-6'-[4-(2-morpholin-4-yl-2-oxo-ethyl)-piperazin-1-yl]-3,4, 5,6-tetrahydro-2H-[1,2']bipyridinyl-3'-yl}-amide

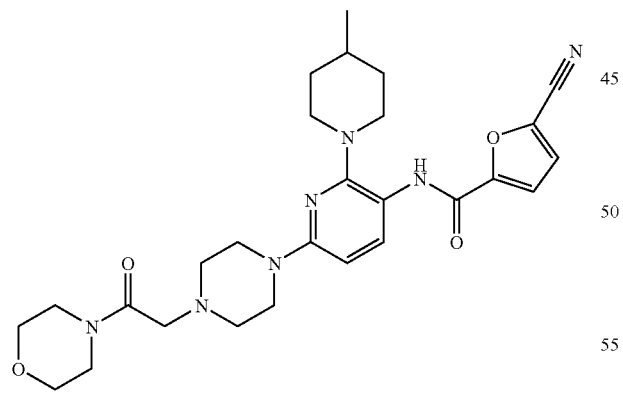

A solution of 5-cyano-furan-2-carboxylic acid (as prepared in Example 1, 70 mg, 0.51 mmol) in $CH_2Cl_2$ (5 mL) and DMF (30 µL) was treated with oxalyl chloride (49 µL, 0.56 mmol) and stirred at room temperature for 1 h; The solvents were evaporated in vacuo. The residue was taken up in $CH_2Cl_2$ (5 mL). A solution of 2-[4-(3'amino-4-methyl-3,4,5, 6-tetrahydro-2H-[1,2']bipyridinyl-6'-yl)-piperazin-1-morpholin-4-yl-ethanone (as prepared in the previous step, 0.10 g, 0.25 mmol) was treated with DIEA (66 µL, 0.38 mmol) and cooled to 0° C. The solution of acid chloride generated above was added dropwise, and the reaction was stirred at room temperature for 19 h. The reaction was diluted with $CH_2Cl_2$ and washed with water. The combined aqueous layers were extracted with $CH_2Cl_2$. The combined organic layers were dried over $MgSO_4$ and concentrated in vacuo. Silica gel chromatography (25-100% EtOAc in hexane, then 1-10% MeOH in $CH_2Cl_2$) afforded the title compound (14 mg, 11%) as a white solid. $^1$H-NMR ($CDCl_3$; 400 MHz): δ 8.76 (br s, 1H), 8.43-8.39 (m, 1H), 7.24 (d, 1H, J=3.6 Hz), 7.21 (d, 1H, J=3.6 Hz), 6.36 (d, 1H, J=8.8 Hz), 3.71-3.61 (m, 8H), 3.55-3.48 (m, 4H), 3.24 (s, 2H), 3.22-3.15 (m, 2H), 2.88-2.79 (m, 2H), 2.66-2.60 (m, 4H), 1.84-1.76 (m, 2H), 1.64-1.52 (m, 1H), 1.4-1.36 (m, 2H), 1.04 (d, 3H, J=6.4 Hz). LC-MS (ESI, m/z): Calcd. for $C_{27}H_{35}N_7O_4$, 522.3 (M+H), found 522.2.

Example 68

5-Cyano-furan-2-carboxylic acid{4-methyl-6'-[4-(2-morpholin-4-yl-acetyl)-piperazin-1-yl]-3,4,5,6-tetrahydro-2H-[1,2']bipyridinyl-3'-yl}-amide trifluoroacetic acid salt

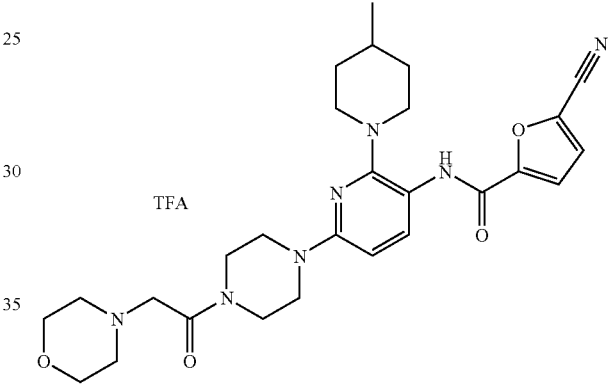

a) 2-Chloro-1-[4-(4-methyl-3'-nitro-3,4,5,6-tetrahydro-2H-[1,2']bipyridinyl-6'-yl)-piperazin-1-yl]-ethanone

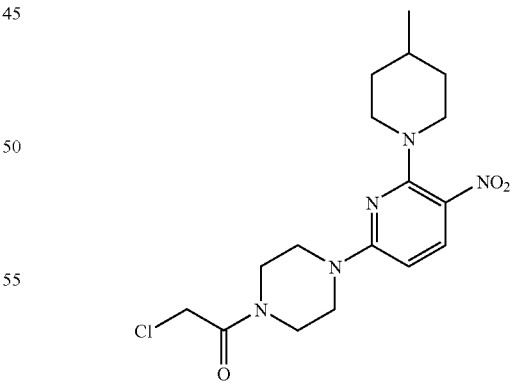

A solution of 4-methyl-3'-nitro-6'-piperazin-1-yl-3,4,5,6-tetrahydro-2H-[1,2']bipyridinyl dihydrobromide (as prepared in Example 67, step (c), 0.28 g, 0.60 mmol) in $CH_2Cl_2$ (6 mL) was treated with $Et_3N$ (0.27 mL, 1.9 mmol) and cooled to 0° C. The mixture was treated with chloroacetyl chloride (53 µL, 0.66 mmol) as a solution in $CH_2Cl_2$ (2 mL) and stirred at 0° C. for 15 min then at room temperature for 30 min. The reaction was diluted with CH₂Cl₂ and washed with water. The organic layer was dried over MgSO₄ and concentrated in vacuo to afford the title compound (0.18 g, 80%) as a yellow solid. $^1$H-NMR (CDCl₃; 400 MHz): δ 8.21 (d, 1H, J=9.2 Hz), 6.03 (d, 1H, J=9.2 Hz), 4.11 (s, 2H), 3.84-3.76 (m, 4H), 3.76-3.61 (m, 4H), 3.13-3.05 (m, 1H), 3.04-2.92 (m, 2H), 1.7-1.66 (m, 2H), 1.45-1.38 (m, 2H), 1.38-1.25 (m, 2H), 0.98 (d, 3H, J=6.4 Hz). LC-MS (ESI, m/z): Calcd. for C₁₇H₂₄ClN₅O₃, 382.1 (M+H), found 382.1.

b) 1-[4-(4-Methyl-3'-nitro-3,4,5,6-tetrahydro-2H-[1,2']bipyridinyl-6'-yl)-piperazin-1-yl]-2-morpholin-4-yl-ethanone

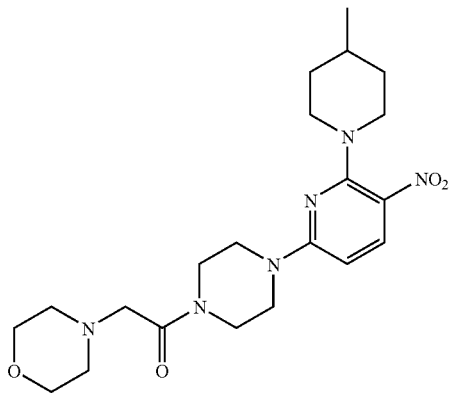

A solution of 2-chloro-1-[4-(4-methyl-3'-nitro-3,4,5,6-tetrahydro-2H-[1,2']bipyridinyl-6'-yl)-piperazin-1-yl]-ethanone (as prepared in the previous step, 0.18 g, 0.48 mmol) in CH₂Cl₂ (10 mL) was treated with Et₃N (0.10 mL, 0.72 mmol) and morpholine (46 μL, 0.53 mmol). The reaction was stirred at room temperature for 18.5 h. The reaction was diluted with CH₂Cl₂ and washed with water. The aqueous layer was extracted further with CH₂Cl₂. The combined organic layers were dried over MgSO₄ and concentrated in vacuo to afford the title compound (0.16 g, 76%) as a yellow solid. $^1$H-NMR (CDCl₃; 400 MHz): δ 8.21 (d, 1H, J=9.2 Hz), 6.03 (d, 1H, J=9.2 Hz), 3.85-3.63 (m, 12H), 3.32-3.22 (m, 2H), 3.05-2.93 (m, 2H), 2.66-2.50 (m, 2H), 1.75-1.66 (m, 2H), 1.66-1.60 (m, 2H, partially obscured by water peak), 1.44-1.38 (m, 1H), 1.37-1.16 (m, 4H), 0.98 (d, 3H, J=6.4 Hz). LC-MS (ESI, m/z): Calcd. for C₂₁H₃₂N₆O₄, 433.2 (M+H), found 432.9.

c) 1-[4-(3'-Amino-4-methyl-3,4,5,6-tetrahydro-2H-[1,2']bipyridinyl-6'-yl)-piperazin-1-yl]-2-morpholin-4-yl-ethanone

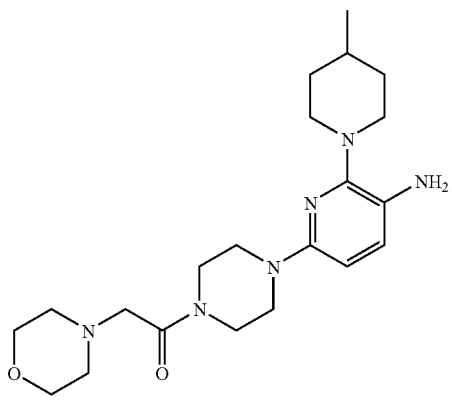

A solution of 1-[4-(4-methyl-3'-nitro-3,4,5,6-tetrahydro-2H-[1,2']bipyridinyl-6'-yl)-piperazin-1-yl]-2-morpholin-4-yl-ethanone (as prepared in the previous step, 0.16 g, 0.37 mmol) in 2:1 EtOH:water (3 mL) was treated with NH₄Cl (0.20 g, 3.7 mmol) and iron powder (0.10 g, 1.8 mmol). The reaction was heated to 100° C. for 50 min then cooled to room temperature. The mixture was neutralized with saturated aqueous NaHCO₃ and extracted with CH₂Cl₂. The combined organic layers were dried over MgSO₄ and concentrated in vacuo to afford the title compound (0.14 g, 100%), which was immediately used in the next reaction.

d) 5-Cyano-furan-2-carboxylic acid {4-methyl-6'-[4-(2-morpholin-4-yl-acetyl)-piperazin-1-yl]-3,4,5,6-tetrahydro-2H-[1,2']bipyridinyl-3'-yl}-amide trifluoroacetic acid salt

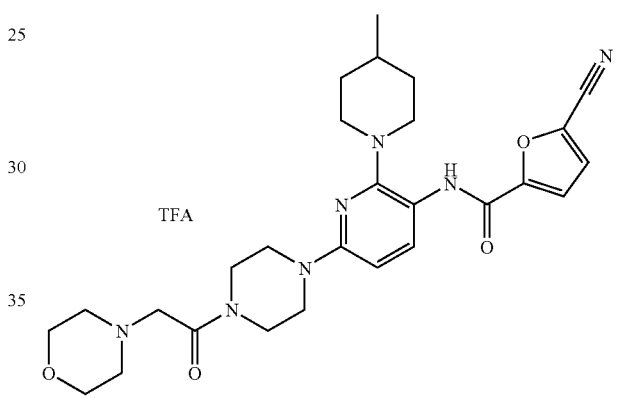

A solution of 5-cyano-furan-2-carboxylic acid (as prepared in Example 1, 0.10 g, 0.79 mmol) in CH₂Cl₂ (5 mL) and DMF (30 μL) was treated with oxalyl chloride (70 μL, 0.81 mmol) and stirred at room temperature for 1 h. The solvents were evaporated in vacuo, and the residue was taken up in CH₂Cl₂ (5 mL). A solution of 1-[4-(3'-amino-4-methyl-3,4,5,6-tetrahydro-2H-[1,2']bipyridinyl-6'-yl)-piperazin-1-yl]-2-morpholin-4-yl-ethanone (as prepared in the previous step, 0.14 g, 0.37 mmol) was treated with DIEA (0.13 mL, 0.74 mmol) and cooled to 0° C. The solution of acid chloride generated above was added dropwise, and the reaction was stirred at room temperature for 21 h. The reaction was diluted with CH₂Cl₂ and washed with water. The combined aqueous layers were extracted with CH₂Cl₂. The combined organic layers were dried over MgSO₄ and concentrated in vacuo. Reversed-phase HPLC (C-18 column) (10-50% acetonitrile in water with 0.1% TFA, over 30 min) afforded the title compound (22 mg, 11%) as a white solid. $^1$H-NMR (CDCl₃; 400 MHz): δ 8.75 (br s, 1H), 8.44 (d, 1H, J=8.8 Hz), 7.25 (d, 1H, J=4.0 Hz), 7.22 (d, 1H, J=4.0 Hz), 6.38 (d, 1H, J=8.8 Hz), 3.78-3.70 (m, 8H), 3.55 (app t, 2H, J=6.0 Hz), 3.47 (app t, 2H, J=6.0 Hz), 3.23 (s, 2H), 3.22-3.17 (m, 2H), 2.89-2.80 (m, 2H), 2.57-2.50 (m, 4H), 1.86-1.78 (m, 2H), 1.59-1.54 (m, 1H), 1.49-1.36 (m, 2H), 1.05 (d, 3H, J=6.4 Hz). LC-MS (ESI, m/z): Calcd. for C₂₇H₃₅N₇O₄, 522.3 (M+H), found 522.2.

Example 69

5-Cyano-furan-2-carboxylic acid [2-(4-fluoro-piperidin-1-yl)-4-(4-methyl-piperazin-1-yl)-phenyl]-amide trifluoroacetic acid salt

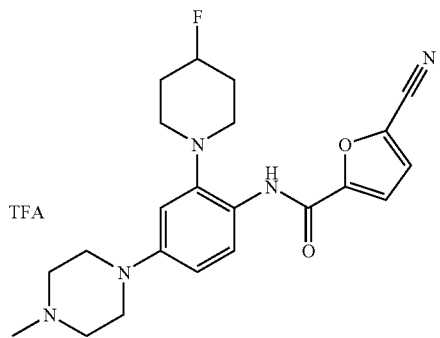

a) 1-(5-Chloro-2-nitro-phenyl)-4-fluoro-piperidine

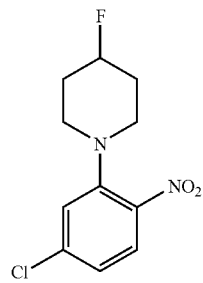

A solution of 4-chloro-2-fluoro-1-nitro benzene (0.30 g, 1.7 mmol) in toluene (5 mL) was treated with solid $Na_2CO_3$ (0.40 g, 3.7 mmol) and 4-fluoropiperidine hydrochloride (0.25 g, 1.8 mmol). The reaction was heated to 40° C. for 6 h. The reaction was diluted with EtOAc and washed with water. The organic layer was dried over $MgSO_4$ and concentrated in vacuo to afford the title compound (0.44 g, 99%) as a bright yellow oil. $^1$H-NMR ($CDCl_3$; 400 MHz): δ 7.79 (d, 1H, J=8.8 Hz), 7.10 (d, 1H, 2.0 Hz), 6.97 (dd, 1H, J=8.8 Hz, J=2.0 Hz), 4.97-4.79 (m, 1H), 3.26-3.17 (m, 2H), 3.06-2.99 (m, 2H), 2.14-1.97 (m, 4H). LC-MS (ESI, m/z): Calcd. for $C_{11}H_{12}ClFN_2O_2$, 225.2 (M-Cl+2H), found 225.2.

b) 1-[3-(4-Fluoro-piperidin-1-yl)-4-nitro-phenyl]-4-methyl-piperazine

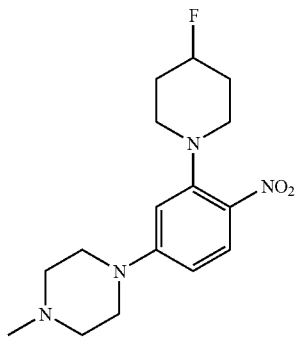

A solution of 1-(5-chloro-2-nitro-phenyl)-4-fluoro-piperidine (as prepared in the previous step, 0.44 g, 1.7 mmol) in 4-methylpiperazine (2 mL) was heated to 80° C. for 18.5 h. The solution was cooled to room temperature, diluted with $CH_2Cl_2$, and washed with water. The aqueous layer was further extracted with $CH_2Cl_2$. The combined organic layers were dried over $MgSO_4$ and concentrated in vacuo to afford the title compound (0.51 g, 93%) as a bright yellow solid. $^1$H-NMR ($CDCl_3$; 400 MHz): δ 8.04 (d, 1H, J=9.2 Hz), 6.45 (dd, 1H, J=9.2 Hz, J=2.4 Hz), 6.34 (d, 1H, J=2.4 Hz), 4.97-4.79 (m, 1H), 3.38 (app t, 4H, J=5.2 Hz), 3.26-3.15 (m, 4H), 3.07-2.98 (m, 4H), 2.54 (app t, 4H, J=5.2 Hz), 2.35 (s, 3H). LC-MS (ESI, m/z): Calcd. for $C_{16}H_{23}FN_4O_2$, 323.2 (M+H), found 323.2.

c) 2-(4-Fluoro-piperidin-1-yl)-4-(4-methyl-piperazin-1-yl)-phenylamine

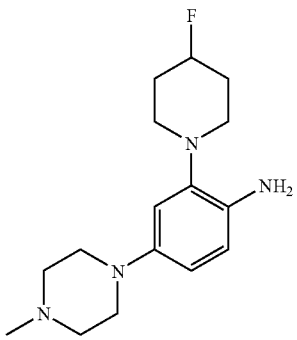

A solution of 1-[3-(4-fluoro-piperidin-1-yl)-4-nitro-phenyl]-4-methyl-piperazine (as prepared in the previous step, 0.20 g, 0.62 mmol) in 2:1 EtOH:water (6 mL) was treated with solid $NH_4Cl$ (0.33 g, 6.2 mmol) and iron powder (0.17 g, 3.1 mmol) then heated to 100° C. for 2.5 h. The reaction was cooled to room temperature, treated with 1 drop of glacial acetic acid, and heated again to 100° C. for 30 min. The reaction was cooled to room temperature and neutralized with saturated aqueous $NaHCO_3$. The product was extracted with $CH_2Cl_2$, and the combined organic layers were dried over $MgSO_4$ and concentrated in vacuo to afford the title compound (0.19 g, 99%), which was used immediately in the next reaction. LC-MS (ESI, m/z): Calcd. for $C_{16}H_{25}FN_4$, 293.2 (M+H), found 293.1.

d) 5-Cyano-furan-2-carboxylic acid [2-(4-fluoro-piperidin-1-yl)-4-(4-methyl-piperazin-1-yl)-phenyl]-aide trifluoroacetic acid salt

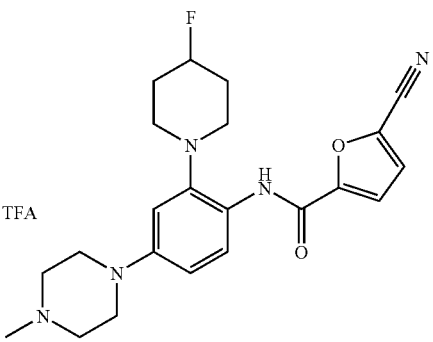

Using a procedure similar to Example 68, step (d), 2-(4-fluoro-piperidin-1-yl)-4-(4-methyl-piperazin-1-yl)-phenylamine (as prepared in the previous step, 0.19 g, 0.62 mmol)

was coupled to 5-cyano-furan-2-carboxylic acid (as prepared in Example 1, 85 mg, 0.62 mmol). Reversed-phase HPLC (C-18 column) (10-50% acetonitrile in water with 0.1% TFA over 30 min) afforded the title compound (7.5 mg, 3%) as a white solid. $^1$H-NMR (CDCl$_3$; 400 MHz): δ 9.44 (br s, 1H), 8.32 (d, 1H, J=8.8 Hz), 7.30-7.26 (m, 1H), 7.25-7.21 (m, 1H), 6.82 (d, 1H, J=2.8 Hz), 6.75 (dd, 1H, J=8.8 Hz, J=2.8 Hz), 5.06-4.85 (m, 1H), 3.34-3.26 (m, 4H), 3.15-3.06 (m, 2H), 2.95-2.86 (m, 4H), 2.86-2.77 (m, 2H), 251 (s, 3H), 2.17-2.10 (m, 4H). LC-MS (ESI, m/z): Calcd. for C$_{22}$H$_{26}$FN$_5$O$_2$ 412.2 (M+H), found 412.2.

Example 70

4-Cyano-1H-imidazole-2-carboxylic acid [2-(3-fluoro-piperidin-1-yl)-4-(4-methyl-piperazin-1-yl)-phenyl]-amine tris(trifluoroacetic acid salt)

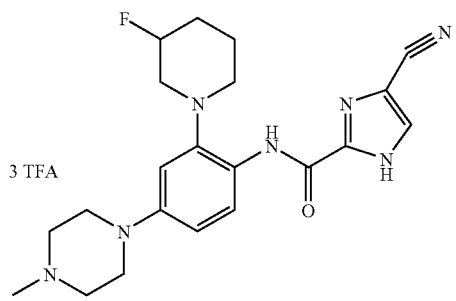

a) 1-(5-Chloro-2-nitro-phenyl)-3-fluoro-piperidine

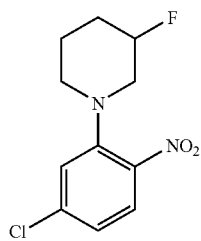

A solution of 4-chloro-2-fluoro-1-nitro-benzene (0.30 g, 1.7 mmol) in toluene (5 mL) was treated with solid Na$_2$CO$_3$ (0.40 g, 3.7 mmol) and 3-fluoropiperidine (0.25 mg, 1.8 mmol) and heated to 40° C. for 6 h. The reaction was diluted with EtOAc and washed with water. The organic layer was dried over MgSO$_4$ and concentrated in vacuo to afford the title compound (0.43 g, 98%) as a bright yellow oil. $^1$H-NMR (CDCl$_3$; 400 MHz): δ 7.76 (d, 1H, J=8.8 Hz), 7.11 (d, 1H, J=2.4 Hz), 6.95 (dd, 1H, J=8.8, 2.4 Hz), 4.86-4.67 (m, 1H), 3.46-3.35 (m, 1H), 3.15-3.06 (m, 2H), 2.99-2.92 (m, 1H), 2.10-1.90 (m, 2H), 1.88-1.69 (m, 2H). LC-MS (ESI, m/z): Calcd. for C$_{11}$H$_{12}$ClFN$_2$O$_2$ 259.1 (M+H), found 259.1.

b) 1-[3-(3-Fluoro-piperidin-1-yl)-4-nitro-phenyl]-4-methyl-piperazine

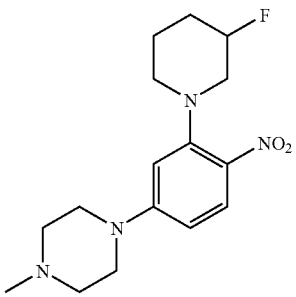

A solution of 1-(5-chloro-2-nitro-phenyl)-3-fluoro-piperidine (as prepared in the previous step, 0.44 g, 1.7 mmol) in N-methylpiperazine (2 mL) was heated to 80° C. for 18.5 h. The reaction was cooled to room temperature, diluted with CH$_2$Cl$_2$ and washed with water. The aqueous layer was extracted with CH$_2$Cl$_2$. The combined organic layers were dried over MgSO$_4$ and concentrated in vacuo to afford the title compound (0.50 g, 93%) as a yellow solid. $^1$H-NMR (CDCl$_3$; 400 MHz): δ 8.00 (d, 1H, J=9.2 Hz), 6.44 (dd, 1H, J=9.2 Hz, J=2.8 Hz), 6.34 (d, 1H, J=2.8 Hz), 4.91-4.71 (m, 1H), 3.54-3.44 (m, 1H), 3.41-3.36 (m, 4H), 3.18-3.10 (m, 1H), 3.02-2.94 (m, 1H), 2.87-2.80 (m, 1H), 2.5-2.52 (m, 4H), 2.35 (s, 3H), 1.82-1.66 (m, 4H). LC-MS (ESI, m/z): Calcd. for C$_{16}$H$_{23}$FN$_4$O$_2$ 323.2 (M+H), found 323.2.

c) 2-(3-Fluoro-piperidin-1-yl)-4-(4-methyl-piperazin-1-yl)-phenylamine

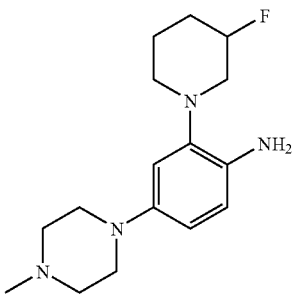

A solution of 1-[3-(3-fluoro-piperidin-1-yl)-4-nitro-phenyl]4-methyl-piperazine (as prepared in the previous step, 60 mg, 0.19 mmol) in 2:1 EtOH:water (6 mL), was treated with glacial AcOH (1 drop) and iron powder (10 mg, 0.93 mmol). The mixture was heated to 80° C. for 30 min. The reaction cooled to room temperature, diluted with EtOAc and washed with saturated aqueous NaHCO$_3$. The aqueous layer was extracted with EtOAc. The combined organic layers were dried over MgSO$_4$ and concentrated in vacuo to afford the title compound (46 mg, 84%), which was used directly in the next reaction. LC-MS (ESI, m/z): Calcd. for C$_{16}$H$_{25}$FN$_4$ 293.2 (M+H), found 293.2.

d) 4-Cyano-1-(2-trimethylsilanyl-ethoxymethyl)-1H-imidazole-2-carboxylic acid [2-(3-fluoro-piperidin-1-yl)-4-(4-methyl-piperazin-1-yl)-phenyl]-amide

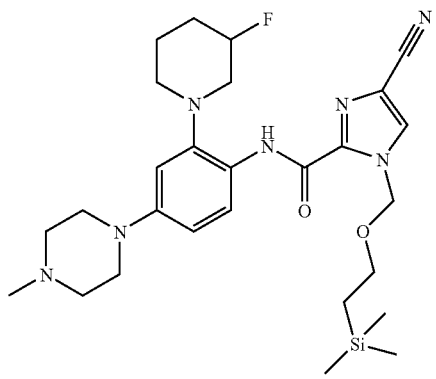

A suspension of 4-cyano-1-(2-trimethylsilanyl-ethoxymethyl)-1H-imidazole-2-carboxylate potassium salt (as prepared in Example 3, step (d), 48 mg, 0.16 mmol) in CH$_2$Cl$_2$ (5 mL) was treated with DIEA (68 μL, 0.39 mmol) and PyBroP (0.11 g, 0.24 mmol). The reaction stirred at room temperature for 10 min. A solution of 2-(3-fluoro-piperidin-1-yl)-4-(4-methyl-piperazin-1-yl)-phenylamine (as prepared in the previous step, 46 mg, 0.16 mmol) in CH$_2$Cl$_2$ (4 mL) was added, and the reaction was stirred at room temperature for 19.5 h. The reaction was diluted with CH$_2$Cl$_2$ and washed with saturated aqueous NaHCO$_3$ and water. The organic layer was dried over MgSO$_4$ and concentrated in vacuo to afford the title compound (62 mg, 70%) as an off-white solid, which was used directly in the next reaction. LC-MS (ESI, m/z): Calcd. for C$_{27}$H$_{40}$FN$_7$O$_2$Si, 542.3 (M+H), found 542.4.

e) 4-Cyano-1H-imidazole-2-carboxylic acid [2-(3-fluoro-piperidin-1-yl)-4-(4-methyl-piperazin-1-yl)-phenyl]-amide tris(trifluoroacetic acid salt)

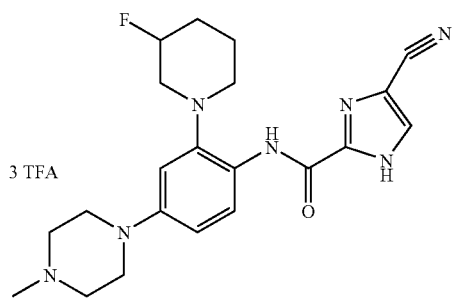

A solution of 4-cyano-1-(2-trimethylsilanyl-ethoxymethyl)-1H-imidazole-2-carboxylic acid [2-(3-fluoro-piperidin-1-yl)-4-(4-methyl-piperazin-1-yl)-phenyl]-amide (as prepared in the previous step, 85 mg, 0.16 mmol) in CH$_2$Cl$_2$ (20 mL) was treated with TFA (2 mL) and stirred at room temperature for 15 h. The solvent was evaporated in vacuo. Silica gel chromatography (10% MeOH in EtOAc with 0.1% DIEA) followed by reversed-phase HPLC (C-18 column) (10-50% acetonitrile in water with 0.1% TFA over 30 min) afforded the title compound (21 mg, 26%) as a white solid. $^1$H-NMR (CDCl$_3$; 400 MHz): δ 8.27-8.22 (m, 1H), 7.72 (s, 1H), 6.78-6.72 (m, 2H), 4.98-4.78 (m, 1H), 3.67 (m, 7H), 3.26-3.16 (m, 2H), 2.95-2.85 (m, 5H), 2.78-2.69 (m, 1H), 2.22-2.00 (m, 2H), 1.93-1.69 (m, 2H). LC-MS (ESI, n/z): Calcd. for C$_{21}$H$_{26}$FN$_7$O 412.2 (M+H), found 412.1.

Example 71

An alternate method for the synthesis of the intermediate described in Example 1 is described below.

5-Cyano-furan-2-carboxylic acid

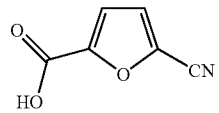

A 250-mL, three-neck, round-bottom flask equipped with a mechanical stirrer, a heating mantle, and a condenser was charged with 5-formyl-2-furancarboxylic acid (9.18 g, 65.6 mmol) and pyridine (60 mL). Hydroxylamine hydrochloride (5.01 g, 72.2 mmol) was added and the mixture was heated to 85° C. Acetic anhydride (40 mL) was added and the reaction was stirred at 85° C. for 3 h, after which time the solvent was evaporated at 40° C. under reduced pressure. The residue was dissolved in water, basified with 2.0 N NaOH solution to pH 9, and extracted with 4:1 dichloromethane/2-propanol until the pyridine was completely removed (5×200 mL). The aqueous solution was then acidified with 2.0 N HCl solution to pH 2, saturated with solid NaCl, and extracted with 4:1 dichloromethane/2-propanol (5×200 mL). The combined organic extracts were dried over Na$_2$SO$_4$ and concentrated in vacuo to dryness. The residue was crystallized from dichloromethane to give 6.80 g of the title compound as a white solid (76%). Mass spectrum (ESI-neg, m/z) Calcd. for C$_6$H$_3$NO$_3$, 136.0 (M−H), found 136.1. The $^1$H NMR spectrum was consistent with the assigned structure.

Example 72

An alternate method for the synthesis of the imidazole intermediate is described below:

4-Cyano-1-(2-trimethylsilanyl-ethoxymethyl)-1H-imidazole-2-carboxylic acid potassium salt

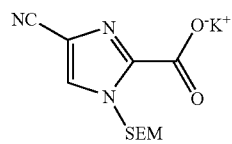

a) 1H-Imidazole-4-carbonitrile

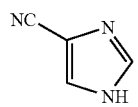

A 22-L, four-neck, round-bottom flask equipped with a mechanical stirrer, a temperature probe, a condenser, and an addition funnel with a nitrogen inlet was charged with 1H-imidazole-4-carboxaldehyde (Aldrich, 1.10 kg, 11.5 mol) and pyridine (3.0 L, 3.0 mol). The reaction flask was cooled to 8° C. with an ice bath and hydroxylamine hydrochloride (871 g, 12.5 mol) was added slowly in portions to maintain the internal temperature below 30° C. The reaction was allowed to cool to ambient temperature and stirred for 2 h at ambient temperature. The resulting thick yellow solution was heated to 80° C. with a heating mantle and acetic anhydride (2.04 L, 21.6 mol) was added dropwise over 200 min to maintain the temperature below 110° C. during the addition. The reaction mixture was heated at 100° C. for 30 min, after which time it was allowed to cool to ambient temperature and then further cooled in an ice bath. The pH was adjusted to 8.0 (pH meter) by the addition of 25 wt % NaOH (5.5 L) at such a rate that the internal temperature was maintained below 30° C. The reaction mixture was then transferred into a 22-L separatory funnel and extracted with ethyl acetate (6.0 L). The combined organic layer was washed with brine (2×4.0 L), dried over MgSO$_4$, filtered, and concentrated to dryness under reduced pressure at 35° C. to give the crude product as a yellow semisolid. The resulting semisolid was suspended in toluene (3.0 L) and stirred for 1 h, after which time it was filtered to give a light yellow solid, which was resuspended in toluene (3.0 L) and stirred for 1 h. The resulting slurry was filtered and the filter cake washed with toluene (2×500 mL) to give the title compound as a light yellow solid [870 g, 82%]. The $^1$H and $^{13}$C NMR spectra were consistent with the assigned structure.

b) 1-(2-Trimethylsilanyl-ethoxymethyl)-1H-imidazole-4-carbonitrile and 3-(2-trimethylsilanyl-ethoxymethyl)-3H-imidazole-4-carbonitrile

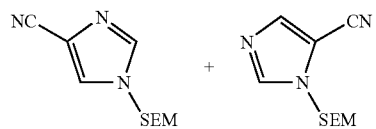

A 22-L, four-neck, round-bottom flask equipped with a mechanical stirrer, a temperature probe, and an addition funnel with a nitrogen inlet was charged with 1H-imidazole-4-carbonitrile (830 g, 8.91 mol, as prepared in the previous step), potassium carbonate (2.47 kg, 17.8 mol), and acetone (6.0 L). Agitation was initiated and the mixture was cooled to 10° C. with an ice bath. SEMCl (1.50 kg, 9.00 mol) was added through the addition funnel over 210 min to maintain the internal temperature below 15° C. The reaction was then allowed to warm to ambient temperature and stirred at ambient temperature overnight (20 h). The reaction mixture was then cooled in an ice bath to 10° C. and quenched by the slow addition of water (8.0 L) over 30 min to maintain the internal temperature below 30° C. The resulting mixture was transferred to a 22-L separatory funnel and extracted with ethyl acetate (2×7.0 L). The combined organics were concentrated under reduced pressure at 35° C. to give the crude product as a dark brown oil, which was purified through a plug of silica gel (16.5×20 cm, 2.4 kg silica gel) using 2:1 heptane/ethyl acetate (15 L) as eluent. The fractions containing the product were combined and concentrated under reduced pressure at 35° C. to afford a mixture of the title compounds as a light brown oil [1785 g, 90%]. The $^1$H NMR spectrum was consistent with the assigned structure and indicated the presence of a 64:36 ratio of regioisomers.

c) 2-Bromo-1-(2-trimethylsilanyl-ethoxymethyl)-1H-imidazole-4-carbonitrile

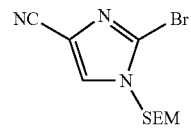

A 22-L, four-neck, round-bottom flask equipped with a mechanical stirrer, a temperature probe, and a condenser with a nitrogen inlet was charged with a mixture of 1-(2-trimethylsilanyl-ethoxymethyl)-1H-imidazole-4-carbonitrile and 3-(2-trimethylsilanyl-ethoxymethyl)-3H-imidazole-4-carbonitrile [600 g, 2.69 mol, as prepared in the previous step) and carbon tetrachloride (1.8 L). Agitation was initiated and the mixture was heated to 60° C. At this point N-bromosuccinimide (502 g, 2.82 mol) was added in several portions over 30 min, which resulted in an exotherm to 74° C. The reaction was allowed to cool to 60° C. and further stirred at 60° C. for 1 h. The reaction was allowed to cool slowly to ambient temperature and the resulting slurry was filtered and the filtrate washed with satd NaHCO$_3$ solution (4.0 L). The organics were passed through a plug of silica gel (8×15 cm, silica gel; 600 g) using 2:1 heptane/ethyl acetate (6.0 L) as eluent. The fractions containing the product (based on TLC analysis) were combined and concentrated under reduced pressure to give a crystalline light yellow solid, which was then filtered and washed with heptane (500 mL) to give the title compound as a crystalline white solid [593 g, 73%]. The $^1$H and $^{13}$C NMR spectra were consistent with the assigned structure and showed no evidence of the minor regioisomers.

d) 4-Cyano-1-(2-trimethylsilanyl-ethoxymethyl)-1H-imidazole-2-carboxylic acid ethyl ester

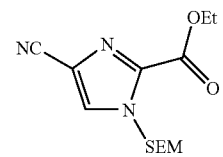

A 12-L, four-neck, round-bottom flask equipped with a mechanical stirrer, a temperature probe, and an addition funnel with a nitrogen inlet was charged with 2-bromo-1-(2-trimethylsilanyl-ethoxymethyl)-1H-imidazole-4-carbonitrile [390 g, 1.29 mol, as prepared in the previous step) and anhydrous tetrahydrofuran (4.0 L). Agitation was initiated and the reaction mixture was cooled to −50° C. using a dry ice/acetone bath. Isopropylmagnesium chloride (2.0 M in THF, 760 mL, 1.52 mol) was added through the addition funnel over 30 min to maintain the internal temperature below −40° C. The reaction was stirred for a further 30 min at −43° C., after which time it was cooled to −78° C. Ethyl chloroformate (210 mL, 2.20 mol) was added through the addition funnel over 10 min to maintain the internal temperature below −60° C. The reaction was stirred for a further 40 min at −70° C., at which point the dry ice/acetone bath was removed and the reaction was allowed to warm to ambient temperature over 1.5 h. The reaction mixture was cooled in an ice bath to 0° C. and quenched by the slow addition of satd ammonium chloride solution (1.8 L) at such a rate that the internal temperature was maintained below 10° C. The reaction mixture was transferred into a 12-L separatory funnel, diluted with ethyl acetate (4.0 L), and the layers were separated. The organic layer was washed with brine (2×2.0 L) and concentrated under reduced pressure at 35° C. to give a brown oil. The crude oil was dissolved in dichloromethane (300 mL) and purified by chromatography (15×22 cm, 1.5 kg of silica gel, 10:1 to 4:1 heptane/ethyl acetate) to give a yellow oil, which was dissolved in EtOAc (100 mL), diluted with heptane (2.0 L), and stored in a refrigerator for 5 h. The resulting slurry was filtered to give the title compound as a crystalline white solid (141 g, 37%). The $^1$H and $^{13}$C NMR spectra were consistent with the assigned structure.

e) 4-Cyano-1-(2-trimethylsilanyl-ethoxymethyl)-1H-imidazole-2-carboxylic acid potassium salt

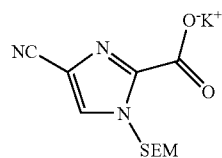

A 5-L, three-neck, round-bottom flask equipped with a mechanical stirrer, a temperature probe, and an addition funnel with a nitrogen inlet was charged with 5 [400 g, 1.35 mol) and ethanol (4.0 L). Agitation was initiated and a water bath was applied after all of the solid had dissolved. A solution of 6 N KOH (214.0 mL, 1.29 mol) was added through the addition funnel over 15 min to maintain the internal temperature below 25° C. and the reaction was stirred for 5 min at room temperature. The solution was then concentrated to dryness under reduced pressure at 20° C. to give a white solid. The resulting solid was suspended in methyl t-butyl ether (MTBE, 4.0 L) and stirred for 30 min, after which time the slurry was filtered and the filter cake washed with MTBE (1.0 L) to give the title compound as a white solid, which was further dried under vacuum at ambient temperature for 4 d [366 g, 89%). The $^1$H NMR, $^{13}$C NMR, and mass spectra were consistent with the assigned structure. Anal. Calcd for $C_{11}H_{16}KN_3O_3Si$: C, 43.25; H, 5.28; N, 13.76. Found: C, 42.77; H, 5.15; N, 13.37. Karl Fisher: 1.3% $H_2O$.

IV. Results

An autophosphorylation, fluorescence polarization competition immunoassay was used to determine the potency for c-fms inhibition exhibited by selected compounds of Formula I. The assay was performed in black 96-well microplates (LJL BioSystems). The assay buffer used was 100 mM 4-(2-hydroxyethyl)piperazine 1-ethanesulfonic acid (HEPES), pH 7.5, 1 mM 1,4-dithio-DL-threitol (DTT), 0.01% (v/v) Tween-20. Compounds were diluted in assay buffer containing 4% dimethylsulfoxide (DMSO) just prior to the assay. To each well, 5 µL of compound were added followed by the addition of 3 µL of a mix containing 33 nM c-fms (Johnson & Johnson PRD) and 16.7 mM $MgCl_2$ (Sigma) in assay buffer. The kinase reaction was initiated by adding 2 µL of 5 mM ATP (Sigma) in assay buffer. The final concentrations in the assay were 10 nM c-fms, 1 mM ATP, 5 mM $MgCl_2$, 2% DMSO. Control reactions were ran in each plate: in positive and negative control wells, assay buffer (made 4% in DMSO) was substituted for the compound; in addition, positive control wells received 1.2 µL of 50 mM ethylenediaminetetraacetic acid (EDTA).

The plates were incubated at room temperature for 45 min. At the end of the incubation, the reaction was quenched with 1.2 µL of 50 mM EDTA (EDTA was not added to the positive control wells at this point; see above). Following a 5-min incubation, each well received 10 µL of a 1:1:3 mixture of anti-phosphotyrosine antibody, 10×, PTK green tracer, 10× (vortexed), FP dilution buffer, respectively (all from PanVera, cat. #P2837). The plate was covered, incubated for 30 min at room temperature and the fluorescence polarization was read on the Analyst. The instrument settings were: 485 nm excitation filter; 530 nm emission filter; Z height: middle of well; G factor: 0.93. Under these conditions, the fluorescence polarization values for positive and negative controls were approximately 300 and 150, respectively, and were used to define the 100% and 0% inhibition of the c-fms reaction. $IC_{50}$ values are obtained as averages of three independent measurements. Compounds were classed as A, B, or C, with A: <0.020 µM; B: >0.020 µM and <0.050 µM; and C: >0.050 µM and <0.5 µM.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All publications disclosed in the above specification are hereby incorporated by reference in full.

The claimed invention is:

1. The compounds of Formula I:

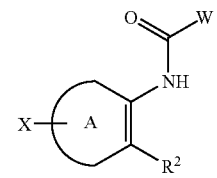

or a tautomer or pharmaceutically acceptable salt thereof, wherein:

A is phenyl, pyridinyl, pyrazinyl, pyrimidinyl, or pyridazinyl, which may be substituted with one of chloro, fluoro, methyl, —$N_3$, —$NH_2$, —NH(alkyl), —N(alkyl)$_2$, —S(alkyl), —O(alkyl), alkylOC(O)alkyl, or 4-aminophenyl;

W is pyrrolyl, imidazolyl, isoxazolyl, oxazolyl, 1,2,4-triazolyl or furanyl, any of which may be connected through any carbon atom, wherein the pyrrolyl, imidazolyl, isoxazolyl, oxazolyl, 1,2,4-triazolyl, or furanyl may contain one —CN, —$NO_2$, —OMe, C(=NH)NOH, or —$CF_3$ substitution, connected to any other carbon;

$R^2$ is piperidinyl, pyrrolyl or pyrrolidinyl, any of which may be independently substituted, with one or two of each of the following: chloro, fluoro, oxo, and $C_{(1-3)}$alkyl, with the proviso that $R^2$ is connected to the ring A through the nitrogen atom;

X is

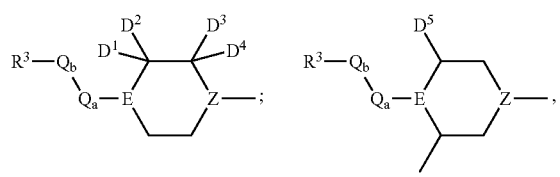

-continued

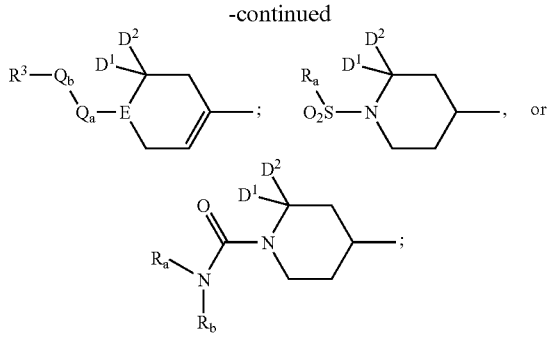

Z is CH or N;
D¹ and D² are hydrogens or taken together form a double bond to an oxygen;
D³ and D⁴ are hydrogens or taken together form a double bond to an oxygen;
D⁵ is hydrogen or —CH₃, wherein said —CH₃ may be relatively oriented syn or anti;
$R_a$ and $R_b$ are independently hydrogen, cycloalkyl, haloalkyl, aryl, aralkyl, heteroaryl, or heteroaralkyl;
E is
  N, S, O, SO or SO₂, with the proviso that E may not be N if the following three conditions are simultaneously met: $Q_a$ is absent, $Q_b$ is absent, and R³ is an amino group or cyclic amino radical wherein the point of attachment to E is N;
$Q_a$ is absent, —CH₂—, —CH₂CH₂—, or C(O);
$Q_b$ is
  absent, —NH—, —CH₂—, —CH₂CH₂—, or C(O), with the proviso that $Q_b$ may not be C(O) if $Q_a$ is C(O), and further provided that $Q_b$ may not be —NH— if E is N and $Q_a$ is absent, further provided that $Q_b$ may not be —NH— if R³ is an amino group or cyclic amino radical wherein the point of attachment to $Q_b$ is N;
R³ is
  hydrogen, phenyl, hydroxyalkylamino, (hydroxyalkyl)₂amino, hydroxyalkyl(alkyl)amino, alkylamino, aminoalkyl, dihydroxyalkyl, alkoxy, dialkylamino, hydroxyalkyl, —COOH, —CONH₂, —CN, —SO₂-alkyl-R⁴, —NH₂, or a 5- or 6-membered ring which contains at least one heteroatom N and may optionally contain an additional heteromoiety selected from S, SO₂, N, and O, and the 5- or 6-membered ring may be saturated, partially unsaturated or aromatic wherein aromatic nitrogen in the 5- or 6-membered ring may be present as N-oxide, and the 5- or 6-membered ring may be optionally substituted with methyl, halogen, alkylamino, or alkoxy; R³ may also be absent, with the proviso that R³ is not absent when E is nitrogen;
R⁴ is hydrogen, —OH, alkoxy, carboxy, carboxamido, or carbamoyl.

2. A compound of claim 1 wherein W is substituted with one —CN.
3. A compound of claim 1 wherein
A is
  pyridinyl, which may be substituted with one of chloro, fluoro, methyl, —N₃, —NH₂, —NH(alkyl), —N(alkyl)₂, —S(alkyl), —O(alkyl), or 4-aminophenyl;
W is
  imidazolyl, which may contain one —CN; and
R² is
  piperidinyl.

4. A compound of claim 1 wherein:
W is
  imidazolyl, 1,2,4-triazolyl or furanyl any of which may be connected through any carbon atom, wherein the imidazolyl, 1,2,4-triazolyl, or furanyl may contain one —CN, connected to any other carbon;
R² is
  piperidinyl, pyrrolyl or pyrrolidinyl;
X is

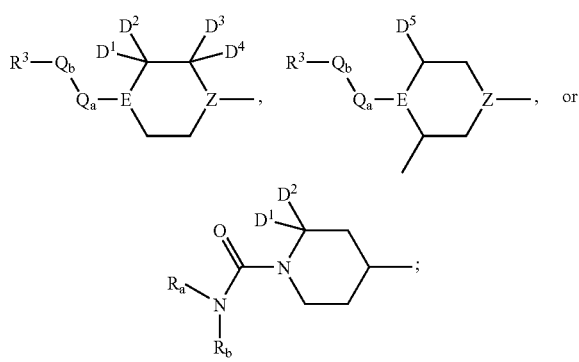

E is
  N or SO₂, with the proviso that E may not be N if the following three conditions are simultaneously met: $Q_a$ is absent, $Q_b$ is absent, and R³ is an amino group or cyclic amino radical wherein the point of attachment to E is N; and
R³ is
  hydrogen, phenyl, hydroxyalkylamino, hydroxyalkyl(alkyl)amino, alkylamino, aminoalkyl, dihydroxyalkyl, alkoxy, dialkylamino, hydroxyalkyl, —COOH, —CONH₂, —CN, —SO₂CH₃, —NH₂, or a 5- or 6-membered ring selected from the group consisting of: piperidinyl, morpholinyl, imidazolyl, and pyrindinyl, wherein the 5- or 6-membered ring may be optionally substituted with methyl, halogen, alkylamino, or alkoxy, R³ may also be absent, with the proviso that R³ is not absent when E is nitrogen.

5. A compound of claim 1 wherein:
A is
  phenyl which may be substituted with one of chloro, fluoro, or methyl;
X is

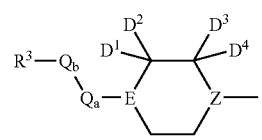

and is attached to the phenyl A ring para to the nitrogen substituent, as depicted in formula II;

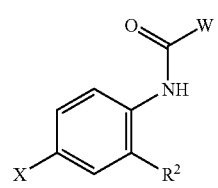

II

D³ and D⁴ are hydrogen;

E is N or SO$_2$, with the proviso that E may not be N if the following three conditions are simultaneously met: Q$_a$ is absent, Q$_b$ is absent, and R$^3$ is an amino group or cyclic amino radical wherein the point of attachment to E is N; and R$^3$ is hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —CONH$_2$, —CN, —SO$_2$CH$_3$—, —NH$_2$, morpholinyl; R$^3$ may also be absent, with the proviso that R$^3$ is not absent when E is nitrogen.

6. A compound of claim 5 wherein:

A is phenyl;

W is furan-2-yl, 1H-pyrrol-2-yl, or 1H-imidazol-2-yl, any of which may be substituted at the 4 or 5 carbons with —CN;

R$^2$ is piperidinyl optionally substituted with chloro, fluoro, or C$_{(1-3)}$alkyl.

7. A compound of claim 6 wherein:

W is 3H-2-imidazolyl-4-carbonitrile or 5-cyano-1H-pyrrol-2-yl;

R$^2$ is piperidinyl optionally substituted with fluoro or methyl;

E is N, with the proviso that E may not be N if the following three conditions are simultaneously met: Q$_a$ is absent, Q$_b$ is absent, and R$^3$ is an amino group or cyclic amino radical wherein the point of attachment to E is N; and Z is CH.

8. A compound of claim 7 wherein:

W is 3H-2-imidazolyl-4-carbonitrile;

Q$_a$ is C(O);

R$^3$ is hydrogen, piperidinyl, alkylamino, dialkylamino, hydroxyalkylamino, (hydroxyalkyl)$_2$amino, imidazolyl, 1-methyl imidazolyl, pyridyl, pyridyl N-oxide, hydroxyalkyl, —COOH, —CONH$_2$, —CN, —SO$_2$CH$_3$, —NH$_2$, morpholinyl; R$^3$ may also be absent, with the proviso that R$^3$ is not absent when is nitrogen.

9. A compound selected from the group consisting of:

5-Cyano-furan-2-carboxylic acid (4-morpholin-4-yl-2-piperidin-1-yl-phenyl)-amide;

5-Cyano-furan-2-carboxylic acid (2-piperidin-1-yl-4-thiomorpholin-4-yl-phenyl)-amide;

5-Cyano-furan-2-carboxylic acid [4-(1-oxo-1λ$^4$-thiomorpholin-4-yl)-2-piperidin-1-yl-phenyl]-amide;

5-Cyano-furan-2-carboxylic acid [4-(1,1-dioxo-1λ$^6$-thiomorpholin-4-yl)-2-piperidin-1-yl-phenyl]-amide;

5-Cyano-furan-2-carboxylic acid [2-(4-methyl-piperidin-1-yl)-4-morpholin-4-yl-phenyl]-amide;

4-Methyl-piperazine-1-carboxylic acid {4-[(5-cyano-furan-2-carbonyl)-amino]-3-piperidin-1-yl-phenyl}-methyl-amide;

5-Cyano-furan-2-carboxylic acid [4-(4-methyl-piperazin-1-yl)-2-piperidin-1-yl-phenyl]-amide hydrochloride;

5-Cyano-furan-2-carboxylic acid [2-(4-methyl-piperidin-1-yl)-4-(1,2,3,6-tetrahydro-pyridin-4-yl)-phenyl]-amide dihydrochloride;

5-Cyano-furan-2-carboxylic acid [2-(4-methyl-piperidin-1-yl)-4-piperidin-4-yl-phenyl]-amide bis(trifluoroacetic acid salt);

4-Cyano-1H-pyrrole-2-carboxylic acid [2-(4-methyl-piperidin-1-yl)-4-piperidin-4-yl-phenyl]-amide bis(trifluoroacetic acid salt);

5-Cyano-furan-2-carboxylic acid [4-(1-acetyl-piperidin-4-yl)-2-(4-methyl-piperidin-1-yl)-phenyl]l-amide;

5-Cyano-1H-imidazole-2-carboxylic acid [4-(4-methyl-piperazin-1-yl)-2-piperidin-1-yl-phenyl]-amide trifluoroacetic acid salt;

3H-Imidazole-4-carboxylic acid [4-(4-methyl-piperazin-1-yl)-2-piperidin-1-yl-phenyl]-amide bis(trifluoroacetic acid salt);

1H-Imidazole-2-carboxylic acid [4-(4-methyl-piperazin-1-yl)-2-piperidin-1-yl-phenyl]-amide bis(trifluoroacetic acid salt);

3H-Imidazole-2,4-dicarboxylic acid 2-amide 4-{[4-(4-methyl-piperazin-1-yl)-2-piperidin-1-yl-phenyl]-amide}trifluoroacetic acid salt;

1H-Imidazole-2-carboxylic acid [3-chloro-4-(4-methyl-piperazin-1-yl)-2-piperidin-1-yl-phenyl]-amide bis(trifluoroacetic acid salt);

4-Cyano-1H-pyrrole-2-carboxylic acid [4-[1-(imidazole-1-carbonyl)-piperidin-4-yl]-2-(4-methyl-piperidin-1-yl)-phenyl]-amide;

4-Cyano-1H-pyrrole-2-carboxylic acid {2-(4-methyl-piperidin-1-yl)-4-[1-(pyridine-3-carbonyl)-piperidin-4-yl]-phenyl}-amide;

4-Cyano-1H-pyrrole-2-carboxylic acid [4-[1-(2-dimethylamino-acetyl)-piperidin-4-yl]-2-(4-methyl-piperidin-1-yl)-phenyl]-amide;

4-Cyano-1H-pyrrole-2-carboxylic acid {2-(4-methyl-piperidin-1-yl)-4-[1-(2,2,2-trifluoroethyl)-piperidin-4-yl]-phenyl}-amide;

4-Cyano-1H-imidazole-2-carboxylic acid [4-(1,1-dioxohexahydro-1λ$^6$-thiopyran-4-yl)-2-(4-methyl-piperidin-1-yl)-phenyl]-amide;

4-Cyano-1H-pyrrole-2-carboxylic acid {2-(4-methyl-piperidin-1-yl)-4-[1-(morpholine-4-carbonyl)-piperidin-4-yl]-phenyl}-amide;

4-Cyano-1H-pyrrole-2-carboxylic acid [4-[1-(2-methanesulfonyl-acetyl)-piperidin-4-yl]-2-(4-methyl-piperidin-1-yl)-phenyl]-amide;

4-Cyano-1H-pyrrole-2-carboxylic acid [4-(1,1-dioxohexahydro-1λ$^6$-thiopyran-4-yl)-2-(4-methyl-piperidin-1-yl)-phenyl]-amide;

5-Cyano-furan-2-carboxylic acid[4-[4-methyl-piperazin-1-yl)-2-morpholin-4-yl-phenyl]-amide;

5-Cyano-furan-2-carboxylic acid[2-(4-methyl-piperazin-1-yl)-4-(4-methyl-piperidin-1-yl)-pyrimidin-5-yl]-amide trifluoroacetic acid salt;

or pharmaceutically acceptable salts thereof.

10. A pharmaceutical composition, comprising a compound of claim 1 and a pharmaceutically acceptable carrier.

11. A pharmaceutical dosage form comprising a pharmaceutically acceptable carrier and from about 0.5 mg to about 10 g of at least one compound of claim 1.

* * * * *